Figure 4:
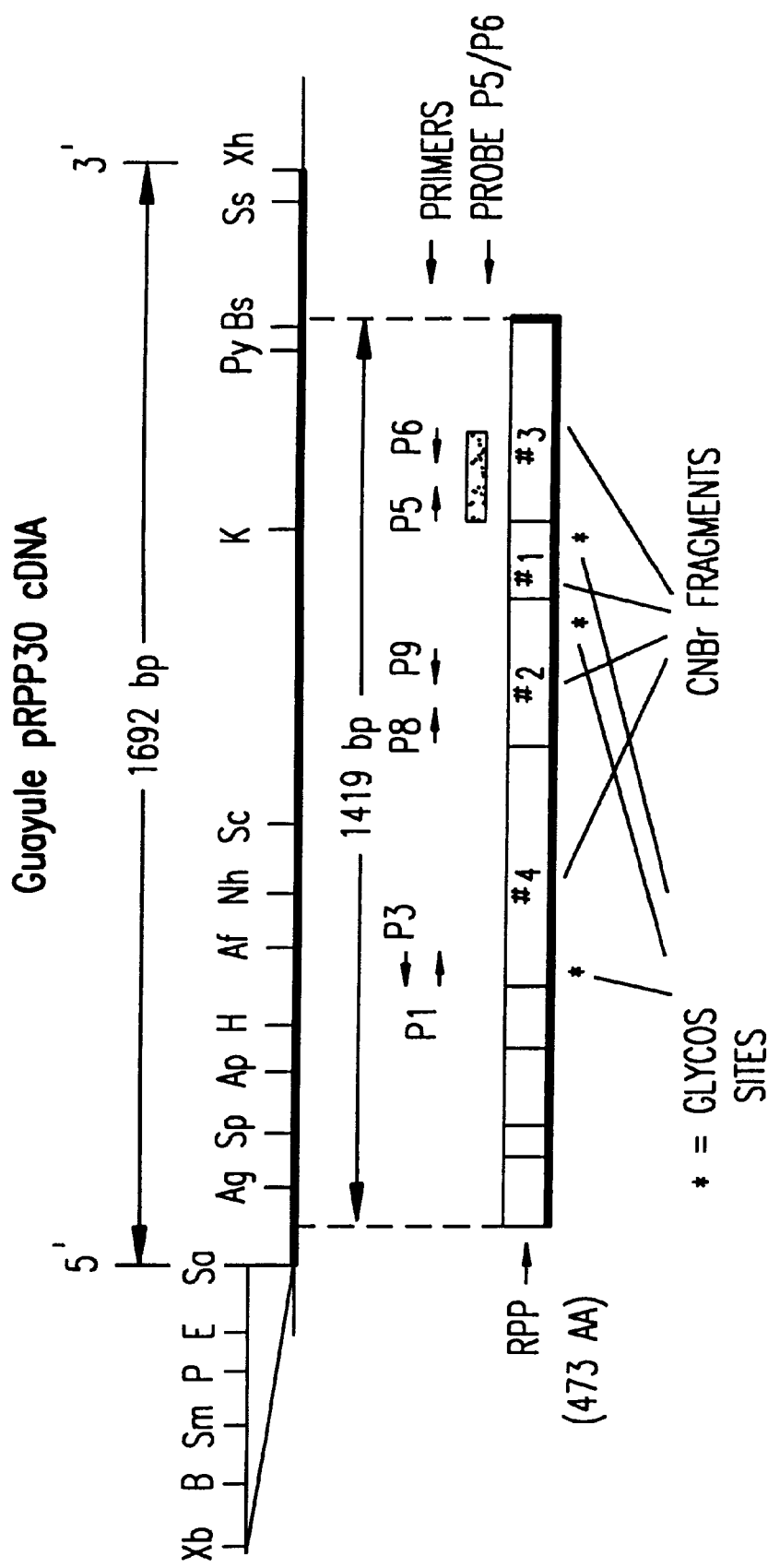

United States Patent [19]
Backhaus et al.

[11] Patent Number: 6,132,711
[45] Date of Patent: Oct. 17, 2000

[54] ENZYMATIC ANTIOXIDANT OF ALLENE OXIDE FOR LIPID PEROXIDATION IN BIOLOGICAL SYSTEMS

[75] Inventors: Ralph A. Backhaus, Phoenix, Ariz.; Zhiqiang Pan, Davis, Calif.; Lisa A. Herickhoff, Fort Collins, Colo.

[73] Assignee: Arizona Board of Regents, Tempe, Ariz.

[21] Appl. No.: 08/896,162

[22] Filed: Jul. 17, 1997

Related U.S. Application Data

[63] Continuation-in-part of application No. 08/863,726, May 27, 1997, abandoned, which is a continuation of application No. 08/240,012, May 9, 1994, Pat. No. 5,633,433, which is a continuation of application No. 08/000,872, Jan. 5, 1993, abandoned, which is a continuation-in-part of application No. 07/687,456, Apr. 17, 1991, abandoned.

[51] Int. Cl.$^7$ .............................. A61K 38/43; C11B 9/00; C08B 3/00; C08B 5/00
[52] U.S. Cl. ........................... 424/94.1; 514/2; 536/23.2; 530/370
[58] Field of Search ................................ 424/94.1; 514/2; 536/23.2; 530/370

[56] References Cited

PUBLICATIONS

Harms et al. The Plant Cell. 1995. vol.7:1645–1654.
Dogru–Abbasoglu et al. Mechanisms of Aging and Development. 1997. vol. 98: 177–180 (abstract).
Song etal. Science. 1991. vol. 253: 781–184.
Tappel Methods of enzymology. 1978. vol. 52: 506–513.
Webster's Ninth New Collegiate Dictionary, 1984, p. 92.
Pan et al., J. Biol. Chem. 270 (15): 8487–8494 (Apr. 14, 1995).
Wengenack TM et al., Brain Res., 754 (1–2): 46–54 (Apr. 18, 1997) (abstract).
Campbell CM et al., Am Heart J., 133 (5): 508–516 (May 1997) (abstract).
Hori Y et al., Japan J. Pharmacol, 74 (1): 99–103 (May 1997) (abstract).

*Primary Examiner*—Elizabeth F. McElwain
*Assistant Examiner*—Ousama M-Faiz Zaghmout
*Attorney, Agent, or Firm*—Baker Botts LLP

[57] ABSTRACT

The present invention relates to the isolation and use of an allene oxide synthase enzyme as an antioxidant of lipid peroxides in biological systems. It is based, at least in part, on the discovery that antioxidation is accomplished enzymatically by RPP, a species of allene oxide synthase, in guayule, and on the discovery that the allene oxide synthase RPP disrupts the chain reaction and propagation steps of lipid peroxidation. The present further invention relates to the use of an allene oxide synthase to result in a time-dependent disappearance of conjugated dienes (i.e. lipid hydroperoxides). The allene oxide synthase rapidly converts free or esterified fatty acid peroxides or hydroperoxides into their corresponding epoxides, which, in turn are converted to ketols. The lipid peroxide and hydroperoxide substrates for this enzyme are known to be toxic to biological organisms and can generate additional peroxides by chain propagation reactions. In the presence of an allene oxide synthase these compounds are rapidly and effectively converted to allene oxides (the epoxide), thus breaking the chain reaction.

2 Claims, 33 Drawing Sheets

CNBr #1

Pro-Leu-Thr-Lys-Ser-Val-Val-Tyr-Glu-Ser-Leu-Arg-Ile-Glu-Pro-Pro-Val

CNBr #2

Met-Glu-Gln-Ala-Glu-Lys-Leu-Gly-Val-Pro-Lys-Asp-Glu-Ala-Val-His-Asn-Ile-Leu-Phe-Ala-Val-Cys-Phe-Asn-Thr-Phe-Gly-Gly-Val-Lys

CNBr #3

Leu-Phe-Gly-Tyr-Gln-Pro-Phe-Ala-Thr-Lys-Asp-Pro-Lys-Val-Phe-Asp-Arg-Pro-Glu-Phe-Val-Pro-Asp-Arg-Phe-Val-Gly-Asp-Gly-Glu-Ala-Leu-Leu-Lys-Tyr

CNBr #4

Leu-Lys-Asn-Ser-Ser-Asn-Arg-Val-Ile-Pro-Gln-Phe-Glu-Thr-Thr-Tyr-Tyr-Glu-Leu-Phe-Glu-Gly-Leu-Glu-Ala

FIG. 1

| | | |
|---|---|---|
| Sequence P5:<br>20-mer | Phe Gly Tyr Gln Pro Phe Ala<br>TTY GGN TAY CAR CYN TTY GC | (sense) |
| Sequence P6:<br>20-mer | GC YTC NCC RTC NCC NAC RAA | (antisense) |
| Sequence P1:<br>17-mer | Ile Pro Gln Phe Glu Thr<br>ATH CYN CAR TTY GAR AC | (sense) |
| Sequence P9:<br>23-mer | TT NAC NCC NCC RAA NGT RTT TAA | (antisense) |
| Sequence P8:<br>20-mer | Met Glu Gln Ala Glu Lys Leu<br>ATG GAR CAR GCN GAR AAR YT | (sense) |
| Sequence P3:<br>17-mer | GT YTC RAA YTG NRG DAT | (antisense) |

FIG. 2A

Sequence P5/6: A PCR amplified 92 bp cDNA sequence for an RPP sequence between P5 and P6 of CNBr fragment #3.

```
92-mer    TTC GGG TAC CAA CCG TTT GCA ACC AAG GAC CCG AAA
          GTA TTT GAC CGA CCT GAG CCT GAG GTC CCT GAT CGG
          TTC GTT GGG GAT GGC GAG GAG GC
```

Sequence P5, P6 and P5/6 code for DNA contained within CNBr fragment #3; sequences P1 and P3 code for DNA contained in CNBr fragment #4; sequence P8 and P9 code for DNA contained in CNBr fragment #2.

Coding redundancies are:

| | | |
|---|---|---|
| N = C, T, A or C | H = A, C or T | S = G or C |
| R = A or G | B = C, G or T | K = G or T |
| Y = C or T | V = A, C or G | W = A or T |
| M = A or C | D = A, G or T | |

FIG. 2B

CTCACATTCAAAACAGTCAAAAC ATG GAC CCA TCG TCT AAA CCC CTC CGT       50
                        Met Asp Pro Ser Ser Lys Pro Leu Arg
                         1                5

GAA ATC CCC GGC TCT TAT GGC ATT CCT TTC TTT CAA CCG ATA AAA       95
Glu Ile Pro Gly Ser Tyr Gly Ile Pro Phe Phe Gln Pro Ile Lys
 10              15              20

GAC CGG TTG GAG TAT TTT TAC GGG ACC GGA GGT CGA GAC GAG TAC      140
Asp Arg Leu Glu Tyr Phe Tyr Gly Thr Gly Gly Arg Asp Glu Tyr
 25              30              35

TTC CGG TCC CGC ATG CAA AAA TAC CAA TCC ACG GTA TTT CGA GCC      185
Phe Arg Ser Arg Met Gln Lys Tyr Gln Ser Thr Val Phe Arg Ala
 40              45              50

AAC ATG CCA CCG GGC CCT TTC GTA AGC AGC AAC CCG AAG GTA ATC      230
Asn Met Pro Pro Gly Pro Phe Val Ser Ser Asn Pro Lys Val Ile
 55              60              65

GTC CTA CTC GAC GCC AAA AGC TTT CCG ATA CTC TTT GAT GTA TCC      275
Val Leu Leu Asp Ala Lys Ser Phe Pro Ile Leu Phe Asp Val Ser
 70              75              80

FIG. 3A

```
AAA GTC GAG AAG AAA GAT TTG TTC ACC GGA ACT TAC ATG CCG TCA   320
Lys Val Glu Lys Lys Asp Leu Phe Thr Gly Thr Tyr Met Pro Ser
 85                      90                  95

ACC AAA CTC ACT GGC GCG TAT CGC GTA CTC TCG TAC CTC GAC CCA   365
Thr Lys Leu Thr Gly Ala Tyr Arg Val Leu Ser Tyr Leu Asp Pro
100                     105                 110

TCC GAA CCT AGA CAT GCT CAA CTT AAG AAC CTC TTG TTC ATG       410
Ser Glu Pro Arg His Ala Gln Leu Lys Asn Leu Leu Phe Met
115                     120                 125

Primer P1
                              --- --- --- --- --- -->
CTT AAA AAT TCA AGC AAC CGA GTC ATC CCA CAG TTT GAA ACC ACT   455
Leu Lys Asn Ser Ser Asn Arg Val Ile Pro Gln Phe Glu Thr Thr
130                     135                 140
 *    *    *    *    *  <--  *    *    *    *    *    *    *    *    *
(CNBr #4)                         Primer P3

TAC ACC GAA CTC TTT GAA GGT CTT GAA GCC GAG CTA GCC AAA AAC   500
Tyr Thr Glu Leu Phe Glu Gly Leu Glu Ala Glu Leu Ala Lys Asn
145                     150                 155
 *    *    *    *    *    *    *    *    *    *    *    *    *    *    *
```

FIG. 3B

```
GGG AAA GCC GCG TTC AAC GAT GTT GGT GAA CAA GCG GCT TTC CGG    545
Gly Lys Ala Ala Phe Asn Asp Val Gly Glu Gln Ala Ala Phe Arg
160                 165                 170

TTT TTG GGC AGG GCT TAT TTT AAC TCG AAC CCG GAA GAA ACC AAA    590
Phe Leu Gly Arg Ala Tyr Phe Asn Ser Asn Pro Glu Glu Thr Lys
175                 180                 185

CTA GGA ACT AGT GCG CCT ACG TTA ATT AGC TCG TGG GTG TTA TTT    635
Leu Gly Thr Ser Ala Pro Thr Leu Ile Ser Ser Trp Val Leu Phe
190                 195                 200

AAT CTT GCC CCC ACG CTC GAC CTC GGA CTT CCG TGG TTC TTG CAG    680
Asn Leu Ala Pro Thr Leu Asp Leu Gly Leu Pro Trp Phe Leu Gln
205                 210                 215

GAA CCT CTT CTA CAC ACT TTC CGA CTG ACT GCG GCG TTC CTG ATT AAG  725
Glu Pro Leu Leu His Thr Phe Arg Leu Thr Ala Ala Phe Leu Ile Lys
220                 225                 230

AGT ACT TAC AAC AAA CTT TAC GAT TAT TTC CAG TCG GTT GCG ACT    770
Ser Thr Tyr Asn Lys Leu Tyr Asp Tyr Phe Gln Ser Val Ala Thr
235                 240                 245
```

FIG. 3C

```
         Primer P8
       |-- --- --- --- -->
CCG GTT ATG GAA CAA GCA GAA AAA TTA GGG GTT CCG AAG GAT GAA    815
Pro Val Met Glu Gln Ala Glu Lys Leu Gly Val Pro Lys Asp Glu
250                 255                 260
  *       *   *                       *               *
        (CNBr #2)

GCT GTG CAC AAT ATC TTA TTC GCG GTT TGC TTC AAT ACT TTT GGT    860
Ala Val His Asn Ile Leu Phe Ala Val Cys Phe Asn Thr Phe Gly
265                 270                 275
  *                   *                   *
                                                  Primer P9
                                              |-- --- --- --|
                                              <--           |
GGT GTT AAG ATC CTC TTC CCG AAT ACA CTC AAA TGG ATC GGA GTT    905
Gly Val Lys Ile Leu Phe Pro Asn Thr Leu Lys Trp Ile Gly Val
280                 285                 290
*   *       *
|           |

GCT GGG GAG AAT TTG CAT ACC CAA TTG GCG GAA GAG ATT AGA GGT    950
Ala Gly Glu Asn Leu His Thr Gln Leu Ala Glu Glu Ile Arg Gly
295                 300                 305

GCT ATA AAA TCA TAC GGG GAC GGT AAC GTG ACG CTG GAA GCA ATC    995
Ala Ile Lys Ser Tyr Gly Asp Gly Asn Val Thr Leu Glu Ala Ile
310                 315                 320
```

FIG. 3D

```
GAG CAG ATG CCG TTG ACG AAG TCA GTG TAC GAG TCC CTC AGG    1040
Glu Gln Met Pro Leu Thr Lys Ser Val Val Tyr Glu Ser Leu Arg
325                     330                 335
 *   *   *   *   *   *   *   *   *   *   *   *   *   *   *
        (CNBr #1)

ATT GAA CCA CCA GTG CCT CCG CAA TAT GGA AAA GCC AAA AGC AAC    1085
Ile Glu Pro Pro Val Pro Pro Gln Tyr Gly Lys Ala Lys Ser Asn
340                     345                 350
 *   *   *   *   *   *   *   *   *   *   *   *   *   *   *

TTT ACC ATA GAG TCA CAC GAC GCC ACT TTC GAA GTC AAA AAA GGA    1130
Phe Thr Ile Glu Ser His Asp Ala Thr Phe Glu Val Lys Lys Gly
355                     360                 365
                    Primer P5
                --- --- --- --- -->
 *   *   *   *   *   *   *   *   *   *   *   *   *   *   *

GAA ATG TTA TTC GGG TAC TTT CAA CCG TTT GCA ACC AAG GAC CCG AAA    1175
Glu Met Leu Phe Gly Tyr Phe Gln Pro Phe Ala Thr Lys Asp Pro Lys
370                     375                 380
 *   *   *   *   *   *   *   *   *   *   *   *   *   *   *   *
        (CNBr #3)
```

FIG. 3E

```
GTA TTT GAC CGA CCT GAG GAG TTT GTC CCT GAT CGG TTC GTT GGG   1220
Val Phe Asp Arg Pro Glu Glu Phe Val Pro Asp Arg Phe Val Gly
385                     390                 395
 *   *   *   *   *   *   *   *   *   *   * <-- ---
                                                 --- ---

GAT GGC GAG AGT GCA TTG TTG AAG TAC GTA TGG TCT AAT GGG CCG   1265
Asp Gly Glu Ser Ala Leu Leu Lys Tyr Val Trp Ser Asn Gly Pro
400                     405                 410
 *   *   ---  *   *   *   *   *   *   *
         --- 
         Primer P6

GAG ACA GAG AGT CCG ACA GTT GAA AAT AAA CAA TGT GCC GGA AAA   1310
Glu Thr Glu Ser Pro Thr Val Glu Asn Lys Gln Cys Ala Gly Lys
415                     420                 425

GAC TTT GTC GTG CTT ATA ACG AGG TTG TTT GTC ATT GAA CTT TTC   1355
Asp Phe Val Val Leu Ile Thr Arg Leu Phe Val Ile Glu Leu Phe
430                     435                 440

CGG CGA TAT GAC TCT TTT GAA ATC GAA TTA GGC GAG TCT CCT TTG   1400
Arg Arg Tyr Asp Ser Phe Glu Ile Glu Leu Gly Glu Ser Pro Leu
445                     450                 455

FIG. 3F
```

```
GGT GCA GCT GTC ACA CTT ACG TTC CTG AAG AGA GCT AGT ATA TGA   1445
Gly Ala Ala Val Thr Leu Thr Phe Leu Lys Arg Ala Ser Ile
460                     465                     470

TTGCAGCCAT AACTAGTTAC CCTGTACTAG CACGTTAGTA AAATGATGTT         1495

TGATATGTTT TTCAAGTAAA TATAAAAATA AAGTAATAAA AAAGGGATGT         1545

GTATATGGGG AGGGGTGTGG GAGGTCAGGA TCAAGTATGT ATCAAGGTTG         1595

TTTGTATTAT TCGTGCTATG AATAAGTGTT GAATTTGCAG TTCAAGAGCA         1645

TAAAATAAAT ATTGTTTCAC AAAATTTAGA AAAAAAAAA AAAAAAA            1692
```

FIG. 3G

```
AOS  51 PIKIPGITSQPPPSSDETTLPIRQIPGDYGLPGIGPIQDRLDYFYN.QGR  99
        |... |:|:|||.||:| :.||.|||:|||. .||
RPP   1 ..............MDPSSKPLREIPGSYGIPFFQPIKDRLEYFYGTGGR  36

AOS 100 EEFFKSRLQKYKSTVYRANMPPGPFIASNPRVIVLLDAKSFPVLFDMSKV 149
        :|:|:||:|||.|||:||||||||||..|||:|||||||||||:|||.|||
RPP  37 DEYFRSRMQKYQSTVFRANMPPGPFVSSNPKVIVLLDAKSFPILFDVSKV  86

AOS 150 EKKDLFTGTYMPSTELTGGYRILSYLDPSEPNHTKLKQLLFNLIKNRRDY 199
        |||||||||||||.|||.||:||||||||||.|..||.||| ::||..:
RPP  87 EKKDLFTGTYMPSTKLTGAYRVLSYLDPSEPRHAQLKNLLFFMLKNSSNR 136

AOS 200 VIPEFSSSFTDLCEVVEYDLATKGKAAFNDPAEQAAFNFLSRAFFGVKPI 249
        |||:|...:|:| |..| :||..|||||||.:|||||.||:||:|. .|
RPP 137 VIPQFETTYTELFEGLEAELAKNGKAAFNDVGEQAAFRFLGRAYFNSNPE 186

AOS 250 DTPLGKDAPSLISKWVLFNLAPILSVGLPKEVEEATLHSVRLPPLLVQND 299
        :|.||..||.|||.||||||||.|.:|||. ::|: ||..|||::|:...
RPP 187 ETKLGTSAPTLISSWVLFNLAPTLDLGLPWFLQEPLLHTFRLPAFLIKST 236

AOS 300 YHRLYEFFTSAAGSVLDEAEQSGISRDEACHNILFAVCFNSWGGFKILFP 349
        |::||::| |.|..|:::||. |:.:|||.||||||||||.:||.|||||
RPP 237 YNKLYDYFQSVATPVMEQAEKLGVPKDEAVHNILFAVCFNTFGGVKILFP 286

AOS 350 SLMKWIGRAGLELHTKLAQEIRSAIQSTGGGKVTMAAMEQMPLMKSVVYE 399
        . :|||| || :|||.||:|||:||.| |:|.||:..|:||||| ||||||
RPP 287 NTLKWIGVAGENLHTQLAEEIRGAIKSYGDGNVTLEAIEQMPLTKSVVYE 336

AOS 400 TLRIEPPVALQYGKAKKDFILESHEAAYQVKEGEMLFGYQPFATKDPKIF 449
        .|||||||: |||||||.:|.:|||:|.::||.||||||||||||||||:|
RPP 337 SLRIEPPVPPQYGKAKSNFTIESHDATFEVKKGEMLFGYQPFATKDPKVF 386

AOS 450 DRPEEFVADRFVGEGVKLMEYVMWSNGPETETPSVANKQCAGKDFVVMAA 499
        ||||||:|||||:| |:.|| |||||||.|.|.|||||||||: .
RPP 387 DRPEEFVPDRFVGDGEALLKYVWWSNGPETESPTVENKQCAGKDFVVLIT 436

AOS 500 RLFVVELFKRYDSFDIEVGTSSLGASITLTSLKRSTF 536
        ||||:|||:||||||:|.|.|||.:|||  |||  |||...:
RPP 437 RLFVIELFRRYDSFEIELGESPLGAAVTLTFLKRASI 473
```

FIG. 5

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
      (A) LENGTH: 17 amino acid residues
      (B) TYPE: amino acid
      (D) TOPOLOGY: linear (ii) MOLECULE TYPE:
      (A) DESCRIPTION: CNBr peptide #1 of guayule RPP -continued

```
    (iii) HYPOTHETICAL:  no (iv) ANTI-SENSE:    no (v) FRAGMENT TYPE: internal fragment (vi) ORIGINAL SOURCE:
          (A) ORGANISM:  Parthenium argentatum
          (B) STRAIN:    11591
          (D) DEVELOPMENTAL STAGE:  cortex from secondary
              growth of stems
          (F) TISSUE TYPE:  Stembark (ix) FEATURE:
          (A) NAME/KEY: CNBr #1 of guayule RPP
          (B) LOCATION: internal region of RPP
          (C) IDENTIFICATION METHOD:  by experiment using
              an amino acid sequenator
          (C) OTHER INFORMATION: RPP is the rubber particle
              protein bound to natural rubber and is
              essential for rubber formation in guayule.

(xi) SEQUENCE DESCRIPTION: SEQ ID NO: 1:

Pro Leu Thr Lys Ser Val Val Tyr Glu Ser Leu Arg Ile Glu Pro Pro Val
                 5                  10                  15

(2) INFORMATION FOR SEQ ID NO: 2:

(i) SEQUENCE CHARACTERISTICS:
          (A) LENGTH: 31 amino acid residues
          (B) TYPE: amino acid
          (D) TOPOLOGY: linear (ii) MOLECULE TYPE:
          (A) DESCRIPTION:  CNBr peptide #2 of guayule RPP (iii) HYPOTHETICAL:  no (iv) ANTI-SENSE:    no (v) FRAGMENT TYPE: internal fragment (vi) ORIGINAL SOURCE:
          (A) ORGANISM:  Parthenium argentatum
          (B) STRAIN:    11591
          (D) DEVELOPMENTAL STAGE:  cortex from secondary
              growth of stems
          (F) TISSUE TYPE:  Stembark (ix) FEATURE:
          (A) NAME/KEY: CNBr #2 of guayule RPP
          (B) LOCATION: internal region of RPP
          (C) IDENTIFICATION METHOD:  by experiment using
              an amino acid sequenator
          (C) OTHER INFORMATION: RPP is the rubber particle
              protein bound to natural rubber and is
              essential for rubber formation in guayule.

(xi) SEQUENCE DESCRIPTION: SEQ ID NO: 2:

Met Glu Gln Ala Glu Lys Leu Gly Val Pro Lys Asp Glu Ala Val
                 5                  10                  15

His Asn Ile Leu Phe Ala Val Cys Phe Asn Thr Phe Gly Gly Val Lys
                20                  25                  30

(2) INFORMATION FOR SEQ ID NO: 3:

(i) SEQUENCE CHARACTERISTICS:
          (A) LENGTH: 36 amino acid residues
          (B) TYPE: amino acid
          (D) TOPOLOGY: linear (ii) MOLECULE TYPE:
          (A) DESCRIPTION:  CNBr peptide #3 of guayule RPP
```

```
        (iii) HYPOTHETICAL:  no (iv) ANTI-SENSE:    no (v) FRAGMENT TYPE: internal fragment (vi) ORIGINAL SOURCE:
              (A) ORGANISM:  Parthenium argentatum
              (B) STRAIN:    11591
              (D) DEVELOPMENTAL STAGE:  cortex from secondary
                   growth of stems
              (F) TISSUE TYPE:  Stembark (ix) FEATURE:
              (A) NAME/KEY: CNBr #3 of guayule RPP
              (B) LOCATION: internal region of RPP
              (C) IDENTIFICATION METHOD:  by experiment using
                   an amino acid sequenator
              (C) OTHER INFORMATION: RPP is the rubber particle
                   protein bound to natural rubber and is
                   essential for rubber formation in guayule.

(xi) SEQUENCE DESCRIPTION: SEQ ID NO: 3:

Leu Phe Gly Tyr Gln Pro Phe Ala Thr Lys Asp Pro Lys Val Phe
                  5                  10                  15

Asp Arg Pro Glu Glu Phe Val Pro Asp Arg Phe Val Gly Asp Gly
                 20                  25                  30

Glu Ala Leu Leu Lys Tyr
                 35

(2) INFORMATION FOR SEQ ID NO: 4:

(i) SEQUENCE CHARACTERISTICS:
          (A) LENGTH: 25 amino acid residues
          (B) TYPE: amino acid
          (D) TOPOLOGY: linear (ii) MOLECULE TYPE:
          (A) DESCRIPTION:  CNBr peptide #4 of guayule RPP (iii) HYPOTHETICAL:  no (iv) ANTI-SENSE:    no (v) FRAGMENT TYPE: internal fragment (vi) ORIGINAL SOURCE:
          (A) ORGANISM:  Parthenium argentatum
          (B) STRAIN:    11591
          (D) DEVELOPMENTAL STAGE:  cortex from secondary
               growth of stems
          (F) TISSUE TYPE:  Stembark (ix) FEATURE:
          (A) NAME/KEY: CNBr #4 of guayule RPP
          (B) LOCATION: internal region of RPP
          (C) IDENTIFICATION METHOD:  by experiment using
               an amino acid sequenator
          (D) OTHER INFORMATION: RPP is the rubber particle
               protein bound to natural rubber and is
               essential for rubber formation in guayule.

(xi) SEQUENCE DESCRIPTION: SEQ ID NO: 4:

Leu Lys Asn Ser Ser Asn Arg Val Ile Pro Gln Phe Glu Thr Thr
                  5                  10                  15

Tyr Tyr Glu Leu Phe Glu Gly Leu Glu Ala
                 20                  25

(2) INFORMATION FOR SEQ ID NO: 5:

(i) SEQUENCE CHARACTERISTICS:
          (A) LENGTH: 20 bases
```

(B) TYPE: nucleic acid
            (C) STRANDEDNESS: single
            (D) TOPOLOGY: linear (ii) MOLECULE TYPE:
            (A) DESCRIPTION: Oligonucleotide sequence deduced
                from RPP amino acid sequence (iii) HYPOTHETICAL: no (iv) ANTI-SENSE: no (vi) ORIGINAL SOURCE:
            (A) ORGANISM: Parthenium argentatum
            (B) STRAIN: 11591
            (D) DEVELOPMENTAL STAGE: cortex from secondary
                growth of stems
            (F) TISSUE TYPE: Stembark (ix) FEATURE:
            (A) NAME/KEY: P5 primer, sense strand for CNBr
                peptide #3 (SEQ. ID No. 3)
            (D) OTHER INFORMATION: RPP is the rubber particle
                protein bound to natural rubber in guayule and
                is essential for rubber formation in guayule (xi) SEQUENCE DESCRIPTION: SEQ ID NO: 5:

TTY GGN TAY CAR CYN TTY GC                                              20
Phe Gly Tyr Gln Pro Phe Ala
              5

(2) INFORMATION FOR SEQ ID NO: 6:

(i) SEQUENCE CHARACTERISTICS:
            (A) LENGTH: 20 bases
            (B) TYPE: nucleic acid
            (C) STRANDEDNESS: single
            (D) TOPOLOGY: linear (ii) MOLECULE TYPE:
            (A) DESCRIPTION: Oligonucleotide sequence deduced
                from RPP amino acid sequence (iii) HYPOTHETICAL: no (iv) ANTI-SENSE: no (vi) ORIGINAL SOURCE:
            (A) ORGANISM: Parthenium argentatum
            (B) STRAIN: 11591
            (D) DEVELOPMENTAL STAGE: cortex from secondary
                growth of stems
            (F) TISSUE TYPE: Stembark (ix) FEATURE:
            (A) NAME/KEY: P6 primer, sense strand for CNBr
                peptide #3 (SEQ ID No. 3)
            (D) OTHER INFORMATION: RPP is the rubber particle
                protein bound to natural rubber in guayule and
                is essential for rubber formation in guayule (xi) SEQUENCE DESCRIPTION: SEQ ID NO: 6:

GCYTCNCCRT CNCCNACRAA                                                   20

(2) INFORMATION FOR SEQ ID NO: 7:

(i) SEQUENCE CHARACTERISTICS:
            (A) LENGTH: 17 bases
            (B) TYPE: nucleic acid
            (C) STRANDEDNESS: single
            (D) TOPOLOGY: linear (ii) MOLECULE TYPE:
            (A) DESCRIPTION: Oligonucleotide sequence deduced
                from RPP amino acid sequence

```
    (iii) HYPOTHETICAL: no (iv) ANTI-SENSE:   no (vi) ORIGINAL SOURCE:
         (A) ORGANISM: Parthenium argentatum
         (B) STRAIN:    11591
         (D) DEVELOPMENTAL STAGE: cortex from secondary
             growth of stems
         (F) TISSUE TYPE: Stembark (ix) FEATURE:
         (A) NAME/KEY: P1 primer, sense strand for CNBr
             peptide #4 (SEQ. ID No. 4)
         (D) OTHER INFORMATION:  RPP is the rubber particle
             protein bound to natural rubber in guayule and
             is essential for rubber formation in guayule (xi) SEQUENCE DESCRIPTION: SEQ ID NO: 7:

ATH CYN CAR TTY GAR AC                                                17
Ile Pro Gln Phe Glu Thr
              5

(2) INFORMATION FOR SEQ ID NO: 8:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE:
         (A) DESCRIPTION:  Oligonucleotide sequence deduced
             from RPP amino acid sequence (iii) HYPOTHETICAL: no (iv) ANTI-SENSE:   no (vi) ORIGINAL SOURCE:
         (A) ORGANISM: Parthenium argentatum
         (B) STRAIN:    11591
         (D) DEVELOPMENTAL STAGE: cortex from secondary
             growth of stems
         (F) TISSUE TYPE: Stembark (ix) FEATURE:
         (A) NAME/KEY: P9 primer, anti-sense strand for CNBr
             peptide #2 (SEQ. ID No. 2)
         (D) OTHER INFORMATION:  RPP is the rubber particle
             protein bound to natural rubber in guayule and
             is essential for rubber formation in guayule (xi) SEQUENCE DESCRIPTION: SEQ ID NO: 8:

TTNACNCCNC CRAANGTRTT TAA                                             23

(2) INFORMATION FOR SEQ ID NO: 9:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE:
         (A) DESCRIPTION:  Oligonucleotide sequence deduced
             from RPP amino acid sequence (iii) HYPOTHETICAL: no (iv) ANTI-SENSE:   no (vi) ORIGINAL SOURCE:
         (A) ORGANISM:  Parthenium argentatum
```

```
            (B) STRAIN:    11591
            (D) DEVELOPMENTAL STAGE:  cortex from secondary
                growth of stems
            (F) TISSUE TYPE:  Stembark (ix) FEATURE:
            (A) NAME/KEY: P8 primer, sense strand for CNBr
                peptide #2 (SEQ. ID No. 2)
            (D) OTHER INFORMATION:   RPP is the rubber particle
                protein bound to natural rubber in guayule and
                is essential for rubber formation in guayule (xi) SEQUENCE DESCRIPTION: SEQ ID NO: 9:

ATG GAR CAR GCN GAR AAR  YT                                              20
Met Glu Gln Ala Gln Lys Leu
                5

(2) INFORMATION FOR SEQ ID NO: 10:

(i) SEQUENCE CHARACTERISTICS:
            (A) LENGTH: 17 bases
            (B) TYPE: nucleic acid
            (C) STRANDEDNESS:  single
            (D) TOPOLOGY: linear (ii) MOLECULE TYPE:
            (A) DESCRIPTION:  Oligonucleotide sequence deduced
                from RPP amino acid sequence (iii) HYPOTHETICAL:  no (iv) ANTI-SENSE:    yes (vi) ORIGINAL SOURCE:
            (A) ORGANISM:  Parthenium argentatum
            (B) STRAIN:    11591
            (D) DEVELOPMENTAL STAGE:  cortex from secondary
                growth of stems
            (F) TISSUE TYPE:  Stembark (ix) FEATURE:
            (A) NAME/KEY: P3 primer, sense strand for CNBr
                peptide #4 (SEQ. ID No. 4)
            (D) OTHER INFORMATION:   RPP is the rubber particle
                protein bound to natural rubber in guayule and
                is essential for rubber formation in guayule (xi) SEQUENCE DESCRIPTION: SEQ ID NO: 10:

GTYTCRAAYT GNRGDAT                                                       17

(2) INFORMATION FOR SEQ ID NO: 11:

(i) SEQUENCE CHARACTERISTICS:
            (A) LENGTH: 92 base pairs
            (B) TYPE: nucleic acid
            (C) STRANDEDNESS:  double
            (D) TOPOLOGY: linear (ii) MOLECULE TYPE:
            (A) DESCRIPTION:  PCR amplified cDNA from mRNA (iii) HYPOTHETICAL:  no (iv) ANTI-SENSE:    no (vi) ORIGINAL SOURCE:
            (A) ORGANISM:  Parthenium argentatum
            (B) STRAIN:    11591
            (D) DEVELOPMENTAL STAGE:  cortex from secondary
                growth of stems
            (F) TISSUE TYPE:  Stembark (ix) FEATURE:
            (A) NAME/KEY: P5/6, a PCR amplified cDNA of CNBr
                peptide #3 (SEQ ID No: 3) using P5 and P6
``` primers (SEQ ID Nos: 5 and 6)
        (D) OTHER INFORMATION:  RPP is the rubber particle
            protein bound to natural rubber in guayule and
            is essential for rubber formation in guayule (xi) SEQUENCE DESCRIPTION: SEQ ID NO: 11:

```
TTC GGG TAC CAA CCG TTT GCA ACC AAG GAC CCG AAA GTA TTT          42
Phe Gly Tyr Gln Pro Phe Ala Thr Lys Asp Pro Lys Val Phe
            5                  10

GAC CGA CCT GAG GAG TTT GTC CCT GAT CGG TTC GTT GGG GAT          84
Asp Arg Pro Glu Glu Phe Val Pro Asp Arg Phe Val Gly Asp
15                  20                  25

GGC GAG GC                                                       92
Gly Glu Ala
    30
```

(2) INFORMATION FOR SEQ ID NO: 12:

(i) SEQUENCE CHARACTERISTICS:
        (A) LENGTH: 1692 base pairs
        (B) TYPE: nucleic acid
        (C) STRANDEDNESS: double
        (D) TOPOLOGY: linear (ii) MOLECULE TYPE:
        (A) DESCRIPTION:  cDNA from mRNA (iii) HYPOTHETICAL: no (iv) ANTI-SENSE:    no (vi) ORIGINAL SOURCE:
        (A) ORGANISM: Parthenium argentatum
        (B) STRAIN:   11591
        (D) DEVELOPMENTAL STAGE:  cortex from secondary
            growth of stems
        (F) TISSUE TYPE:  Stembark (vii) IMMEDIATE SOURCE:
        (A) LIBRARY: Lambda ZAP cDNA library of guayule
            stembark mRNA
        (B) CLONE: pRPP30

(ix) FEATURE:
        (A) NAME/KEY: pRPP30, a guayule RPP gene
        (C) IDENTIFICATION METHOD:  by similarity with
            known RPP amino acid sequences (SEQ ID Nos: 1,
            2, 3 and 4)
        (D) OTHER INFORMATION:  Codes for the entire amino
            acid sequence of RPP which is 473 amino acids
            long. RPP is the rubber particle protein which
            is essential for rubber formation in guayule.

(xi) SEQUENCE DESCRIPTION: SEQ ID NO: 12:

```
CTCACATTCA AAACAGTCAA AAC ATG GAC CCA TCG TCT AAA CCC CTC CGT     50
                        Met Asp Pro Ser Ser Lys Pro Leu Arg
                                          5

GAA ATC CCC GGC TCT TAT GGC ATT CCT TTC TTT CAA CCG ATA AAA      95
Glu Ile Pro Gly Ser Tyr Gly Ile Pro Phe Phe Gln Pro Ile Lys
10                  15                  20

GAC CGG TTG GAG TAT TTT TAC GGG ACC GGA GGT CGA GAC GAG TAC     140
Asp Arg Leu Glu Tyr Phe Tyr Gly Thr Gly Gly Arg Asp Glu Tyr
25                  30                  35

TTC CGG TCC CGC ATG CAA AAA TAC CAA TCC ACG GTA TTT CGA GCC     185
Phe Arg Ser Arg Met Gln Lys Tyr Gln Ser Thr Val Phe Arg Ala
40                  45                  50

AAC ATG CCA CCG GGC CCT TTC GTA AGC AGC AAC CCG AAG GTA ATC     230
Asn Met Pro Pro Gly Pro Phe Val Ser Ser Asn Pro Lys Val Ile
55                  60                  65
```

```
GTC CTA CTC GAC GCC AAA AGC TTT CCG ATA CTC TTT GAT GTA TCC        275
Val Leu Leu Asp Ala Lys Ser Phe Pro Ile Leu Phe Asp Val Ser
 70              75                  80

AAA GTC GAG AAG AAA GAT TTG TTC ACC GGA ACT TAC ATG CCG TCA        320
Lys Val Glu Lys Lys Asp Leu Phe Thr Gly Thr Tyr Met Pro Ser
 85              90                  95

ACC AAA CTC ACT GGC GCG TAT CGC GTA CTC TCG TAC CTC GAC CCA        365
Thr Lys Leu Thr Gly Ala Tyr Arg Val Leu Ser Tyr Leu Asp Pro
100             105                 110

TCC GAA CCT AGA CAT GCT CAA CTT AAG AAC CTC TTG TTC TTC ATG        410
Ser Glu Pro Arg His Ala Gln Leu Lys Asn Leu Leu Phe Phe Met
115             120                 125

CTT AAA AAT TCA AGC AAC CGA GTC ATC CCA CAG TTT GAA ACC ACT        455
Leu Lys Asn Ser Ser Asn Arg Val Ile Pro Gln Phe Glu Thr Thr
130             135                 140

TAC ACC GAA CTC TTT GAA GGT CTT GAA GCC GAG CTA GCC AAA AAC        500
Tyr Thr Glu Leu Phe Glu Gly Leu Glu Ala Glu Leu Ala Lys Asn
145             150                 155

GGG AAA GCC GCG TTC AAC GAT GTT GGT GAA CAA GCG GCT TTC CGG        545
Gly Lys Ala Ala Phe Asn Asp Val Gly Glu Gln Ala Ala Phe Arg
160             165                 170

TTT TTG GGC AGG GCT TAT TTT AAC TCG AAC CCG GAA GAA ACC AAA        590
Phe Leu Gly Arg Ala Tyr Phe Asn Ser Asn Pro Glu Glu Thr Lys
175             180                 185

CTA GGA ACT AGT GCG CCT ACG TTA ATT AGC TCG TGG GTG TTA TTT        635
Leu Gly Thr Ser Ala Pro Thr Leu Ile Ser Ser Trp Val Leu Phe
190             195                 200

AAT CTT GCC CCC ACG CTC GAC CTC GGA CTT CCG TGG TTC TTG CAG        680
Asn Leu Ala Pro Thr Leu Asp Leu Gly Leu Pro Trp Phe Leu Gln
205             210                 215

GAA CCT CTT CTA CAC ACT TTC CGA CTG CCG GCG TTC CTG ATT AAG        725
Glu Pro Leu Leu His Thr Phe Arg Leu Pro Ala Phe Leu Ile Lys
220             225                 230

AGT ACT TAC AAC AAA CTT TAC GAT TAT TTC CAG TCG GTT GCG ACT        770
Ser Thr Tyr Asn Lys Leu Tyr Asp Tyr Phe Gln Ser Val Ala Thr
235             240                 245

CCG GTT ATG GAA CAA GCA GAA AAA TTA GGG GTT CCG AAG GAT GAA        815
Pro Val Met Glu Gln Ala Glu Lys Leu Gly Val Pro Lys Asp Glu
250             255                 260

GCT GTG CAC AAT ATC TTA TTC GCG GTT TGC TTC AAT ACT TTT GGT        860
Ala Val His Asn Ile Leu Phe Ala Val Cys Phe Asn Thr Phe Gly
265             270                 275

GGT GTT AAG ATC CTC TTC CCG AAT ACA CTC AAA TGG ATC GGA GTT        905
Gly Val Lys Ile Leu Phe Pro Asn Thr Leu Lys Trp Ile Gly Val
280             285                 290

GCT GGT GAG AAT TTG CAT ACC CAA TTG GCG GAA GAG ATT AGA GGT        950
Ala Gly Glu Asn Leu His Thr Gln Leu Ala Glu Glu Ile Arg Gly
295             300                 305

GCT ATA AAA TCA TAC GGG GAC GGT AAC GTG ACG CTG GAA GCA ATC        995
Ala Ile Lys Ser Tyr Gly Asp Gly Asn Val Thr Leu Glu Ala Ile
310             315                 320

GAG CAG ATG CCG TTG ACG AAG TCA GTG GTG TAC GAG TCC CTC AGG       1040
Glu Gln Met Pro Leu Thr Lys Ser Val Val Tyr Glu Ser Leu Arg
325             330                 335

ATT GAA CCA CCA GTG CCT CCG CAA TAT GGA AAA GCC AAA AGC AAC       1085
Ile Glu Pro Pro Val Pro Pro Gln Tyr Gly Lys Ala Lys Ser Asn
340             345                 350

TTT ACC ATA GAG TCA CAC GAC GCC ACT TTC GAA GTC AAA AAA GGA       1130
Phe Thr Ile Glu Ser His Asp Ala Thr Phe Glu Val Lys Lys Gly
355             360                 365
```

```
GAA ATG TTA TTC GGG TAC CAA CCG TTT GCA ACC AAG GAC CCG AAA          1175
Glu Met Leu Phe Gly Tyr Gln Pro Phe Ala Thr Lys Asp Pro Lys
370                 375                 380

GTA TTT GAC CGA CCT GAG GAG TTT GTC CCT GAT CGG TTC GTT GGG          1220
Val Phe Asp Arg Pro Glu Glu Phe Val Pro Asp Arg Phe Val Gly
385                 390                 395

GAT GGC GAG GCA TTG TTG AAG TAC GTA TGG TGG TCT AAT GGG CCG          1265
Asp Gly Glu Ala Leu Leu Lys Tyr Val Trp Trp Ser Asn Gly Pro
400                 405                 410

GAG ACA GAG AGT CCG ACA GTT GAA AAT AAA CAA TGT GCC GGA AAA          1310
Glu Thr Glu Ser Pro Thr Val Glu Asn Lys Gln Cys Ala Gly Lys
415                 420                 425

GAC TTT GTC GTG CTT ATA ACG AGG TTG TTT GTC ATT GAA CTT TTC          1355
Asp Phe Val Val Leu Ile Thr Arg Leu Phe Val Ile Glu Leu Phe
430                 435                 440

CGG CGA TAT GAC TCT TTT GAA ATC GAA TTA GGC GAG TCT CCT TTG          1400
Arg Arg Tyr Asp Ser The Glu Ile Glu Leu Gly Glu Ser Pro Leu
445                 450                 455

GGT GCA GCT GTC ACA CTT ACG TTC CTG AAG AGA GCT AGT ATA TGA          1445
Gly Ala Ala Val Thr Leu Thr Phe Leu Lys Arg Ala Ser Ile
460                 465                 470

TTGCAGCCAT AACTAGTTAC CCTGTACTAG CACGTTAGTA AAATGATGTT               1495

TGATATGTTT TTCAAGTAAA TATAAAAATA AAGTAATAAA AAAGGGATGT               1545

GTATATGGGG AGGGGTGTGG GAGGTCAGGA TCAAGTATGT ATCAAGGTTG               1595

TTTGTATTAT TCGTGCTATG AATAAGTGTT GAATTTGCAG TTCAAGAGCA               1645

TAAAATAAAT ATTGTTTCAC AAAATTTAGA AAAAAAAAA AAAAAAA                   1692
```

ENZYMATIC ANTIOXIDANT OF ALLENE OXIDE FOR LIPID PEROXIDATION IN BIOLOGICAL SYSTEMS

CROSS-REFERENCE TO RELATED APPLICATIONS

This application is a continuation-in-part of U.S. patent application Ser. No. 08/863,726, filed May 27, 1997, now abandoned, which is a continuation of U.S. patent application Ser. No. 08/240,012, filed May 9, 1994, issued as U.S. Pat. No. 5,633,433, on May 27, 1997, which is a continuation of U.S. patent application Ser. No. 08/000,872, filed Jan. 5, 1993, now abandoned, which is a continuation-in-part of U.S. patent application Ser. No. 07/687,456, filed Apr. 17, 1991, now abandoned.

STATEMENT REGARDING FEDERALLY SPONSORED RESEARCH

The invention described herein was funded in part by a grant from the National Science Foundation, namely, MCB-92-20417. The United States Government may have certain rights under the invention.

1. INTRODUCTION

The present invention relates generally to bioengineering and more particularly to the isolation and elucidation of a guayule rubber particle protein (RPP) gene, the DNA template therefor, and the means, methods and processes to replicate the DNA clone of the guayule RPP gene in homologous or heterologous host cells and organisms. The invention relates also to the use of the RPP gene and its protein to stimulate rubber biosynthesis. RPP is a member of a family of enzymes categorized as allene oxide synthases.

According to a first embodiment of the invention, a recombinant vector containing cDNA encoding guayule RPP is transferred to a prokaryotic or eukaryotic host cell or organism wherein the RPP cDNA, under the control of an appropriate promoter sequence, is expressed to produce functional RPP. The recombinant RPP may then be used for rubber biosynthesis.

In another series of nonlimiting embodiments, the present invention relates to the use of enzymes of the allene oxide synthase family, such as RPP, as antioxidants of lipid peroxides in biological systems, such as animals, plants and insects. Such embodiments are based, at least in part, on the discovery that RPP, by virtue of its allene oxide synthase activity, functions as an antioxidant, causing the time-dependent disappearance of conjugated dienes (i.e. lipid hydroperoxides). The enzymatic activity of allene oxide synthases as antioxidants for lipid peroxidation in biological systems has never before been described.

2. BACKGROUND OF THE INVENTION

Rubber is found in more than two thousand plant species, but is limited to only a few plant families (See Backhaus, Israel J. Bot., 34:283–293 (1985); Archer et al., Chemistry and Physics of Rubber-like Substances, Bateman, L. ed., pp 41–72, MacLaren, London (1963)). Rubber is a polymer composed of between 320–35,000 isoprene molecules. These are linked by stepwise, head-to-tail, cis-1,4 condensations that form the polyisoprene chains. The stepwise isoprene additions are performed by a prenyltransferase enzyme [E.C. 2.5.1.20] known as rubber transferase (RuT), rubber polymerase and rubber cis, 1-4 polyprenyl transferase. RuT had hiterto been considered to be the sole enzyme responsible for rubber formation in plants (See Backhaus, Israel J. Bot. 34: 283–293 (1985); Berndt, U.S. Government Res. Rep. AD-601, 729 (1963); Archer and Cockbain, Methods in Enzymology, 15:476–480, (1969); Archer and Audley, Advances in Enzymology, 29:221–257, (1967); and Lynen, Rubber Res. Inst. Malaya, 21:(4) 389–406 (1969)). However, according to the present invention it has been discovered that there is another enzyme, known as RPP (for rubber particle protein) that clearly causes polyisoprene biosynthesis when transferred to a foreign host plant, such as tobacco. As set forth herein, RPP, unlike RuT, is not a prenyltransferase but rather functions as an allene oxide synthase (AOS). RPP has properties similar to other members of the class of heme-binding enzymes to which AOS belongs (e.g. cytochrome P450) and is an enzyme needed for rubber biosynthesis. P450 enzymes have never before been implicated in rubber biosynthesis.

The first identification of guayule RPP was made in 1985 (Backhaus and Chandra, in Alcorn, S. and Fangmeier, D. (eds) Proceedings of the 4$^{th}$ International Guayule Conference on Guayule Research and Development, October 16–19, (1985); Backhaus and Bess, in Randall, D. D. et al. (eds) Current Topics in Plant Biochemistry and Physiology, 5:186 (1986)). Subsequent publications described its purification and characterization and suggested a putative role as a prenyltransferase in guayule rubber particles (Backhaus and Bess, in Benedict, C. R. (ed) Biochemistry and Regulation of cis-Polyisoprene in Plants, NSF sponsored workshop publication, p. 204–220 (1986); Cornish and Backhaus, Phytochem. 29:3809–3813 (1990); and Backhaus et al. Phytochem. 30:2493–2497 (1991)). Work by Cornish and Siler demonstrated that RPP-like proteins were also present in Hevea and Ficus (Siler and Cornish, Phytochem. 32: 1097–1102 (1993); Cornish, et al. J. Nat. Rubb. Res. (1994); Cornish, et al., Phytochem. (1994); Siler and Cornish, Phytochem. (1994)). The RPP-like proteins in rubber particles of these other species are likely involved in the same enzymatic reaction as RPP. Reference to another protein isolated from guayule rubber particles was made (Benedict et al., Plant Physiol. 92:816–821 (1990)) which described a prenyltransferase but did not identify that protein as RPP despite prior knowledge by those authors (cf. Benedict, C. R. (ed) Biochemistry and Regulation of cis-Polyisoprene in Plants, NSF sponsored workshop publication, p. 204–220 (1986)) of RPP's existence in guayule rubber particles.

RPP is a membrane glycoprotein having an isoelectric point (pI) of 6.2 (Backhaus et al., Phytochem. 30:2493–2497 (1991)). Prior to the present invention, the molecular weight of RPP was estimated to be 48,500 to 53,000 Daltons as determined by sodium dodecylsulfate polyacrylamide gel electrophoresis (SDS-PAGE). RPP is the most abundant protein of guayule rubber particles (Backhaus et al., Phytochem. 30: 2493–2497 (1991)) and was, therefore, considered to be important for rubber biosynthesis.

Rubber, like polyunsaturated fatty acids (PUFAs), is extremely susceptible to autoxidation by free radicals due to the presence of a double bond in each per 5 carbon isoprene monomer (Brydson, Rubber Chemisty, Applied Science Publishers, Inc., Essex (1978)). In rubber, peroxidation changes the physical properties of elastomers with the net effect being chain scission, and/or cross-linking of polymers. In addition, the formation of volatile oxidation products can also occur (Shelton, Rubber Chem. Tech. 45:359–377 (1972)). For each molecule of peroxide on polyisoprene, one cross-link can be formed (Shelton, Rubber Chem. Tech. 45:359–377 (1972)). In addition, rubber particles contain PUFAs, which are also susceptible to peroxidation and can initiate autoxidation of rubber. An antioxidant effect would therefore be beneficial to rubber synthesis.

There are many ways in which an antioxidant effect may be beneficial to diverse biological systems. Lipid peroxides and hydroperoxides are responsible for numerous disorders, including senescence and aging. Lipid peroxidation in biological systems is a consequence of normal metabolic processes in a cell. Active oxygen species such as hydrogen peroxide and superoxide are generated by free radical mediated processes. These species attack susceptible polyunsaturated lipids to form lipid peroxides, which in turn initiate the peroxidation of adjoining lipids in a chain reaction process. Lipid hydroperoxides are also formed enzymically by lipoxygenase (LOX).

Organisms have developed a number of strategies to overcome the damaging effect of these oxidative attacks. One set of mechanisms involves the production of small antioxidant molecules which scavenge free radicals (i.e. beta carotene) or intervene in the formation of lipid peroxides by a chemical reduction (i.e. alpha tocopherol) to break the chain propagation steps. Cells producing adequate amounts of these compounds keep the lipid peroxides from causing cell damage. Another mechanism involves the production of antioxidant enzymes which disrupt various steps of oxidative reactions. Among the enzymes currently known to be involved in these processes are superoxide dismutase (SOD), catalase, ascorbate perioxidase and glutathione peroxidase. For example, the over expression of chloroplast-activated Cu/Zn superoxide dismutase (SOD) acts as an antioxidant, increasing the resistance to oxidative stress in transgenic tobacco plants (Gupta et al. Proc. Nat'l Acad. Sci. USA 90:1629–1633 (1993)). Gupta used a cell leakage analysis to measure cellular damage of leaf disks of transgenic SOD and untransformed cv. Xanthi plants by measurement of the percent solute leakage in treated tissues compared with autoclaved tissues.

Antioxidants, such as beta-carotene, SOD, allopurinol, and catalase, have been used in treating ischemia following surgery or injury in biological organisms. (Konovalova et al., Arkh. Patol. 51(6): 19–24 (1989) (Abstract); Minor et al., Surg. Today 23(8): 728–732 (1993) (Abstract); Maksimenko et al., Eksp. Kin. Farmakol. 56(5): 14–18 (1993) (Abstract); Kloner, Circ. Res. 64:(1): 86–96 (1989) (Abstract); Nayak et al., Invest. Ophthalmol. Vis. Sci. 34(6): 2018–2022 (1993) (Abstract); Baker et al., Ann. Surg. 202(5): 628–641 (1985) (Abstract); Gross et al., Am. J. Physiol. 250(3Pt.2): H372–H377 (1986) (Abstract); Zweier et al., J. Clin. Invst. 80(6): 1728–1734 (1987) (Abstract); Singh et al., Mol. Cell. Biochem. 125(2): 97–104(1993); Nelson et al., Free Radic. Biol. Med. 16(2): 195–200 (1994) (Abstract); Burton, Am. J. Physiol. 248(5 Pt. 2): H637–H643 (1985) (Abstract); Chi et al. Circ. Res. 64(4): 665–675 (1989) (Abstract); Miura et al. Jpn. Circ. J. 53(7): 786–794 (1989) (Abstract); Konovalova et al. Biull Eksp Biol. Med. 98(8): 153–156 (1984) (Abstract); Gutkin et al. Biull. Eks. Biol. Med. 93(1): 33–35 (1982) (Abstract); and Wang et al., Hua. Hsi. I. Ko. Ta. Hsueh. Pao. 25(1): 62–65 (1994) (Abstract)). Ischemia is a deficiency of blood in a biological organism due to functional constriction or actual obstruction of a blood vessel, common in surgery, that causes cell tissue damage as a result of oxidation. Myocardial ischemia is a deficiency of blood supply to the heart muscle.

It is known to the art that the over expression of antioxidant enzymes retards the age-related accrual of oxidative damage. By the over expression of superoxide dismutase in *Drosphilia melanogaster*, the average and maximum life-span of transgenic fruit flies is extended. (Sohal et al., Science 273: 59–63 (1996)).

In contrast to the present invention, none of the above-cited references teach the use of an allene oxide synthase (such as RPP) as an antioxidant and none teach a beneficial curative effect to reduce or prevent cell damage caused by oxidative attacks.

3. SUMMARY OF THE INVENTION

The rubber particle protein (RPP) gene and the DNA template thereof are isolated and elucidated. The full-length cDNA clone of the abundant guayule RPP gene has been isolated and is described. It has been named pRPP30. A beneficial antioxidative effect of RPP and other allene oxide synthases is disclosed.

The present invention is based, at least in part, on the discovery that RPP from guayule rubber particles is not a prenyltransferase. Instead, it is a non-monooxygenase, cytochrome P450, heme-binding protein that generates lipid epoxides from lipid hydroperoxides. According to the present invention, RPP may be purified from guayule rubber particles, its activity may be measured, and the amino acid sequence for the pure protein may be determined. Further, the amino acid sequence information may be used to isolate the cDNA for RPP from a guayule stembark cDNA library, which may then be cloned and sequenced.

The present invention is also based, in part, on the discovery of similarities and differences between RPP and other AOS enzymes found in several monocotyledonous plants. These plant species do not produce rubber, and so their form of AOS is not involved in rubber synthesis.

The cloning of the cDNA for RPP and the elucidation of its protein sequence and structural domains, as disclosed herein, permits structure-function analysis and provides a foundation for determining its role in rubber biosynthesis in guayule and other organisms. As demonstrated herein, RPP is shown not to be a prenyltransferase but a non-monooxygenase type of cytochrome P450. RPP can form lipid epoxides from lipid hydroperoxides, and this appears to be crucial for high molecular weight rubber biosynthesis. Also, the expression of RPP in a natural or foreign host can be regulated by placing the pRPP30 cDNA downstream of an appropriate 5' promoter and transferring that recombinant gene to another host. The expression of functional RPP enzyme can be followed by a sensitive biochemical assay which monitors the rapid degradation of LOOH in the presence of RPP. The effect of RPP gene expression on rubber biosynthesis is also demonstrated by electron and light microscopy of transgenic plants. This invention is thus important to the agricultural, biological and chemical sciences and offers a basis for natural rubber production in a wide range of organisms, including prokaryotic and eukaryotic species using recombinant DNA methods.

Accordingly, a primary object of the present invention is to provide recombinant DNA molecules coding for RPP.

Another object of the present invention is to provide new and improved processes for the production of RPP polypeptides from recombinant DNA molecules coding for RPP.

A further object of the present invention is to provide vectors comprising DNA sequences coding for RPP and cultures of host organisms containing said vectors to produce recombinant rubber particle protein.

A further object is to use the recombinant RPP for stimulating rubber synthesis in other host organisms.

The present invention further relates to the isolation and use of an allene oxide synthase enzyme as an antioxidant of lipid peroxides in biological systems. It is based, at least in part, on the discovery that antioxidation is accomplished enzymatically by RPP, a species of allene oxide synthase, in guayule, and on the discovery that the allene oxide synthase RPP disrupts the chain reaction and propagation steps of lipid peroxidation.

In related embodiments, the present invention relates to the use of an allene oxide synthase to result in a time-dependent disappearance of conjugated dienes (i.e. lipid hydroperoxides). The allene oxide synthase rapidly converts free or esterified fatty acid peroxides or hydroperoxides into their corresponding epoxides, which, in turn are converted to ketols. The lipid peroxide and hydroperoxide substrates for this enzyme are known to be toxic to biological organisms and can generate additional peroxides by chain propagation reactions. In the presence of an allene oxide synthase these compounds are rapidly and effectively converted to allene oxides (the epoxide), thus breaking the chain reaction.

In various specific, nonlimiting embodiments, the present invention further provides for the following:

(1) the use of an allene oxide synthase as a preservative of plant seeds;

(2) the use of an allene oxide synthase as a treatment of trauma patients with severe blood loss;

(3) the use of an allene oxide synthase as a promoter of apoptosis in the treatment of plants and animals for certain diseases;

(4) the use of an allene oxide synthase in tobacco plants to make the tobacco plants resistant to oxidative herbicides, such as paraquat;

(5) the use of an allene oxide synthase to increase the effective life span of sperm used for artificial insemination or in vitro fertilization; and (6) the use of allene oxide synthase to increase the average and maximum life span of biological organisms, such as fruit flies.

These and still further objects as shall hereinafter appear are readily fulfilled by the present invention in a remarkably unexpected manner as will be readily discerned from the following detailed description of an exemplary embodiment thereof, especially when read in conjunction with the accompanying drawings.

3.1 DEFINITIONS

In order that the invention herein described may be fully understood, the following definitions are provided.

"Nucleotide" means a monomeric unit of DNA or RNA consisting of a sugar moiety (Pentose), a phosphate, and a nitrogenous heterocyclic base. The base is linked to the sugar moiety via the glycosidic carbon (1' carbon of the pentose) and that combination of base and sugar is called a "nucleoside". The base characterizes the nucleotide. The four DNA bases are adenine ("A"), guanine ("G"), cytosine ("C"), and thymine ("T"). The four RNA bases are A, G, C, and uracil ("U"). As is conventional for convenience in the structural representation of a DNA nucleotide sequence only one strand is shown in which A on one strand connotes T on its complement and G connotes C. Amino acids are shown either by a three letter or one letter abbreviation as follows:

| Abbreviated Designations | Amino Acid |
|---|---|
| A Ala | Alanine |
| C Cys | Cysteine |
| D Asp | Aspartic acid |
| E Glu | Glutamic acid |
| F Phe | Phenylalanine |
| G Gly | Glycine |
| H His | Histidine |
| I Ile | Isoleucine |
| K Lys | Lysine |
| L Leu | Leucine |
| M Met | Methionine |
| N Asn | Asparagine |
| P Pro | Proline |
| Q Gln | Glutamine |
| R Arg | Arginine |
| S Ser | Serine |
| T Thr | Threonine |
| V Val | Valine |
| W Trp | Tryptophan |
| Y Tyr | Tyrosine |

"DNA Sequence" means a linear array of nucleotides connected one to the other by phosphodiester bonds between the 3' and 5' carbons of adjacent pentoses.

"Codon" means a DNA sequence of three nucleotides (a triplet) which encodes through mRNA an amino acid, a translation start signal or a translation termination signal. For example, the nucleotide triplets TTA, TTG, CTT, CTC, CTA and CTG encode for the amino acid leucine ("Leu"), TAG, TAA and TGA are translation stop signals and ATG is a translation start signal.

"Reading Frame" means the grouping of codons during the translation of mRNA into amino acid sequences. During translation the proper reading frame must be maintained. For example, the DNA sequence GCTGGTTGTAAG may be expressed in three reading frames or phases, each of which affords a different amino acid sequence:

```
GCT GGT TCT AAG  -Ala-Gly-Cys-Lys

G CTG GTT GTA AG  -Leu-Val-Val

GC TGG TTG TAA G  -Trp-Leu-(STOP)
```

"Polypeptide" and "peptide" means a linear array of amino acids connected one to the other by peptide bonds between the alpha-amino and carboxyl groups of adjacent amino acids.

"Genome" means the entire DNA of a cell or a virus. It includes, inter alia, the structural gene coding for the polypeptides of the substance, as well as operator, promoter, terminator, enhancer and ribosome binding and interaction sequences.

"Gene" means a DNA sequence which encodes through its template or messenger RNA ("mRNA") a sequence of amino acids characteristic of a specific polypeptide.

"cDNA" means a complementary or copy DNA prepared by using mRNA as a template for synthesizing the first strand of DNA using reverse transcriptase, an appropriate oligonucleotide primer and a mixture of nucleotides.

"PCR" means a polymerase chain reaction whereby a specific DNA sequence, either genomic or cDNA, can be preferentially amplified by the enzyme Taq polymerase using synthetic, oligonucleotide sense and antisense primers, (which specify a target sequence), a mixture of nucleotides and a temperature thermocycling regime which allows sequential denaturing, annealing and synthesis of the target DNA between the primers.

"Transcription" means the process of producing mRNA from a gene or DNA sequence.

"Translation" means the process of producing a polypeptide from mRNA.

"Expression" means the process undergone by a gene or DNA sequence to produce a polypeptide and comprises a combination of transcription and translation.

"Plasmid" or "phagemid" means a nonchromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for ampicillin resistance ($AMP^R$) transforms a cell previously sensitive to ampicillin into one which is resistant to it. A cell transformed by a plasmid is called a "transformant".

"Phage" or "Bacteriophage" means a bacterial virus, many of which consist of DNA sequences encapsidated in a protein envelope or coat ("capsid").

"Cloning Vehicle" means a plasmid, phagemid, binary vector, phage DNA, cosmid or other DNA sequence which is able to replicate in a host cell, characterized by one or a small number of endonuclease recognition sites at which such DNA sequences may be cut in a determinable fashion without attendant loss of an essential biological function of the DNA, e.g., replication, production of coat proteins or loss of promoter or binding sites, and which contain a marker suitable for use in the identification of transformed cells, e.g., ampicillin resistance. A cloning vehicle is often called a vector.

"Cloning" means the process of obtaining a population of organisms or DNA sequences derived from one such organism or sequence by asexual reproduction.

"Recombinant DNA Molecule" or "Hybrid DNA" means a molecule consisting of segments of DNA from different genomes which have been joined end-to-end outside of living cells and able to be maintained in living cells.

"Expression Control Sequence" means a sequence of nucleotides that controls and regulates expression of genes when operatively linked to those genes. They include but are not limited to the lacZ promoter, the trp promoter, the tac and trc promoter, the T7 polymerase promoter and other major prokaryotic and eukaryotic promoters which increase expression of foreign genes in prokaryotic hosts and the NOS promoter and terminator, the CaMV 35S promoter and other prokaryotic and eukaryotic promoters which increase the expression of genes in eukaryotic cells or their viruses or combinations thereof.

"Guayule rubber particle protein" (RPP), is a polypeptide of 53,500 Daltons, localized in the rubber particles of guayule. It is a non-mono-oxygenase, cytochrome P450 heme-binding protein which has an essential function for rubber biosynthesis in plants which is believed to be involved with epoxide formation.

4. BRIEF DESCRIPTION OF THE DRAWINGS

Figure 7:
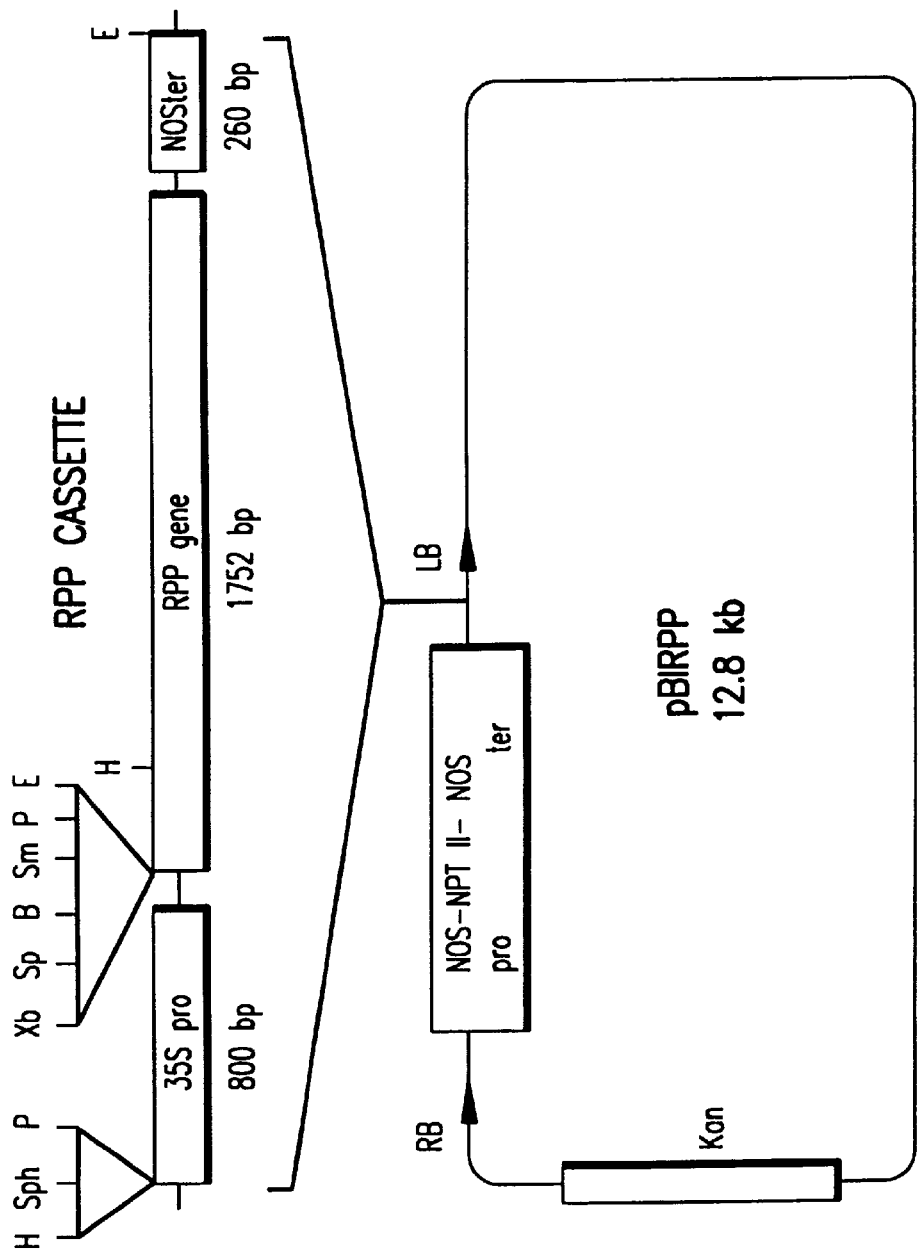

FIG. 1 depicts the amino acid sequences of four different fragments (SEQ ID NOS: 1–4, respectively) obtained from a cyanogen bromide digest of purified guayule rubber particle protein;

FIGS. 2A–B (collectively referred to herein as FIG. 2) displays the chemically synthesized Oligonucleotide DNA probes and/or primers SEQ ID NOS: 5–11, respectively) used in accordance with the present invention;

FIGS. 3A–G (collectively referred to as FIG. 3) displays the full-length nucleotide sequence (SEQ ID NO: 12) of the pRPP30 cDNA clone of guayule rubber particle protein gene, and its encoded protein (SEQ ID NO: 12) (* denotes known amino acid sequences of CNBr fragments of RPP; ——>denotes the position of chemically synthesized oligonucleotide, sense-strand probes used to amplify RPP cDNA by polymerase chain reaction; <—— denotes the position of chemically synthesized oligonucleotide, antisense-strand probes used to amplify RPP cDNA by polymerase chain reaction);

FIG. 4 displays a map of the guayule RPP cDNA in pRPP30 depicting restriction endonuclease sites; the position of primers P1, P3, P8, P9, P5, P6 and the PCR generated P5/P6, 92 bp probe; the positions of the CNBr peptide fragments #1, #2, #3 and #4; and the potential N-linked glycosylation sites (*) (Abbreviations: Af=Afflll; Ag=Agel; Ap=Apal; B=Bam1; Bs=Bsgl; H=Hindlll; K=Kpnl; Nh=Nhel; P=Pstl; Pv=Pvull; Sa=Sacl; Sc=Scal; Sm=Smal; Sp=Sphl; Ss=Sspl; Xb=Xbal; Xh=Xhol);

FIG. 5 displays the amino acid sequence comparison of RPP with flaxseed AOS showing 65% identity and 80% similarity;

FIG. 6 displays the biochemical analysis of RPP purified from guayule rubber particles. FIG. 6A is a Coomassie blue stained SDS gel showing each of the purification steps leading to purified RPP. Lane 1 contains crude homogenate; lane 2 contains 3×washed rubber particles; lane 3 contains 0.5% CHAPS solubilized RPP, filtered through a Millipore Millex-GV, 0.22 um, SLGV filter which removes the remaining rubber particles; lane M contains the molecular weight markers. FIG. 6B is an autoradiograph of a TLC plate showing products of prenyltransferase activity from each purification step from lanes 1, 2 and 3, panel A. Aliquots from each purification step were incubated with $^{14}$C-IPP, DMAPP, $Mg^{+2}$ and $Mn^{+2}$ to yield isoprenes of various chain-lengths as shown (arrows): SQ, squalene; P, phytoene; X, unknown isoprenes; GG, geranylgeraniol; F, farnesol; G, geraniol; O, origin. Note that pure RPP in lane 3 synthesizes no isoprenes compared to the crude homogenate in lane 1 and washed rubber particles in lane 2. FIG. 6C is a difference spectra of the pure CHAPS-solubilized, filtered RPP from lane 3, Panel A. Reference and sample cuvettes were reduced with sodium dithionite and the sample cuvette was bubbled with CO to produce a characteristic peak at 450 nm (arrow). FIG. 6D shows AOS-like activity in an aliquot of pure, CHAPS-solubilized, filtered RPP from lane 3, Panel A. Activity is measured by repetitive UV scans at 10 sec intervals showing the disappearance of linoleic acid hydro peroxide (LOOH) which has an absorbance maximum at 234 nm. Upon addition of pure RPP to the cuvette, LOOH is rapidly metabolized to allene oxide, observed by a decrease in absorbance at 234 nm. Complete disappearance of LOOH occurs after 10 minutes;

FIG. 7 displays a map of pBIRPP, the 12.8 kb, binary plasmid vector which is used to transform tobacco. It contains the RPP cassette in a sense orientation. RPP cDNA from pRPP30 was inserted downstream of the 35S promoter and upstream of the NOS terminator, by replacing the GUS gene from pBI121.

Figures 8A, 8B:
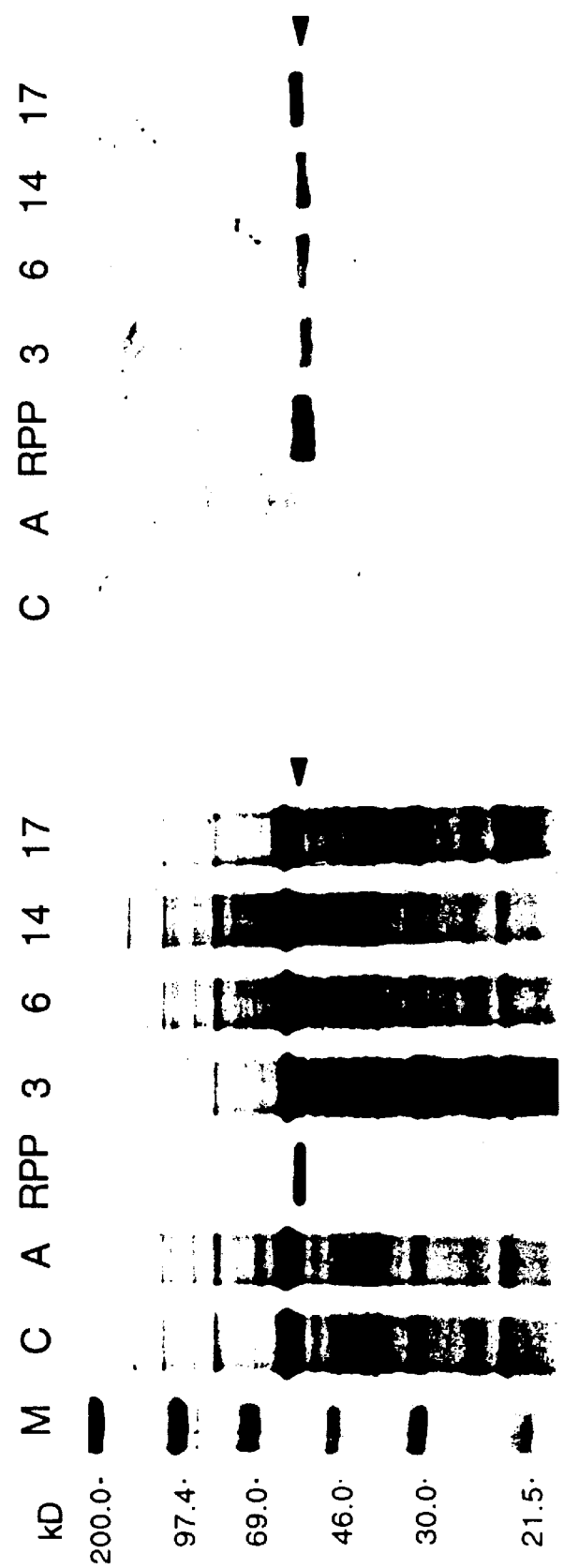
Figure 8D:
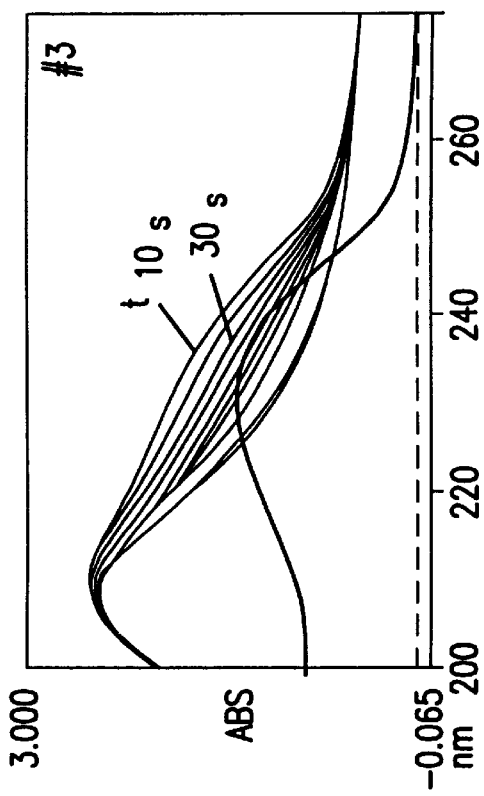
Figure 8C:
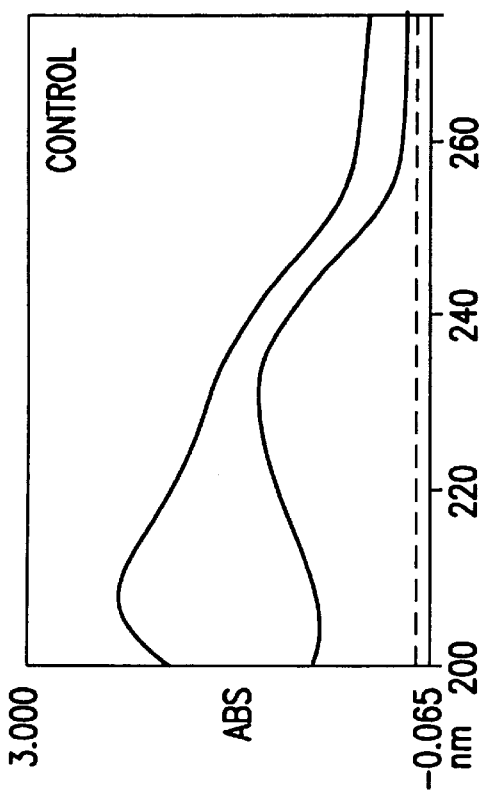

FIG. 8 displays the biochemical analyses of tobacco plants transformed with the pBIRPP binary vector that produces functional RPP. FIG. 8A shows a Coomassie blue stained SDS gel of total proteins extracted from tobacco transformed with RPP expressed in the sense orientation. It shows RPP (arrow) in 4 different transformants (#3, #6, #14, and #17). Proteins from non-transformed, control tobacco (C) and from tobacco with an antisense construct of RPP cDNA (A) do not produce RPP. Molecular weight markers (M) and the position of authentic RPP from washed guayule rubber particles (RPP) are indicated. FIG. 8B shows a Western hybridization of a gel identical to Panel A. The blot was probed with a monospecific RPP-antibody and stained with alkaline phosphatase conjugated, secondary antibody. The blot shows a single band (arrow) of RPP in each of the tobacco transformants (#3, #6, #14, #17) in the sense orientation. Control tobacco (C) and antisense constructs (A) do not produce RPP. FIG. 8C shows that AOS-like activity of functional RPP is absent in protein extracts from non-transformed, control tobacco (C). These plants do not produce RPP and consequently do not metabolize LOOH. The spectra depicts repetitive scans made at 10 sec intervals over several minutes with no loss of LOOH in the sample cuvette. FIG. 8D shows high AOS activity in protein prepared from tobacco transformant #3. These plants express the foreign guayule RPP gene and produce functional RPP. This is observed by the rapid disappearance of the 234 nm LOOH peak scanned at 10 sec intervals after following addition of tobacco protein extracts. Scans after 10 and 30 seconds, respectively, are indicated by arrows and are labeled. Repetitive scans over several minutes show the complete loss of LOOH in the sample cuvette after 10 minutes.

Figure 9A:
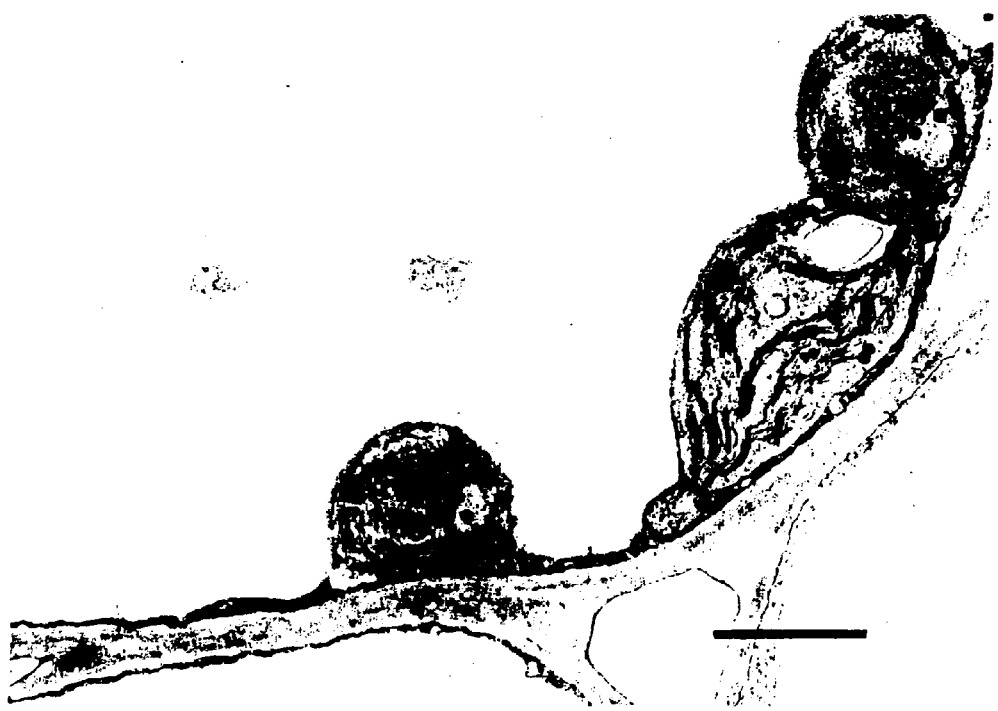
Figure 9B:
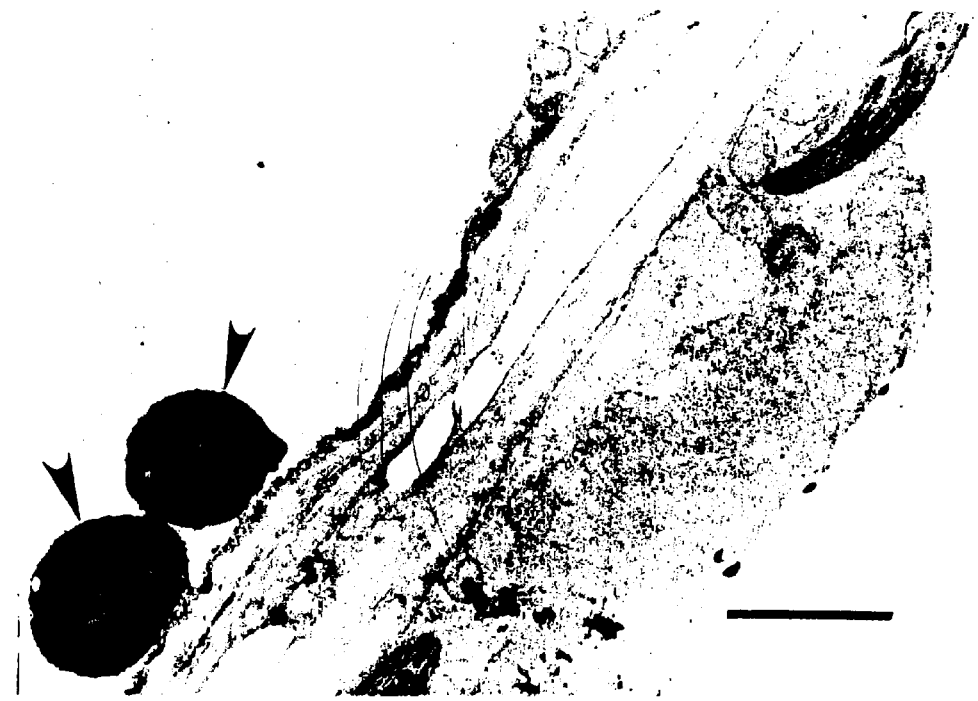

FIG. 9 displays electron micrographs of non-transformed (FIG. 9A) and pBIRPP-transformed (FIGS. 9B and C) tobacco (transformant #3) that produces functional guayule RPP. Cells from non-transformed plants (FIG. 9A) do not contain rubber particles, whereas cells from transformed plants (in FIGS. 9B and C) do produce polyisoprene and containing particles (arrows) which are observed primarily in the vacuoles. Bar equals 2 µm.

Figure 10A:
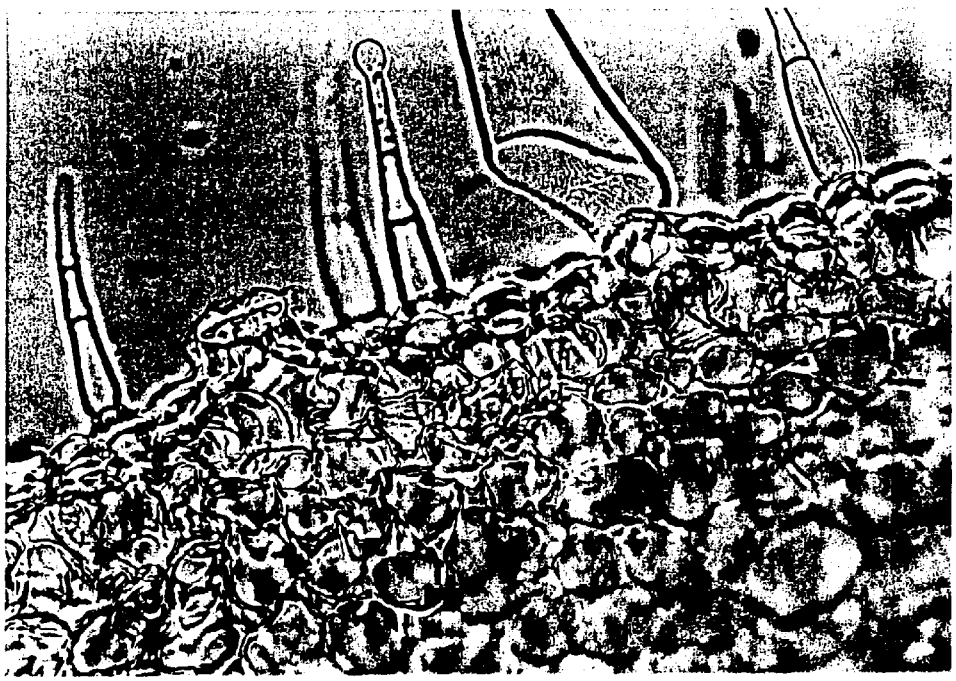

FIG. 10 displays light micrographs of non-transformed (FIG. 10A) and pBIRPP transformed (FIG. 10) tobacco plants stained with calco oil blue which is specific for rubber and polyisoprene. Cells of non-transformed plants do not contain these particles, whereas cells of transformed plants do contain these particles which appear as dark blue staining globules within the cells (arrows).

Figure 11:
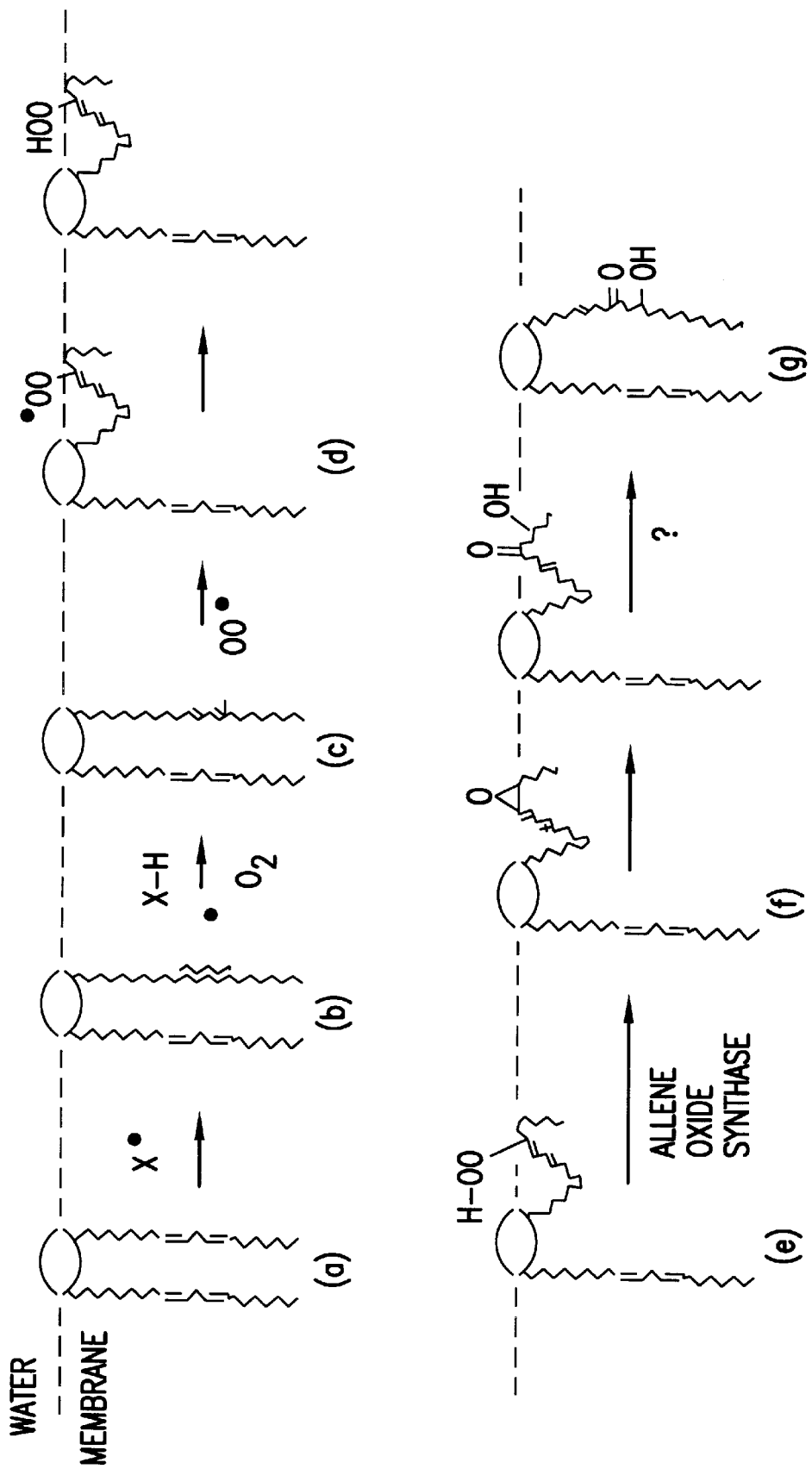

FIG. 11 displays an analysis of membrane lipid peroxidation, showing (a) initiation of peroxidation by oxidizing radical; (b) oxidation to form peroxyl radical; (c) peroxyl radical partitions to water-membrane interface; (d) lipid peroxide/lipid hydroperoxide poised in membrane-water interface for repair by allene oxide synthase; (e) conversion of lipid hydroperoxide to lipid epoxide by allene oxide synthase; (f) spontaneous decomposition of epoxide to ketol; and (g) possible reorientation of ketol in membrane-water interface.

Figure 12:
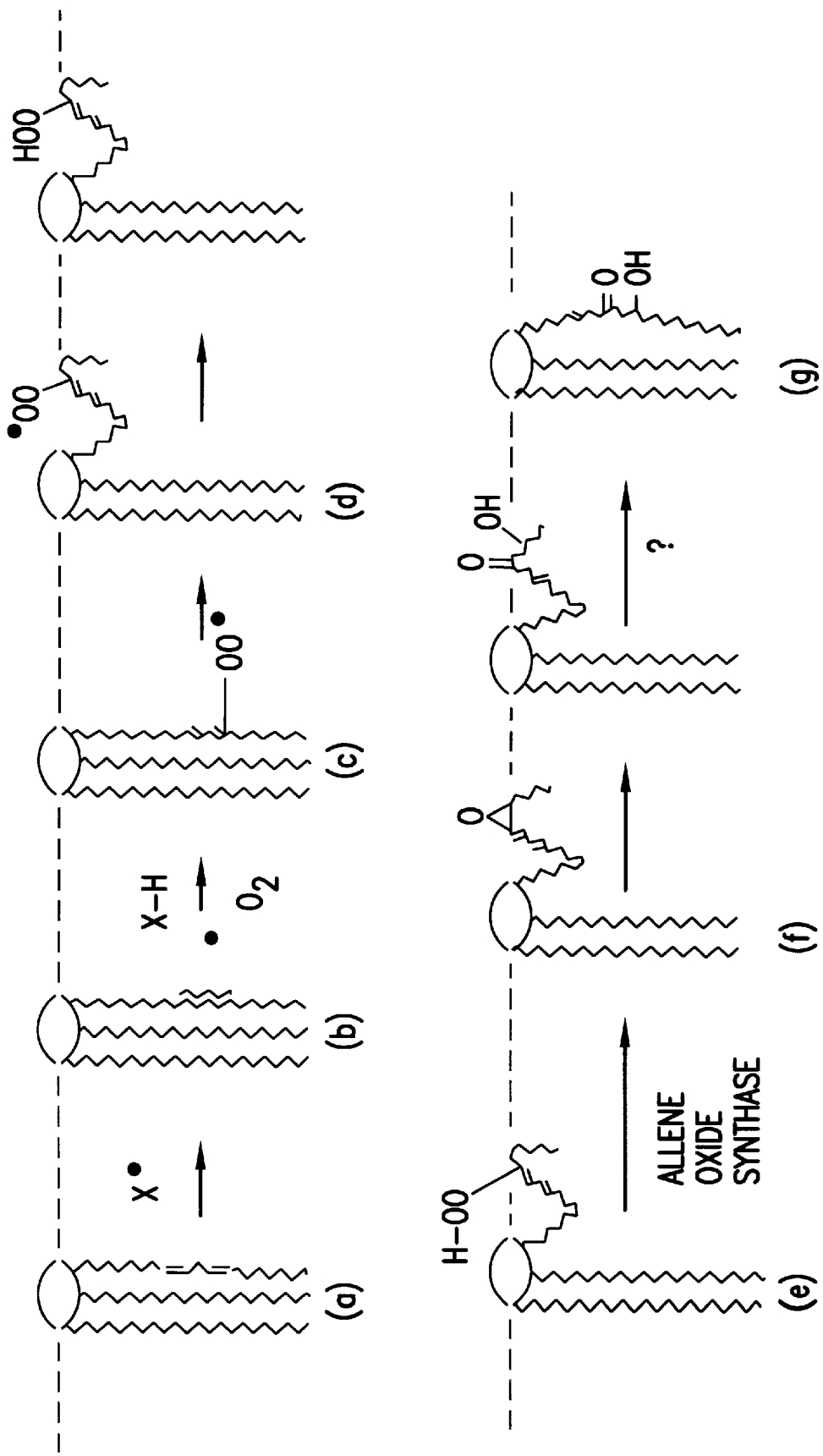

FIG. 12 displays an analysis of lipid peroxidation and repair of triglycerides in micelles, showing (a) initiation of peroxidation by oxidizing radical; (b) oxidation to form peroxyl radical; (c) peroxl radical partitions to water-membrane interface; (d) lipid peroxide/lipid hydroperoxide poised in membrane-water interface for repair by allene oxide synthase; (e) conversion of lipid hydroperoxide to lipid epoxide by allene oxide synthase; (f) spontaneous decomposition of expoxide to ketol; and (g) possible reorientation of ketol in membrane-water interface.

Figure 13A:
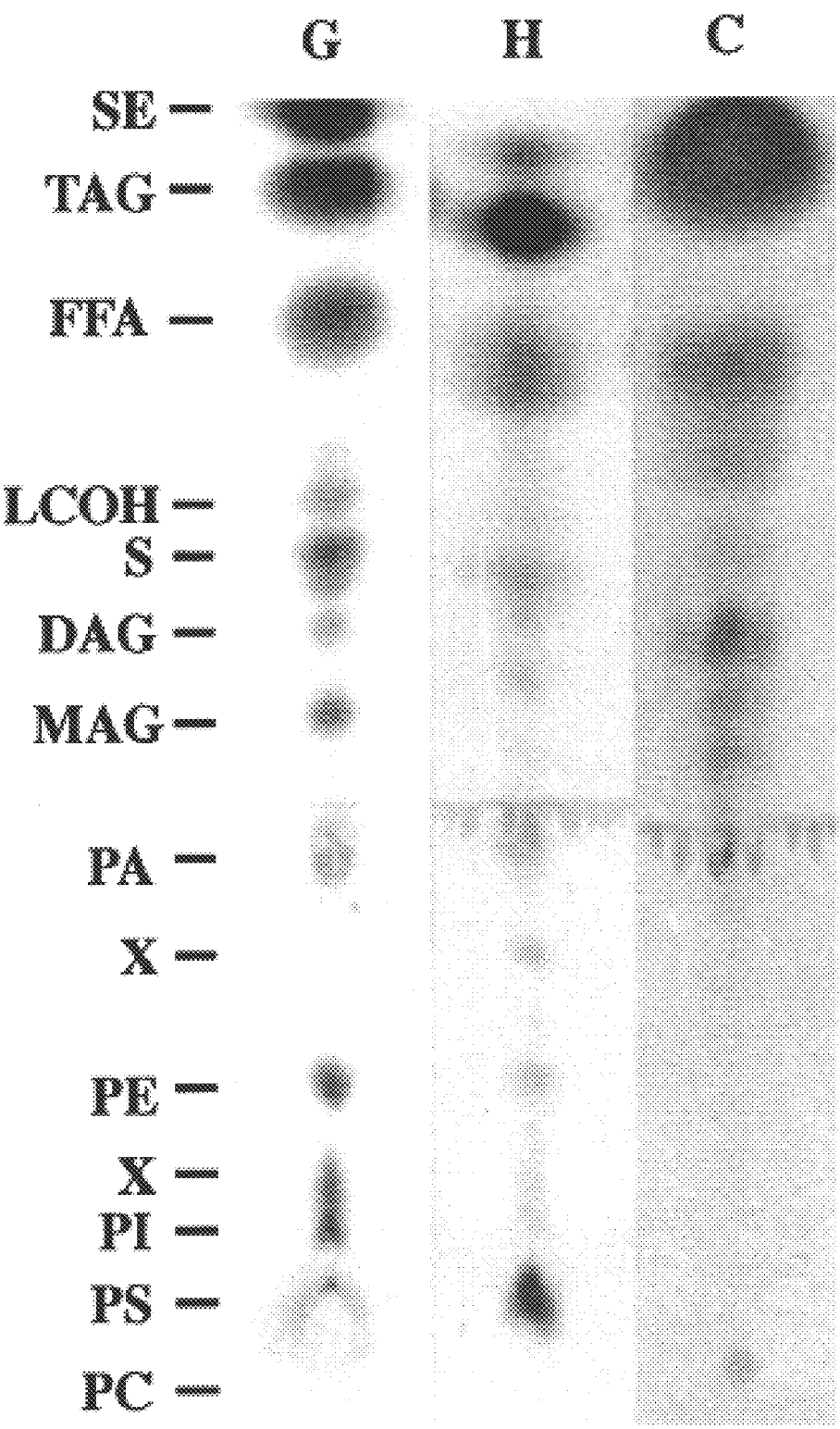
Figure 13B:
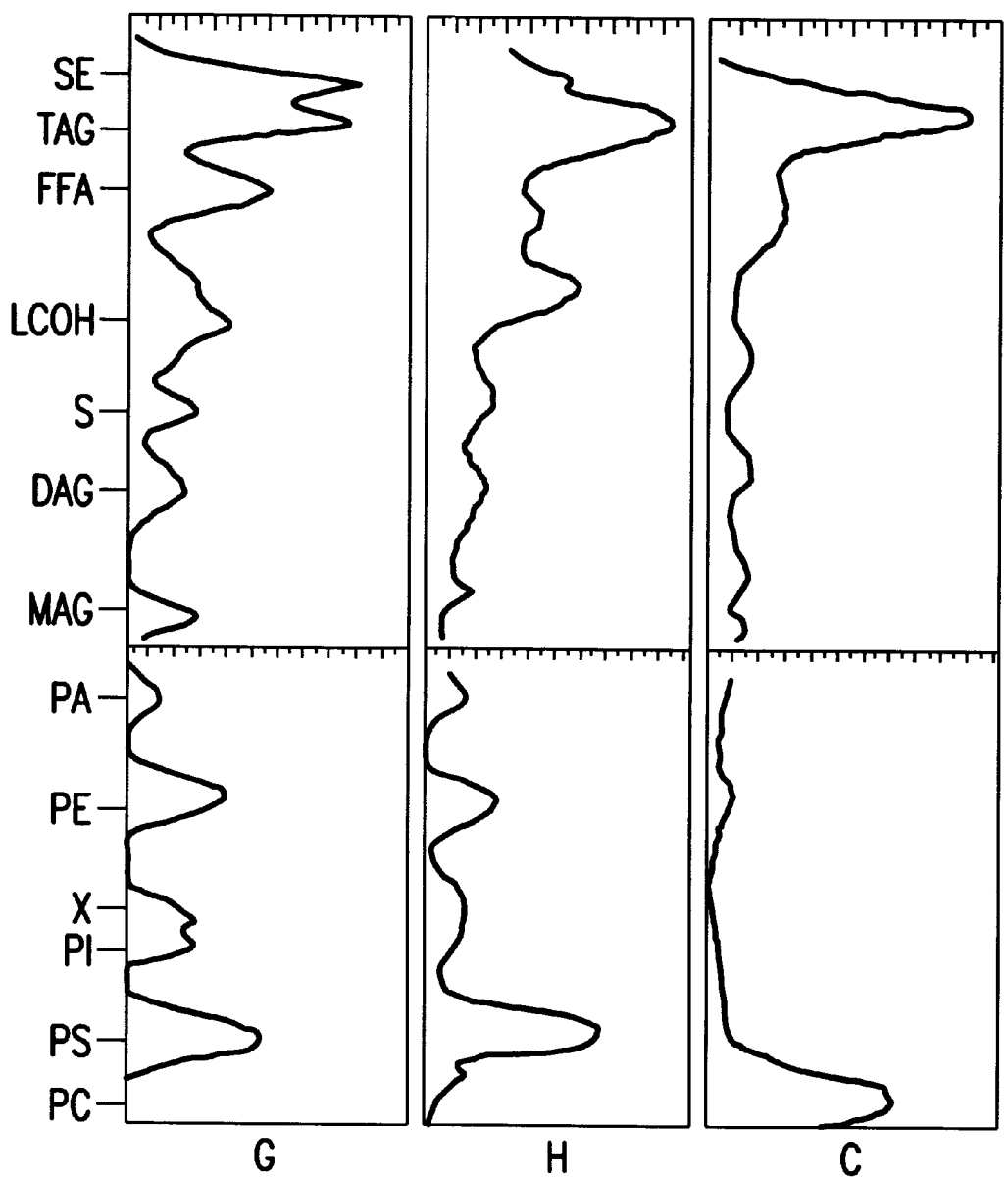

FIG. 13 displays an analysis of neutral and polar lipids of lipophilic particles. FIG. 13A is a photographic composite of three plates of a TLC analysis of neutral and polar lipids from guayule (col. G) and Hevea (col. H.) rubber particles, and cucumber (col. C) oil bodies, wherein the plates were stained by iodine vapor. (Note: the PS spot has faded and does not reflect the actual amount shown after charring of sulfuric acid-sprayed plates.) FIG. 13B displays densitometric scans of the respective sulfuric acid-sprayed plates wherein the amount of lipid, indicated by peak size, is relative to the class of lipid, i.e. neutral lipid or phospholipid.

Figure 14:
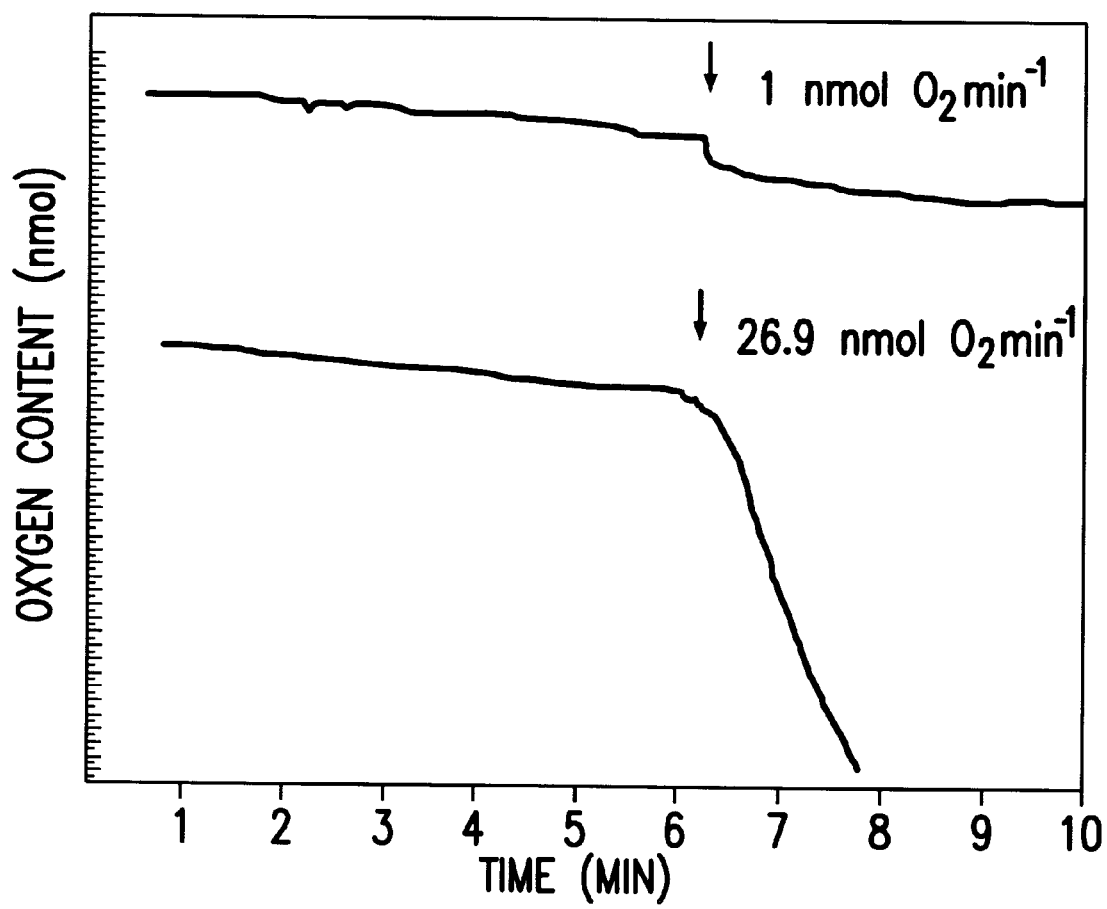

FIG. 14 displays a graph of oxygen consumption of guayule rubber particles exposed to lipoxygenase (↓) following treatment with (bottom curve) or without (top curve) pancreatic lipase.

Figure 15A:
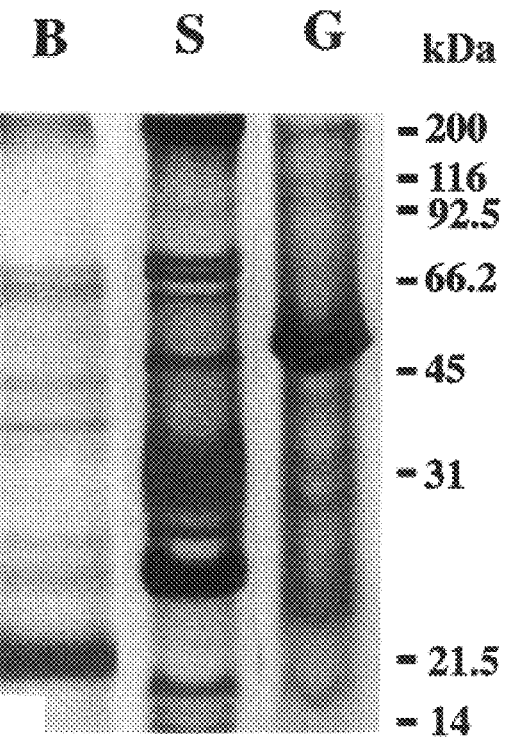

FIG. 15 displays an analysis of Brassica (col. B) and soybean (col. S) oil bodies compared to guayule (col. G) rubber particle proteins. FIG. 15A displays SDS-PAGE of total proteins from Brassica, soybean and guayule particles, wherein the arrows indicate the abundant proteins for Brassica (24KD) and soybean (24KD) oleosins and guayule (53KD), respectively.

Figure 15B:
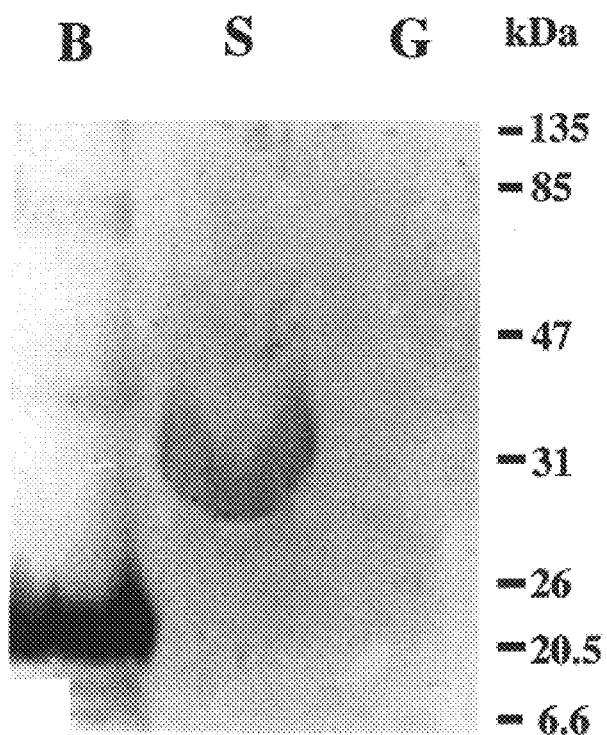
Figure 15C:
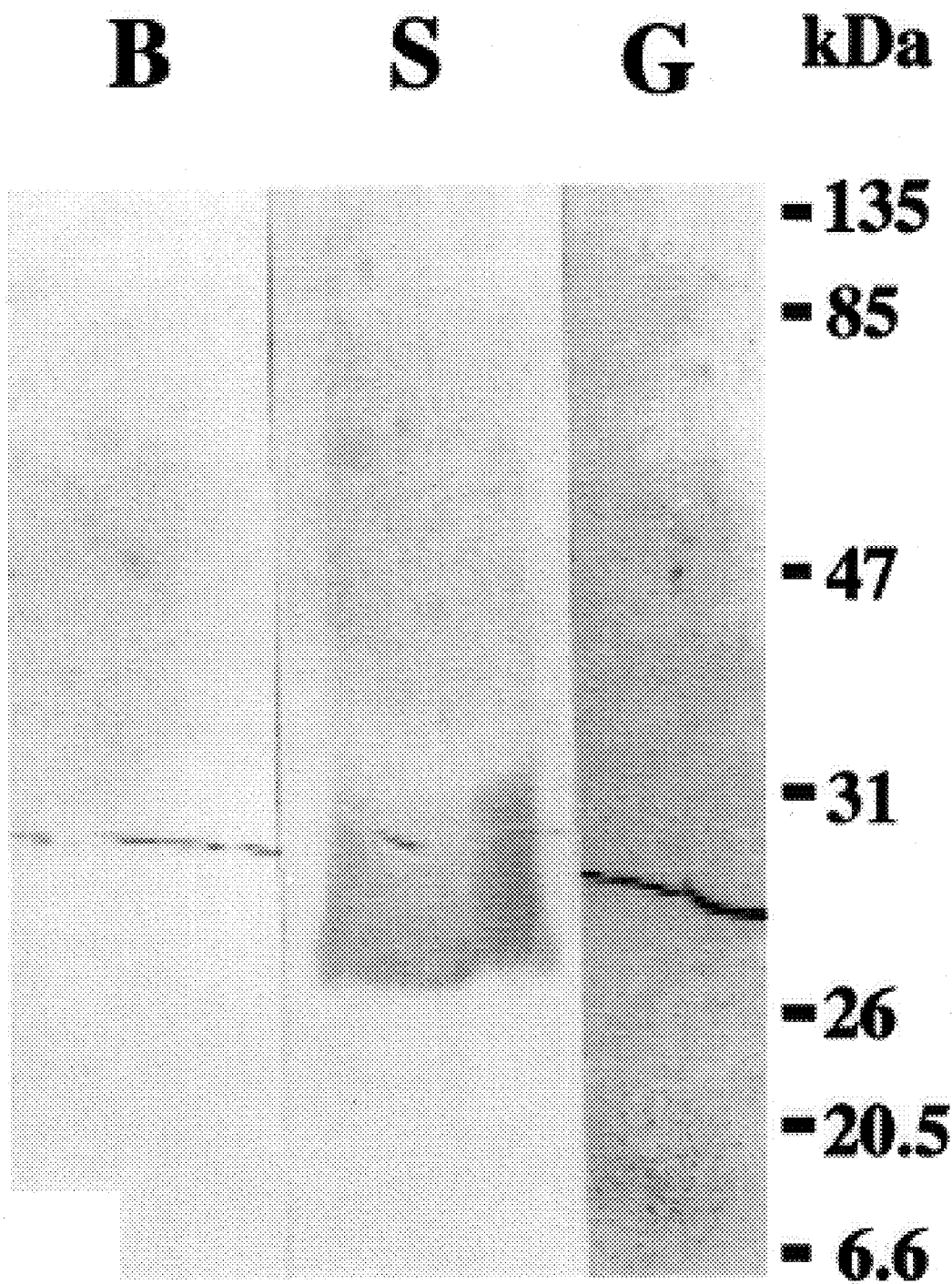

FIGS. 15B and 15C are two separate immunoblots presented in a side-by-side comparison, wherein FIG. 15B displays three columns (B, S and G) of an immunoblot probed with antibody to Brassica oleosin, and FIG. 15C displays three columns (B, S, and G) of an immunoblot probed with antibody to soybean oleosin.

Figure 16A:
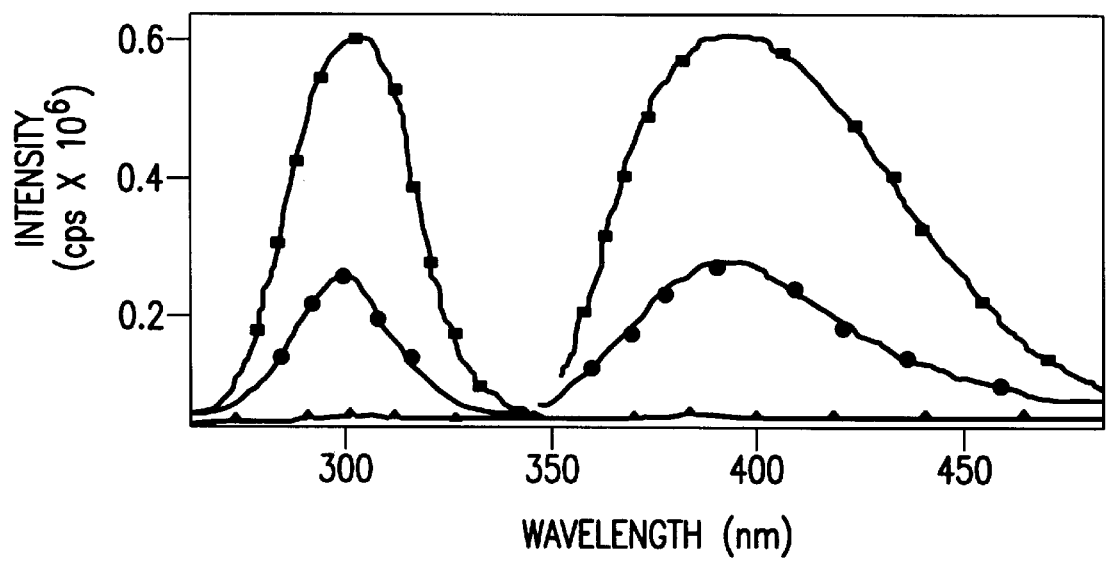
Figure 16B:
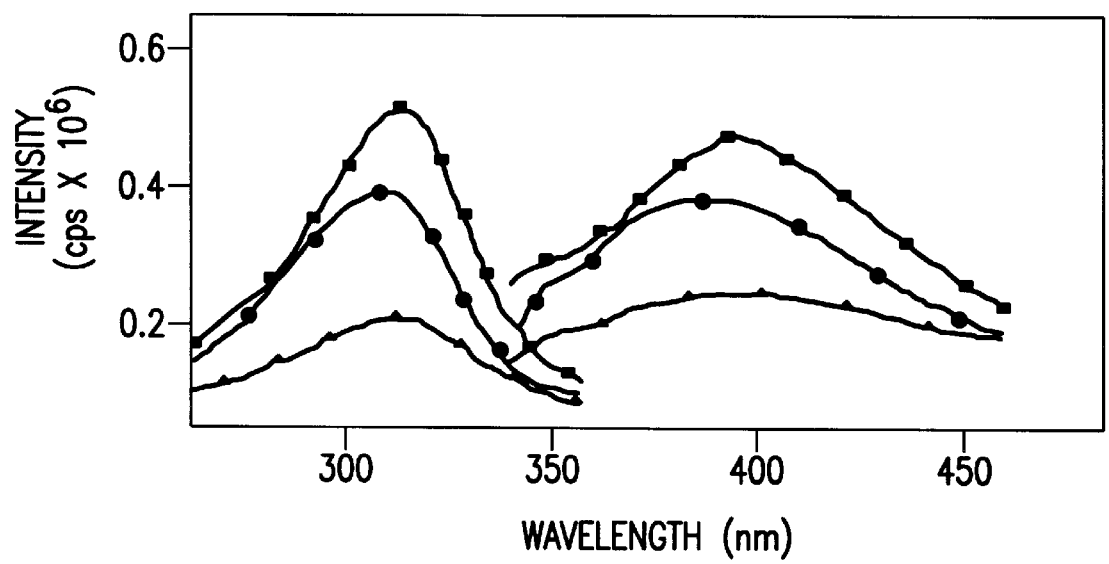

FIG. 16 displays a graphic comparison of typical fluoresence spectra of rubber particles shown in FIG. 16A and extracted lipids shown in FIG. 16B before (curve ▲), 5 minutes after (curve ●) and 20 minutes after (curve ■) treatment with 1 mM acetylsalisylic acid (ASA). The excitation maxima and emission maxima are 305 nm and 410 nm, respectively.

Figure 17:
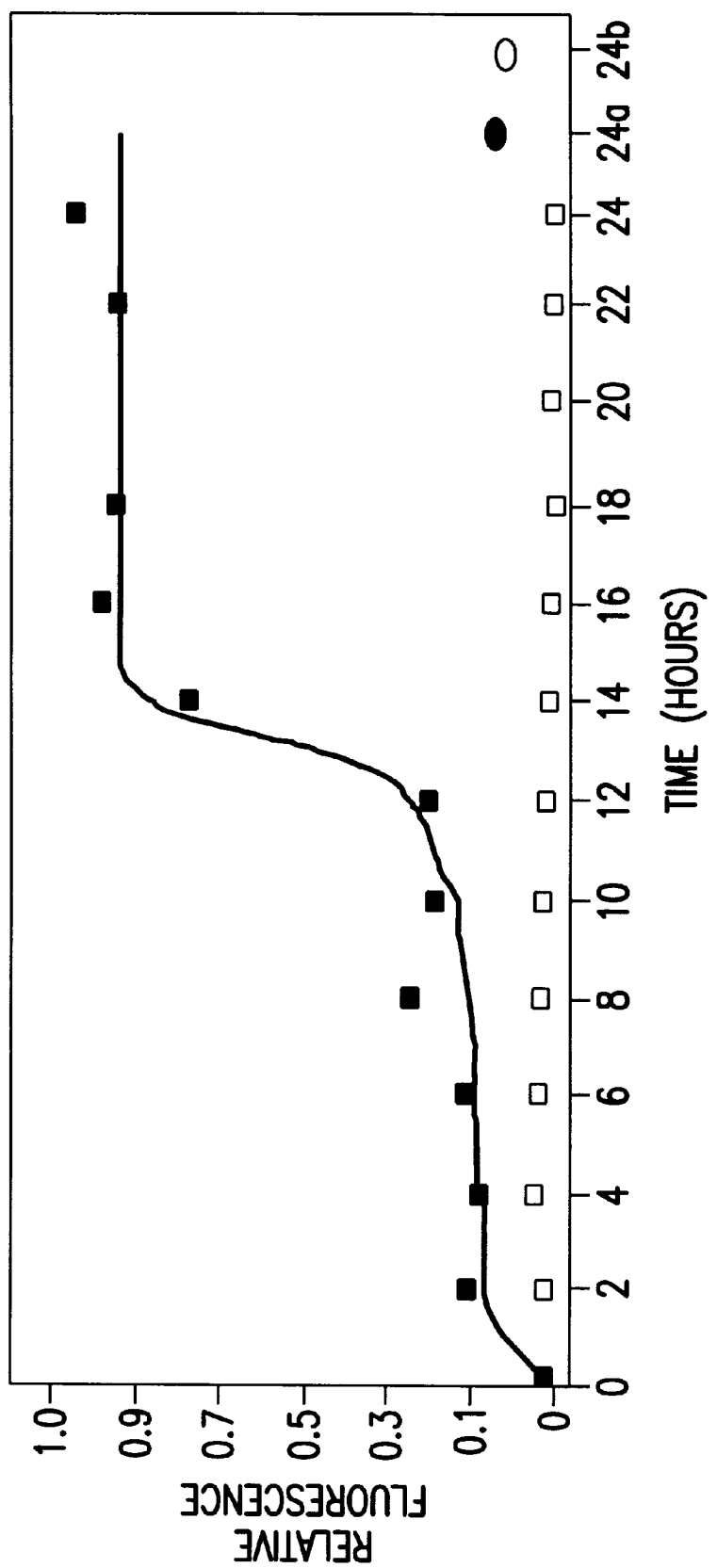

FIG. 17 displays a graph comparing relative fluorescence over 24 hours in active particles (curve □), particles treated with 1 mM ASA (curve ■) or particles treated with 1 mM ASA and an antioxidant [α-tocopherol (●24a) or BHT (O 24 b)].

Figure 18A:
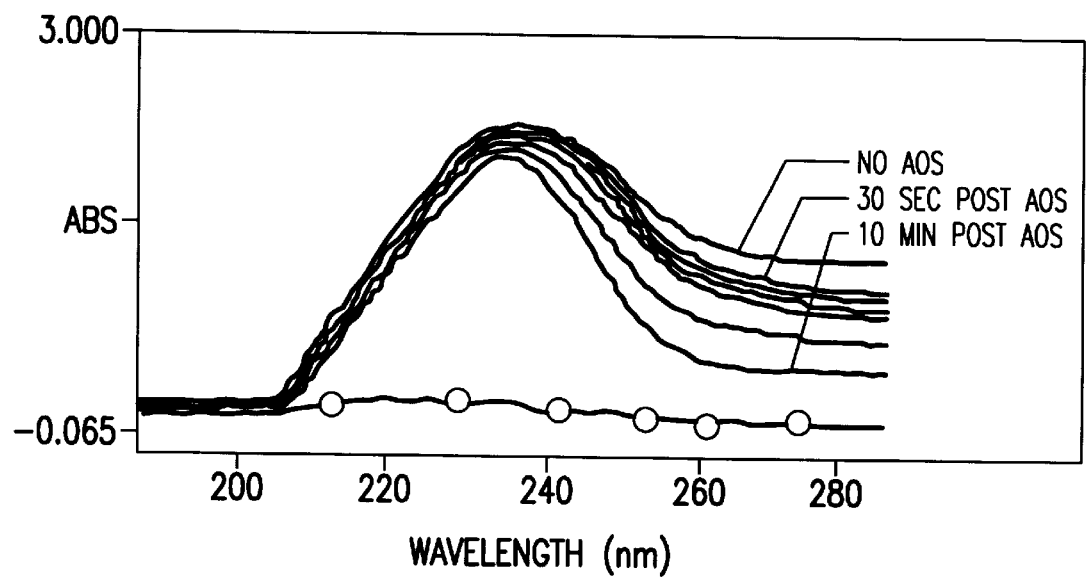
Figure 18B:
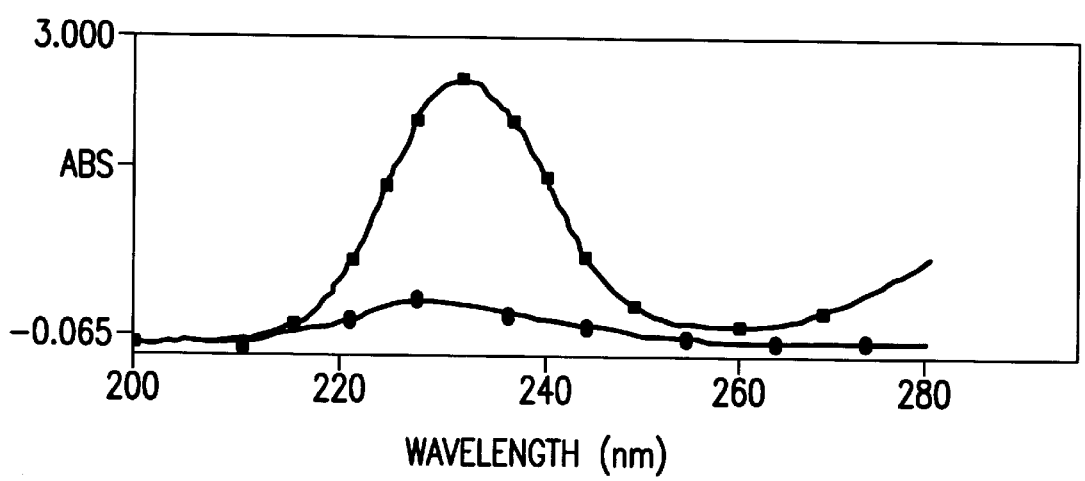

FIG. 18 displays a graphic comparison of the affects of AOS on linoleic acid conjugated dienes. FIG. 18A displays linoleic acid conjugated acid diene degradation in the presence and absence of AOS as observed by UV absorbance. Linoleic acid, prior to exposure of superoxide, having no conjugated diene is shown by curve (●). Additional curves show results at 10 minutes post AOS, 30 seconds post AOS and no AOS. FIG. 18B displays conjugated diene formation as affected by the presence of AOS inhibited by ASA (curve ■) or active AOS (curve ●).

Figure 19:
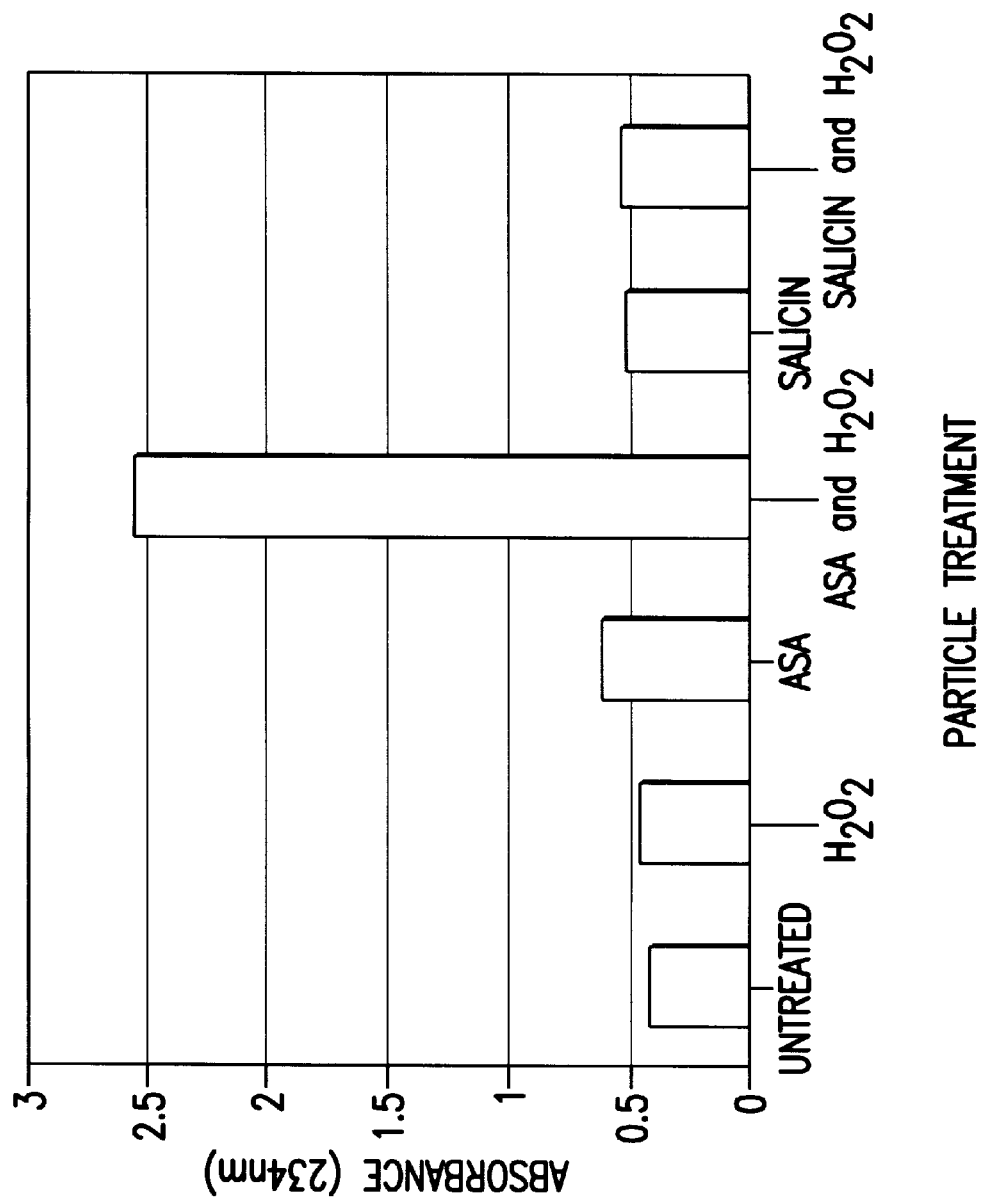

FIG. 19 displays a graphic comparison of the amount of conjugated diene in lipids extracted from rubber particles, wherein the particles were treated as indicated in the graph, the lipids extracted, and the UV absorbance measured.

Figure 20:
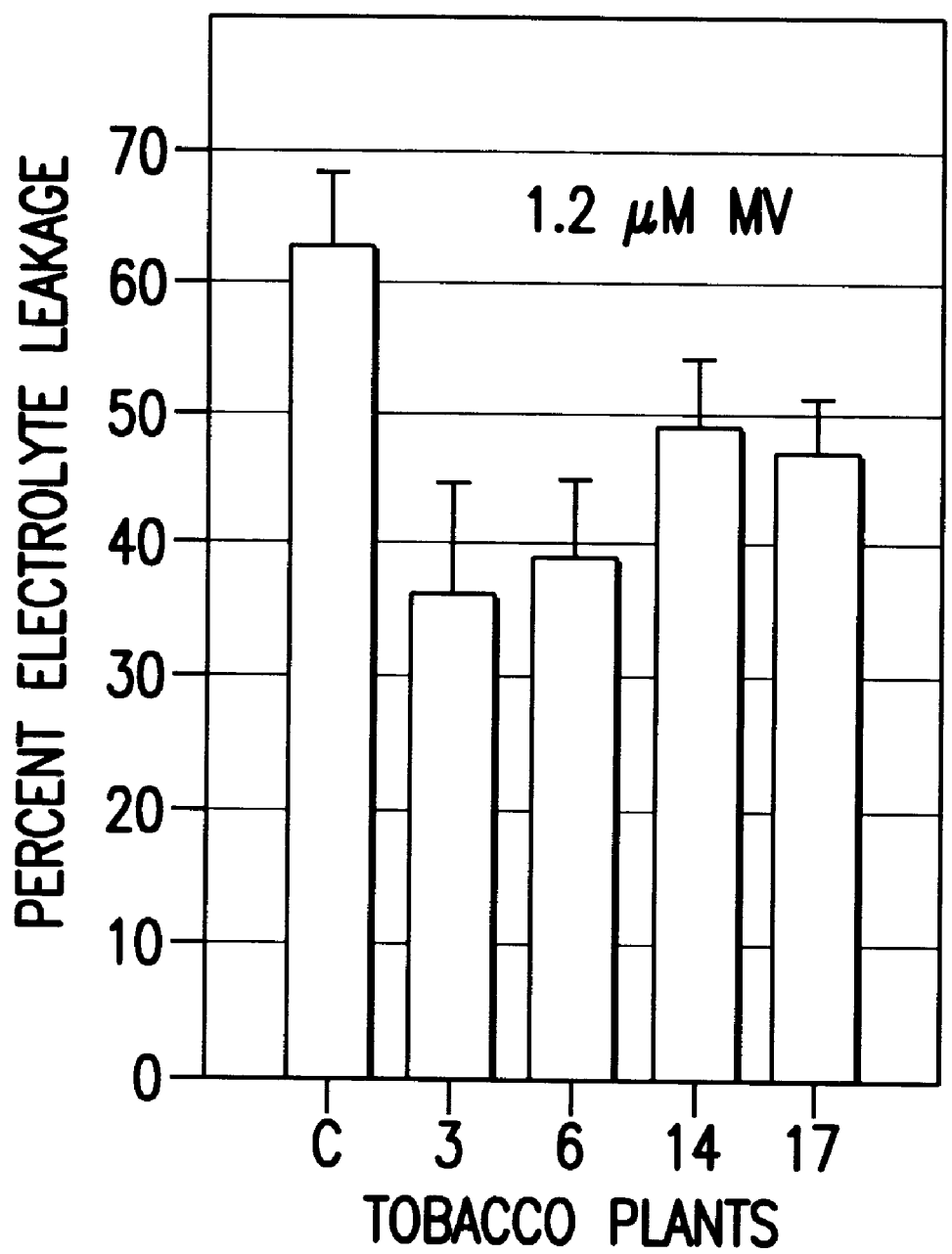

FIG. 20 displays a graphic analysis of cell leakage of transgenic AOS (#3, #6, #14, and #17) and untransformed tobacco plants (C).

5. DETAILED DESCRIPTION OF THE INVENTION

For purposes of clarity of description, and not by way of limitation, the detailed description of the invention is divided into the following subsections:

(i) the RPP gene and its encoded protein;
(ii) RPP expression;
(iii) RPP is a species of AOS;
(iv) uses of RPP and other AOS enzymes.

5.1 THE RPP GENE AND ITS ENCODED PROTEIN

In one specific embodiment, the present invention relates to a purified and isolated nucleic acid molecule having the nucleic acid sequence set forth in FIG. 3 and SEQ ID NO: 12, which is the full-length cDNA of guayule RPP.

In related embodiments, the present invention provides for a purified and isolated nucleic acid sequence which is at least 90 percent homologous, and preferably at least 95 percent homologous, to a nucleic acid molecule having a sequence as set forth in FIG. 3 and SEQ ID NO: 12. Homology may be determined using any standard software for calculating homology between nucleic acid molecules, for example, but not by way of limitation, the FASTA algorithm (Genetics Computer Group, Univ. Res. Park, Madison, Wis.; version 8.0). Sources capable of polyisoprene synthesis may be particularly likely to contain RPP homologs.

The present invention also provides for nucleic acid molecules encoding a protein having an amino acid sequence as set forth for RPP in FIG. 3 and SEQ ID NO: 12.

In further embodiments, the present invention provides for a purified and isolated protein having an amino acid sequence as set forth in FIG. 3 and SEQ ID NO: 12 for full-length RPP. In related embodiments, the present invention provides for functionally equivalent proteins. For example, one or more of the amino acid residues within the sequence may be substituted with another amino acid residue of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan, and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also within the scope of the invention are RPP proteins that have been modified post-translationally, by incorporation into a larger molecule.

The present invention also provides for a purified and isolated protein encoded by a nucleic acid molecule having the sequence set forth in FIG. 3 and SEQ ID NO: 12 or which is at least 90 percent, and preferably at least 95 percent homologous thereto. The present invention also provides for functional equivalents of these proteins, as defined above.

The first step taken to isolate a cDNA clone for the RPP gene was to use amino acid sequence data from pure RPP to generate DNA probes to screen a cDNA library. To do this, RPP was purified to homogeneity and cleaved with CNBr. RPP was cleaved into 4 distinct fragments which were sequenced from their N-termini (FIG. 1, SEQ ID NOS: 1–4, respectively). Oligonucleotides corresponding to the known protein sequences were synthesized (FIG. 2, SEQ ID NOS: 5–10, respectively) and used to prime plus and minus strand amplification of guayule bark cDNA, via the polymerase chain reaction (PCR). Using primers 5 and 6 we obtained a 92 bp fragment of DNA which, upon sequencing, matched perfectly with the known protein sequence of peptide fragment #3 of RPP (FIG. 2). This 92 bp probe was then used to screen a lambda ZAP, stembark cDNA library. Positive clones were rescreened at least two times with radioactive probes to verify hybridization. Forty five cDNA clones were obtained which contained RPP cDNAs of various lengths. The four longest clones were sequenced and found to be identical in their protein coding region and all contained DNA sequences coding for the four CNBr fragments shown in FIG. 1. The order of those fragments in the protein sequence was #4, #2, #1, and #3 respectively (FIGS. 3 and 4), going from the 5' to 3' direction of the gene. The RPP cDNA clone described in this application is one of the four full-length clones isolated. It is named pRPP30 and is shown in FIGS. 3 and 4. The pRPP30 gene is 1692 bp long, SEQ ID NO: 3 and contains an open reading frame of 1419 bp for RPP. The 1419 bp open reading frame encodes a 473 amino acid sequence SEQ ID NO: 3 equivalent to 53,438 Daltons and includes 8 methionines and 2 cysteines. The deduced pI of the 473 amino acid protein is 6.15, which agrees with the experimental value of 6.2 for RPP (Backhaus et al. Phytochem. 30:2493–2497 (1991)). There are 3 potential N-linked, glycosylation sites in RPP of sequence Asn-X-Ser/Thr, wherein X can be any of the common 20 amino acids. In addition, pRPP30 contains a stop codon (TGA), a 5'-noncoding region of 23 bp and a 3'-noncoding region of 250 bp. The pRPP30 cDNA is composed of the 1692 bp RPP gene contained within a Bluescript SK- (Stratagene, Inc) phagemid. This phagemid is a well-known and commercially available cloning vector. The pRPP30 cDNA phagemid is a 4631 bp circular molecule, of which 1692 bp is the RPP gene inserted between the unique EcoRl and Xhol cloning sites of that vector. A map of the pRPP30 is shown (FIG. 4).

The original source of material for isolating the pRPP30 cDNA molecule was stembark tissue from the 11591 line of guayule shrubs. This tissue is rich in natural rubber and is readily available from guayule field plots growing in and around the Phoenix metropolitan area. The lambda ZAP cDNA cloning system used herein is a well-known and commonly available lambda phage expression vector. Its construction and restriction endonuclease map are described by Short, et al. Nucl. Acids Res. 16:7583–7600 (1988); Huse and Hansen, Strategies 1:1–3; Sorge, Strategies 1:3–7 (1988); and associated techniques in Gubler and Hoffman, Gene 25:263 (1983); Young and Davis, Proc. Natl. Acad. Sci. USA 80:1194–1198 (1983); and Watson and Jackson, DNA cloning—A practical approach 79–88 (1985).

5.2 RPP EXPRESSION

The present invention provides for vectors comprising the above mentioned RPP gene nucleic acid molecules, including plasmid, phage, cosmid, and viral vectors. The foregoing nucleic acid molecules may be combined, in such vectors or otherwise, with nucleic acid sequences which may aid in their expression, including promoter/enhancer sequences and other sequences which aid in transcription, translation, or processing. Vectors of the invention may further comprise other sequences, such as selection markers, as used by skilled artisans.

The present invention further provides for the isolated RPP promoter, as may be identified in a genomic clone which hybridizes to the 5' end of a nucleic acid molecule as depicted in FIGS. 1–3. The precise location of the promoter may be analyzed by correlating the effect of site-directed deletions in nucleic acid 5' to the coding sequence with transcription of RPP or a reporter gene. The RPP promoter may be linked to a reporter gene and then used to study RPP expression or the effects of various agents on RPP expression.

For example, but not by way of limitation, the RPP coding region may be inserted into the pYEDP60 plasmid vector (Truan et al., Gene 125: 49–55 (1993)) downstream of the GAL 10 promoter. The plasmid may then be transferred to yeast and allowed to grow for a period before it is induced with galactose to produce high levels of RPP. Yeast may be selected which are compatible with eukaryotic cytochrome P450s (Urban et al., Biochimie 72:463–472 (1990)). Polyisoprene biosynthesis results because the substrates of IPP and FPP are synthesized by yeast. The polyisoprene, so made, is then harvested from the cells.

Another means of utilizing this invention is to insert the RPP coding region into the pET3 plasmid vector (Sturdier, et al., Methods in Enzymol 185:60–98 (1990)) downstream of the T7 promoter. The plasmid is then transferred to *E. coli* strain BL21 and allowed to grow for a period of several hours and then is induced to produce T7 polymerase which causes high levels of RPP to be produced. Polyisoprene biosynthesis results when the substrates IPP and FPP are provided in the medium. The polyisoprene, so made, is then harvested from the cells.

The cDNA molecules of this invention can be operatively linked to expression control sequences and used in various eukaryotic or prokaryotic host cells to produce RPP. Suitable expression control sequences include, but are not limited to, the NOS promoter, the CaMV35S promoter, and the GAL 1 and GAL 10 promoters.

As a nonlimiting specific example of the invention, the RPP gene was expressed in transgenic tobacco. A 12.8 kb binary vector was constructed with the RPP gene downstream of the 35S promoter and upstream of the NOS terminator. That vector, named pBIRPP (FIG. 7), was mobilized into *Agrobacterium tumefaciens* strain LBA 4404 which was used to transform tobacco cv. Samsun plants. A second construct containing RPP in the antisense orientation was also prepared. Transformed tobacco plants were selected on kanamycin and grown to maturity. Analyses revealed the presence and expression of the foreign RPP gene (FIG. 8) in transformed tobacco plants. SDS gels (FIG. 8A) of total tobacco proteins showed the presence of RPP (arrow) in 4 different transformants (#3, #6, #14, and #17) and its absence in non-transformed, control (C) and antisense (A) tobacco. A Western hybridization of an identical gel (FIG. 8B) probed with a mono-specific RPP-antibody showed a single RPP band (arrow) in each of the sense constructs (#3, #6, #14, #17) and its absence in control (C) and antisense (A) tobacco constructs.

Figure 9C:

Since it was established that the transformed tobacco plants produced RPP, their tissues were examined microscopically and evidence of polyisoprene production was observed. Electron microscopy is the most sensitive means of detecting lipophilic rubber particles. Electron micrographs of tobacco stems revealed that lipophilic polyisoprene particles were not produced in non-transformed, control plants (FIG. 9A) but were produced in transformed plants (FIGS. 9B and 9C). The tobacco lipophilic particles (arrows) bear a striking resemblance to guayule rubber particles (Backhaus and Walsh, Bot Gaz. 144: 391–400 (1983)) and occur primarily in plant vacuoles. This is the first report of polyisoprene particle accumulation in a non-rubber producing plant due to transgene manipulation.

Figure 10B:
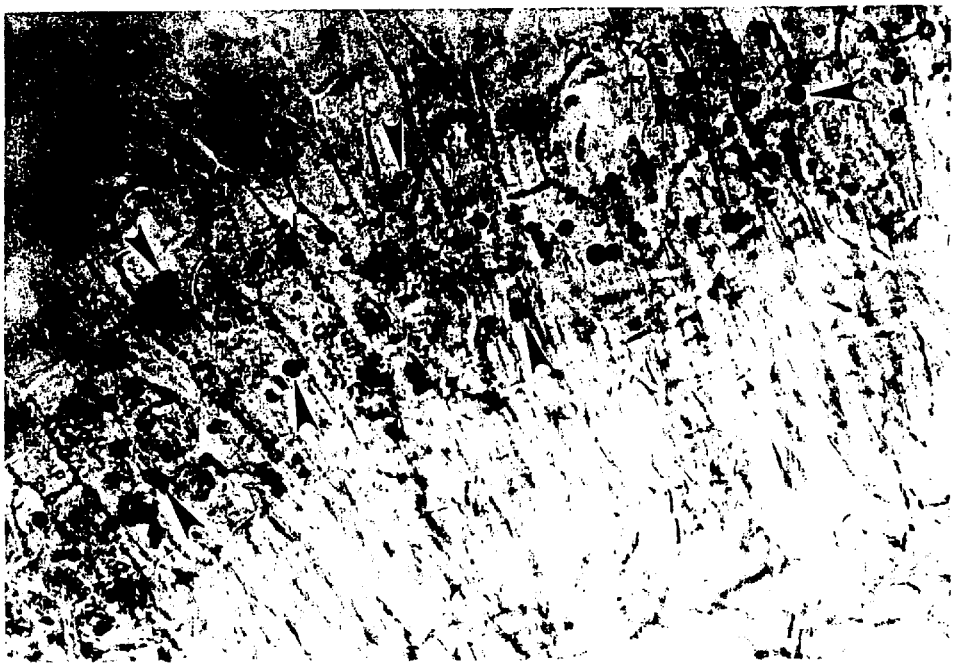

Further verification for polyisoprene production in transgenic tobacco was obtained by light microscopy using a highly specific stain for rubber (Addicott, Stain Technol. 19:99–102 (1944)). This stain is only effective when relatively high concentrations of rubber are produced in the tissues. Again, as with the electron micrographs, light micrographs show no polyisoprene particles in cells of non-transformed plants (FIG. 10A), but show abundant particles in cells of transformed plants (FIG. 10B). The particles appear as dark blue staining globules within the cells (arrows). These particle producing cells are not distributed uniformly throughout the plant, but are concentrated in the outer layers of the stem. It is believed that these cells produce certain precursors that are needed for polyisoprene synthesis. Regardless, it is clear that RPP is crucial for eliciting polyisoprene biosynthesis in this species.

5.3 RPP IS A SPECIES OF AOS

Rubber particle protein (RPP) is a species of allene oxide synthase (AOS) and not a prenyltransferase. A computer based search using the WORD, FASTA and TFASTA algorithms was not able to identify significant homology to the pRPP30 sequence with any of the known prenytransferease sequences in the GENBANK/EMBL and SWISSPROT databanks. Direct comparison to published sequences for the Hevea rubber elongation factor (Dennis and Light, J. Biol. Chem. 264: 18618–18626 (1989); Attanyaka et al., Plant Mol. Biol. 16: 1079–1081 (1991); Goyvaerts et al., Plant Physiol. 97:317–321 (1991)) also showed no homology. Although it was anticipated that RPP would share homology or structural domains to one or more of the known prenyltransferases (Kuntz et al., Plant J. 2:25–34 (1992)), this proved negative. Sequence comparison using the BLAST algorithm (Altschul et al., J. Mol. Biol. 215: 403–410, (1990)) finally revealed significant homology to portions of several cytochrome P450s. Small regions of homology to RPP were detected in the two conserved "B" and "C" domains of P450s (Kalb and Loper, Proc. Natl. Acad. Sci. USA 85: 7221–7225 (1988)) but RPP lacked homology to the "A" and "D" domains. The highly conserved "D" domain is especially critical for most P450s. This apparent structural anomaly was resolved when the sequence for another unusual P450, allene oxide synthase (AOS), from flaxseed, was published (Song et al., Proc. Natl. Acad. Sci. U.S.A., 90: 8519–8523 (1993)).

Comparison of RPP and AOS (FIG. 5) shows over 65% homology and 85% similarity between the two protein sequences. Both have several structural features in common, especially their unusual heme-binding site within the "D" domain. However, unlike AOS, RPP does not possess a transit signal peptide and AOS is thought to be localized in plastids while RPP is not. This difference in N-termini may explain why RPP is localized in rubber particles and not in plastids. Allene oxide synthase is a non-monooxygenase type of P450 that is responsible for epoxide formation in lipids (Song and Brash, Science, 253: 781–783 (1991); Lau, et al., Biochem., 32: 1945–1950 (1993); Vick, In Lipid Metabolism in Plants, T. S. Moore, Ed. (CRC Press, Boca Raton, p. 167–191 (1993); Zimmerman, Biochem. Biophys. Res. Comm. 23:398–403 (1966); Zimmerman and Feng, Lipids 13:313–316 (1978); Zimmerman and Vick, Plant. Physiol. 46:445–453 (1970)). Its function in those plants is believed to be involved with the production of prostaglandin-like compounds in plants, such as jasmonic acid.

Figure 6A:
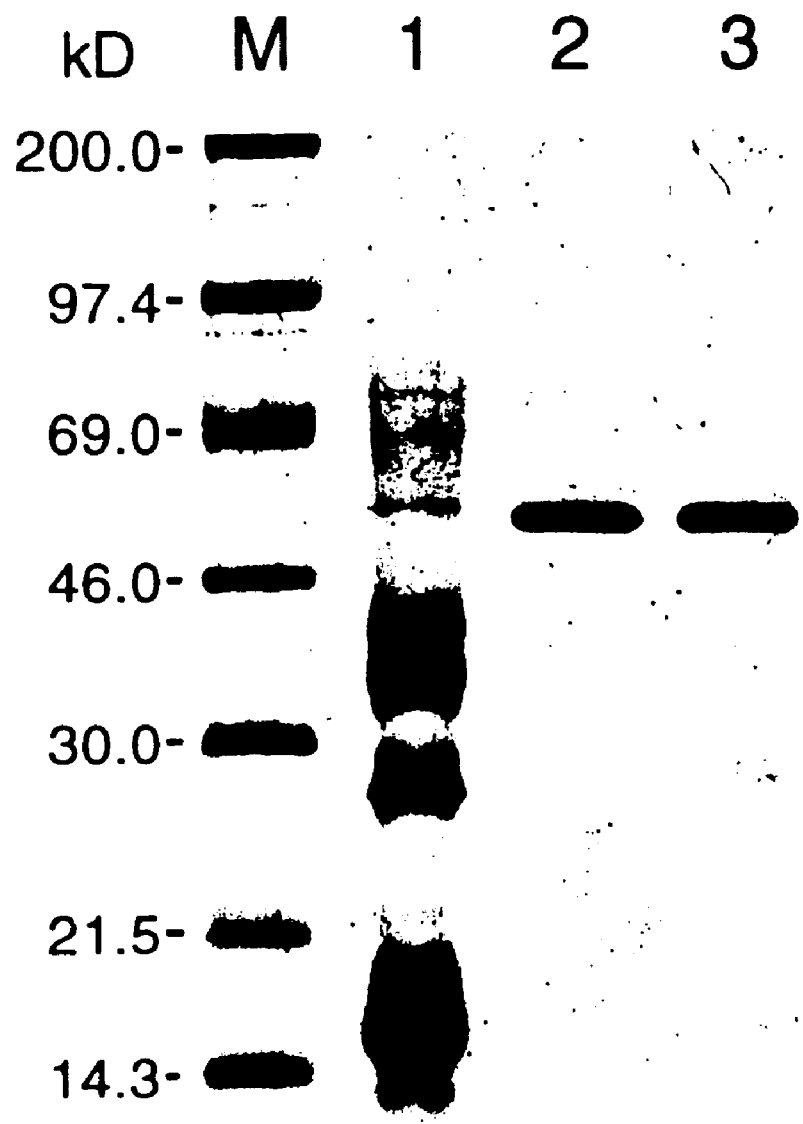
Figure 6B:
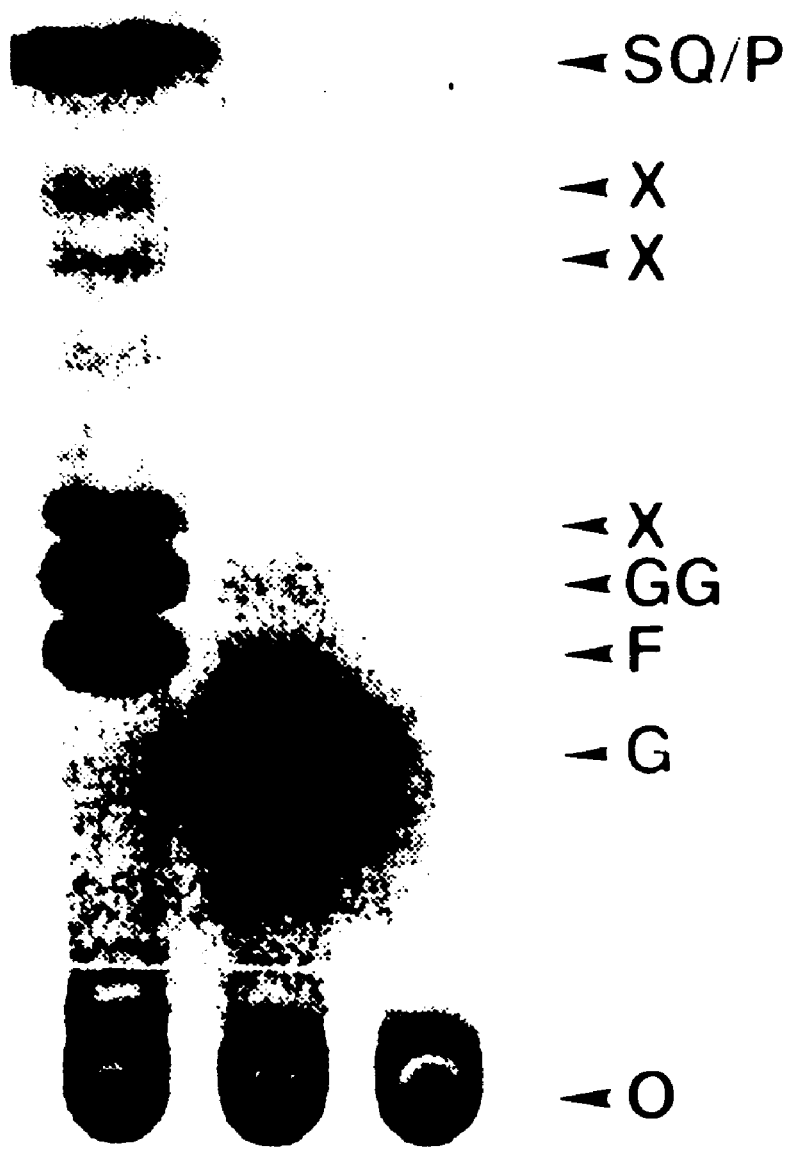

Biochemical analyses were performed on RPP purified from rubber particles. Three-times-washed rubber particles were prepared by centrifugation according to Cornish and Backhaus, op cit. (1990) from a crude homogenate of guayule stembark. RPP was solubilized by sonicating washed particles in 0.5% CHAPS and passing that solution through a 0.22 $\mu$m filter to remove remaining rubber particles. Protein gels revealed the extent of purification for each of the steps from crude homogenate (FIG. 6A, lane 1), to washed rubber particles (FIG. 6A, lane 2) to the final filtered, CHAPS extract (FIG. 6A, lane 3). Prenyltransferase activity was determined for each purification step by measuring the incorporation of $^{14}$C-isopentenyl pyrophosphate into isoprenoid derivatives that were analyzed by TLC (benzene/ethyl acetate, 90/10) and autoradiography (Dogbo and Camara, Plant Sci. 49: 103–109 (1987); Kuntz et al., Plant J. 2:25–34 (1992)). Dimethylallyl pyrophosphate (DMAPP) was used as the initiator to measure activity in 100 μl aliquots of proteins from each of the three steps (FIG. 6B, lanes 1–3). TLC analysis revealed the complete absence of prenyltransferase activity in the filtered RPP preparations, in which all of the rubber particles had been removed. However, prenyltransferase activity was present in both the crude homogenate and washed preparations containing rubber particles (cf. FIG. 6B, lane 3 with lanes 1 and 2). These prenyltransferases synthesized several isoprenoid derivatives including geranyl pyrophosphate, farnesyl pyrophosphate, geranylgeranyl pyrophosphate, phytoene, squalene and other unidentified, higher order isoprenes. However no isoprenoids of any kind were produced by the CHAPS-solubilized, filtered preparations of RPP (FIG. 6B, lane 3).

Figure 6D:
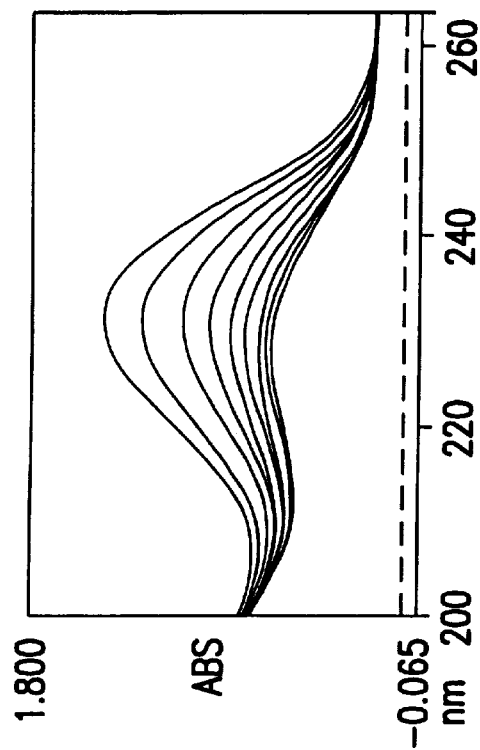
Figure 6C:
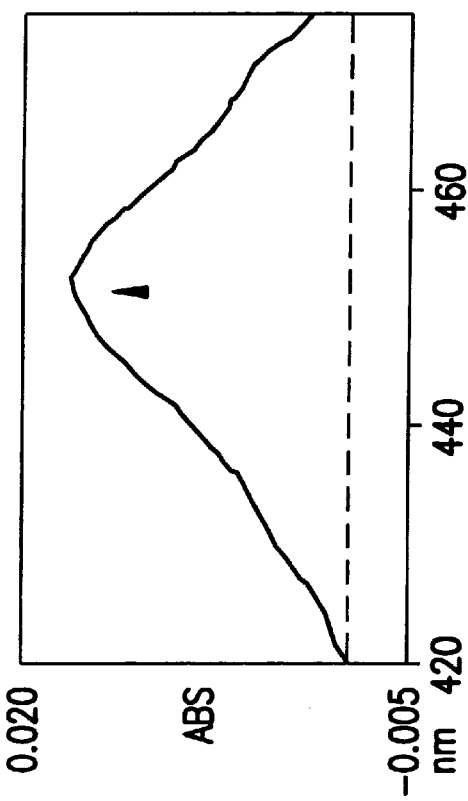

Spectral analysis of this CHAPS-solubilized, filtered RPP preparation revealed that RPP was a cytochrome P450. A difference spectra of this extract clearly indicated a characteristic peak at 450 nm (arrow, FIG. 6C). To confirm that RPP was an allene oxide synthase, an aliquot of this preparation was used in an assay that measured the degradation of linoleic hydroperoxide (LOOH) which has an absorbance maximum at 234 nm. This substrate was prepared according to Zimmerman (Zimmerman, Biochem. Biophys. Res. Comm. 23:398–403 (1966); Zimmerman and Feng, Lipids 13:313–316 (1978); Zimmerman and Vick, Plant. Physiol. 46:445–453 (1970)). The reaction was initiated by the addition of pure RPP to a cuvette containing LOOH and then scanning the cuvette with a series of UV spectra at 10 sec intervals (Song and Brash, Science 253: 781–784 (1991)). Results showed that purified RPP had high AOS activity (FIG. 6D). This biochemical activity was similar to the activity of flaxseed AOS and was consistent with sequence data suggesting similar functions for the two proteins. Furthermore, the data clearly showed that RPP was not a prenyltransferase. Further enzymatic analysis of protein extracts prepared from control (C) and transformed (#3) tobacco showed that strong AOS activity, due to the expression and production of functional RPP from the foreign gene, was present only in transformed tobacco (FIG. 8D) and was completely absent in control tobacco (FIG. 8C). Because control plants do not contain the RPP gene and do not produce any functional RPP enzyme they are unable to metabolize LOOH. The UV scans of extracts prepared from transgenic tobacco, however, reveal that they possess high AOS activity because they express the recombinant RPP gene.

5.4 USES OF RPP AND OTHER AOS ENZYMES

The molecules of the present invention have a number of utilities. Rubber particles may act as deterrent to disease, herbivor or insect attack (Archer and Audley, Rubber, gutta percha and chicle In: Nord F F, Miller L P (eds) Phytochemistry, Van Nostrand-Reinhold, New York, vol. 2, p. 310–343 (1973)). It is noteworthy that the non-polar, neutral lipids in rubber particles can serve as lipid hydroperoxide precursors for reactions catalyzed by AOS. Lipid hydroperoxides are generated when lipoxygenase reacts with unsaturated lipids having a cis,cis-1-4-pentadiene configuration. GC and oxygen consumption experiments have shown that these fatty acids are present and can be released when particles are exposed to exogenous lipase and oxidized by lipoxygenase (FIG. 14). The products of these reactions are known signaling intermediates that induce defense related responses (Farmer, Plant Mol. Biol. 26:1423–1437 (1994); Gardner, HortScience 30:197–205 (1995)). In most plants the source of these fatty acids is usually attributed to membrane phospholipids. However, in rubber-containing plants, it is now evident that rubber particles may provide the lipids needed for such defense related activities. Our earlier discovery, that AOS is the most abundant protein of guayule rubber particles, supports this hypothesis.

Allene oxide synthase (EC4.2.1.92) comprises 40% of the protein in rubber particles from the guayule plant (Pan et al., J. Biol. Chem. 270: 8487–8494 (1995)). In most other plants, AOS controls jasmonic acid (JA) synthesis of the oxylipin pathway and regulates the hormonal activity associated with JA. AOS is not usually required in large quantities as this could disturb the hormone balance of compounds (i.e. JA and methyl-JA) that are used at low levels. It is surprising therefore, to find such high levels of AOS in guayule where rubber particles account for upwards of 10% of the dry weight of the plant and AOS is equal to 0.4% of this. In addition to its crucial role in rubber biosynthesis, it is now recognized that AOS has a second crucial role as an antioxidant.

In various specific, nonlimiting embodiments, the present invention provides for the following:

(1) the use of an allene oxide synthase as a preservative of plant seeds;

(2) the use of an allene oxide synthase as a treatment of trauma patients with severe blood loss;

(3) the use of an allene oxide synthase as a promoter of apoptosis in the treatment of plants and animals for certain diseases;

(4) the use of an allene oxide synthase in tobacco plants to make the tobacco plants resistant to oxidative herbicides, such as paraquat;

(5) the use of an allene oxide synthase to increase the effective life span of sperm used for artificial insemination or in vitro fertilization; and (6) the use of allene oxide synthase to increase the average and maximum life span of biological organisms, such as fruit flies.

In a nonlimiting embodiment, Applicants have inserted RPP gene in a vector, and have expressed and purified an effective amount of RPP enzyme as discussed in greater detail above. The resulting purified RPP protein is then mixed with a suitable buffer and targeted sperm. A suitable buffer is selected compatible with RPP, having a pH of 5 or greater, and compatible with the targeted sperm. The buffer's compatibility with the sperm will vary according to the type of sperm selected. By way of non-limiting example, a suitable buffer is citrate, having a pH of 7. The RPP and sperm are mixed in the buffer resulting in the advantages of increasing the likelihood of successful fertilization or insemination by extending the effective life span of the sperm, increasing the likelihood of successful fertilization or insemination by requiring a smaller sample of viable sperm, and increasing the likelihood of successful fertilization or insemination after a sample of sperm has been frozen and thawed.

These and still further objects as shall hereinafter appear are readily fulfilled by the present invention in a remarkably unexpected manner as will be readily discerned from the following detailed description of an exemplary embodiment thereof, especially when read in conjunction with the accompanying drawings.

6. EXAMPLE

DNA SEQUENCING OF cDNA ENCODING GUAYULE RUBBER PARTICLE PROTEIN

6.1 PURIFICATION AND CNBr CLEAVAGE OF RPP

The source of RPP is from purified rubber particles which are isolated from guayule line 11591 stembark tissues by the procedure described by Cornish and Backhaus, Phytochem. 29: 3809–3813 (1990) and Backhaus et al., Phytochem. 30: 2493–2497 (1991). Purified rubber particles are subjected to preparative SDS-PAGE to purify RPP, which is observed in the gel as a protein band migrating with an apparent molecular weight of 48,500–53,500 Daltons. RPP is purified from gel bands by electroelution using a Model 422 Electroeluter (Bio-Rad) according to manufacturer's instructions.

Purified RPP equivalent to at least 1000 pmoles was taken to dryness by lyophilization and dissolved in 150 μl 70% formic acid in an Eppendorf tube. To this 100 μl of 70 μg/mL CNBr in 70% formic acid was added. The mixture was incubated in the dark at room temperature for 24 hours. The CNBr digested RPP was subjected to SDS-PAGE using a 16% acrylamide gel in a Tris-Tricine, 3-layer system as described by Schagger and Von Jagow, Anal. Biochem. 166:368–379, (1987). Following electrophoresis, protein fragments were blotted onto PVDF (Millipore) membranes and visualized according to the method of Ploug et al. Anal. Biochem. 181:33–39, (1989). Areas of PVDF membranes containing stained peptides were excised and submitted for N-terminal amino acid sequencing (Univ. Calif. Davis, Protein Structure Lab). The results of amino acid sequencing of 4 distinct peptides fragments of RPP (SEQ ID NOS: 1–4) is shown in FIG. 1.

6.2 ISOLATION OF GUAYULE STEMBARK mRNA

Guayule stembark (10 g) was cut into 1 cm pieces and homogenized in 2 vol of guanidine buffer (8 M guanidine HCL, 20 mM MES pH 7, 20 mM EDTA, 50 mM mercaptoethanol) in a polytron for 2 minutes. The homogenate was extracted with 1 vol of phenol:chloroform and centrifuged for 45 minutes at 10,000 rpm (Sorval SS-34 rotor) at 15C. The aqueous phase was transferred to a fresh tube and centrifuged for 10 min at 10,000 rpm at 15C. and the supernatant transferred to fresh tube. To this 0.7 vol of pre-cooled 100% ethanol and 0.2 vol of 1 M acetic acid was added. The sample stored at −20° C. overnight. The RNA was recovered by centrifugation for 10 min at 5,000 rpm at 4° C. The pellet was washed with sterile 3M sodium acetate (pH 5.2) at room temperature and centrifuged for 5 min at 10,000 rpm. The pellet was washed with 70% ethanol, vacuum dried and dissolved in sterile water. Poly-A+ mRNA was purified from RNA by fractionation on oligo-dT cellulose according to methods described in Sambrook et al., Molecular Cloning, A Laboratory Manual, 2nd Ed. 7.26–7.29 (1989).

6.3 CONSTRUCTION OF GUAYULE STEMBARK cDNA LIBRARIES

Guayule stembark mRNA was used to generate cDNA for construction of libraries in lambda ZAP, available in kit form from Strategene Inc., according to the protocol outlined by the manufacturer. Lambda ZAP is described by Short et al., Nucl., Acids Res. 16:7583–7600 (1988).

6.4 PCR AMPLIFICATION OF GUAYULE RPP cDNA

The guayule stembark cDNA libraries were initially screened with the 92 bp probe, sequence P5/6 (FIG. 2 SEQ ID NO: 11) generated by PCR amplification of guayule cDNA. The first strand cDNA synthesis was performed by using the Strategene, cDNA synthesis kit and following the manufacturer's instructions. About 1.5 μg of guayule stembark mRNA was incubated at 37° C. for 1 h in the presence of oligo-dT, reverse transcriptase and a mixture of nucleotides. The single stranded cDNA was precipitated by adding ammonium acetate (pH 4.5) to a final concentration of 0.5 M followed by 2 vols of ethanol. The mixture was centrifuged in a microcentrifuge at 14,000 rpm at room temperature for 10 min and the pellet was washed with 200 μl of 70% ethanol, dried under vacuum and redissolved in 50 μl of sterile water.

Sequence PS (FIG. 2 SEQ ID NO: 5), a degenerate, 20-mer oligonucleotide primer corresponding to a sense strand DNA of CNBr fragment #3 SEQ ID NO: 3 and sequence P6 (FIG. 2 SEQ ID NO: 6), a degenerate, 20-mer oligonucleotide primer corresponding to an antisense strand DNA of CNBr fragment #3 SEQ ID NO: 3 (FIG. 1) were used to generate the 92 bp P5/6 sequence (FIG. 2 SEQ ID NO: 11). A 20 μl PCR reaction mixture containing 100 pmol of each primer, 1 μl of the cDNA mixture described above, 0.2 mM of each nucleotide and 0.5 μl REPLINASE (DuPont) in 50 mM Tris-HCl buffer (pH 9.0) containing 20 mM ammonium sulfate and 1.5 mM magnesium chloride was amplified under a thermocycling regime of 94° C. for 1 min, 55° C. for 2 min and 72° C. for 3 min for 39 cycles followed by 10 min at 72° C. The resulting mixture was run on an agarose gel to reveal a 92 bp fragment. DNA sequence analysis of the fragment revealed an exact match to the amino acid sequence of CNBr fragment #3 as shown in FIGS. 2 and 3.

Subsequent to this, radioactively labeled $^{32}P$ probes of P5/6 were regenerated by the PCR reaction, using 50 pmol of each primer P5 and P6 and utilizing the purified P5/6 probe as the template DNA. This resulted in high specific activity probe which was used to screen the lambda ZAP cDNA library, according to the methods outlined in Sambrook, et al. (op cit).

Subsequent to determining the sequence of the pRPP30 clone it was discovered that P5/6 encodes a 3' terminal region of the RPP gene (FIG. 3). Thus, when screening the cDNA library with P5/6 it resulted in the preferential isolation of only partial cDNA clones less than 900 bp in length. A few of these partial cDNA's were used, in turn, to isolate the full-length, pRPP30 cDNA clone (FIG. 3).

6.5 SCREENING OF cDNA LIBRARIES

Plaques containing recombinant lambda ZAP cDNA's were transferred to membrane filters (Colony/Plaque Screen, DuPont) and subjected to an initial screening by hybridization to radioactively labeled P5/6 in 6×SSPC, 5×Denhardt's solution, 50% formamide, 0.5% SDS, 200 μg/ml salmon sperm DNA, and 10% dextran sulfate for 18 h at 42° C. Washes were for 2 times at 10 min in 2×SSC followed by 2 times at 20 min in 2×SSC plus 0.1% SDS. Positive plaques from the initial screen were rescreened on nitrocellulose (Schleicher and Schuell) by hybridization to radioactively labeled P5/6 in 6×SSPE, 5×Denhardt's solution, 0.5% SDS and 100 μg/ml salmon sperm DNA for 18 h at 42° C. and washed the same as for the initial screens.

Clones which yielded positive responses to the second screen were then subjected to excision and circularization according to the lambda ZAP protocol. Phagemid DNA was isolated by standard miniprep procedures and separated on agarose gels. Those colonies resulting in Bluescript phagemid containing the largest cDNA inserts were further characterized by DNA sequencing.

6.6 DNA SEQUENCING

DNA sequencing employed the dideoxy chain termination technique, utilizing SEQUENASE (U.S. Biochemical Corp) according to manufacturer's instructions.

The cleavage of RPP by CNBr resulted in four distinct peptide fragments which could be sequenced from their N-termini (FIG. 1 SEQ ID NO: 1–4, respectively). Amino acid sequences ranged from 17 to 36 residues in length. Of those, peptide fragments #3, #4, and #2 resulted in deduced DNA stretches of at least 17 bp with low degeneracy (FIG. 2). Oligonucleotides corresponding to those portions were synthesized and used to generate larger guayule cDNA fragments by PCR amplification. Of those, two successful PCR products were made. A 92 bp sequence, P5/6 SEQ ID NO: 11 which matched with the known CNBr fragment #3 (FIG. 2 SEQ ID NO: 3) and a 434 bp sequence, between primers P1 SEQ ID NO: 7 and P9 SEQ ID NO: 4 (FIG. 3) which contained regions of the RPP gene bridging CNBr fragments #4 SEQ ID NO: 4 and #2 SEQ ID NO: 2. Sequence P5/6 was used as a probe to successfully isolate a large cDNA clone designated cl7 which contained an 823 bp insert coding for the 3' end of the RPP gene (not shown).

Full-length cDNA clones were isolated by screening against both the 92 bp probe and the 434 bp probe. Analysis of the full-length pRPP30 reveals an open reading frame (FIG. 3.) which contains 8 methionines at positions 1, 44, 56, 97, 129, 252, 327 and 371, and 2 cysteines, at positions 274 and 426. The pRPP30 polypeptide also contains 3 possible N-linked glycosylation sites at positions 132, 318 and 354. This is consistent with the structure of guayule RPP which is known to be a glycoprotein. The pRPP30 coding region is negatively charged with a deduced pKa of 6.15 which agrees with the experimentally derived value of 6.2. The pRPP30 clone contains a TGA stop codon and a 3' noncoding sequence of 250 bp which is AT-rich as expected for a termination sequence. The 5' noncoding region contains 23 bp and a consensus plant gene translation start site.

A computer search of GENBANK/EMBL and SWIS-SPROT using the BLAST algorithm showed homology to small dispersed regions of several cytochrome P450 with amino acid sequences of the 473 amino acid pRPP30 open reading frame. Later it was discovered that the RPP protein sequence showed considerable homology to the flaxseed AOS sequence (Song et al. op cit. (1993)).

6.7 ANALYSES OF RPP AS A CYTOCHROME P450

To verify that RPP had properties of an AOS-type cytochrome P450 it was subjected to spectral and biochemical analyses according to Song and Brash, op cit. (1991) and Zimmerman, op cit. (1966); Zimmerman and Vick, op cit. (1970) and Zimmerman and Feng, op cit. (1978)

6.8 BIOCHEMICAL ANALYSIS OF PRENYLTRANSFERASE ACTIVITY

Washed rubber particles were prepared by centrifugation according to Cornish and Backhaus, op cit.(1990) from a crude homogenate of guayule stembark. RPP was solubilized by sonicating washed particles in 0.5% CHAPS and passing that solution through a Millipore, Millex-GV, 0.22 μm, SLGV filter which removed all of the remaining rubber particles. Prenyltransferase activity was determined for each purification step by measuring the incorporation of $^{14}$C-isopentenyl pyrophosphate into isoprenoid derivatives according to Dogbo and Camara, op cit. (1987) and Kuntz et al., op cit. (1992) using dimethylallyl pyrophosphate (DMAPP) as the initiator to measure activity in 100 μl aliquots of protein extract.

7. EXAMPLE

RECOMBINANT EXPRESSION OF RUBBER PARTICLE PROTEIN

7.1 CONSTRUCTION OF THE pBIRPP BINARY VECTOR

One means of using this invention is to insert the RPP coding region into the pBI121 binary plasmid vector (Jefferson et al., EMBO J. 6: 3901–3907 (1986)) downstream of the 35S promoter. This recombinant plasmid is transferred to *Agrobacterium tumefaciens* strain LBA 4404 where it is used to inoculate one of numerous plant species, such as tobacco, sunflower or guayule. The RPP coding region containing the 35S promoter is then incorporated into the plant's chromosomal DNA and the plant is replicated. The resulting transformed plant then produces large quantities of RPP which, in turn, leads to polyisoprene biosynthesis in its cells. Polyisoprene synthesis occurs because the substrates (IPP, DMAPP, FPP and Mg, etc.) are present within all plants. The polyisoprene so made is then harvested from the plant tissues.

Tobacco transformation was performed using a binary vector derived from pBI121 in which the GUS gene was replaced with RPP downstream of the strong CaMV 35S promoter. This new vector was constructed by first digesting pBI121 with SmaI and SstI to remove the 1.9 kb GUS insert and filling in the SstI site with T4 polymerase. The resulting linear 10 kb fragment was gel purified and circularized by blunt end ligatation. This gave a circular GUS– minus pBI121. This was then cut with BamHI, filled in with Klenow and cut again with XbaI. The linear fragment containing one sticky XbaI end and another filled in BamHI blunt end was gel purified. Concurrently, the pRPP30 insert in the SK⁻ vector was digested with XhoI and filled in with Klenow. This linearized plasmid was then digested with XbaI to give an RPP fragment with one sticky XbaI site at the 5' end of RPP and a blunt 3' end. This was ligated to the complementary GUS– minus fragment to yield a 12.8 kb, pBIRPP binary plasmid vector containing the RPP gene in a sense orientation downstream of the CaMV 35S promoter (FIG. 7). Tobacco plants are transformed by the leaf disk method (Horsch et al., Science, 227:1229–1231 (1985)) selected, and grown to maturity.

7.2 MICROSCOPIC ANALYSIS OF TRANSFORMED TOBACCO

Transgenic tobacco plants were analyzed by light microscopy following the staining of tissue sections by the method of Addicott, op cit. (1944) or by electron microscopy according to the method of Backhaus and Walsh, op cit. (1983).

8. EXAMPLE: LIPIDS AND PROTEINS FROM GUAYULE RUBBER PARTICLES

To better understand the role of AOS in the guayule plant, rubber particles were analyzed for lipids that can serve as precursors for this enzyme. It is shown that non-lipids comprise 5% of rubber particle weight and include lipids that could serve as precursors for AOS. Rubber particles contain lipids that are similar to those found in seed oil bodies from other species. These include triacylglycerol (TAG) and quantities of polar lipids sufficient to form a membrane monolayer around rubber particles. However, the phospholipid and protein composition of rubber particles differs from seed oil bodies. Rubber particles lack phosphatidylcholine (PC) and do not contain oleosins, specific markers of seed oil bodies. Although rubber particles and seed oil bodies exhibit similar physical attributes and possess a number of similar lipids, their protein components are unique, suggesting divergent cellular functions. Lipid precursors for the enzyme RPP were identified.

8.1 MATERIALS AND METHODS

8.1.1 ISOLATION OF LIPOPHILIC STRUCTURES

Guayule rubber particles were isolated and washed according to Cornish and Backhaus, Phytochemistry 29:3809–3813 (1990). For long term storage, glycerol was added to the rubber suspensions at a 5% (w/v) final concentration before freezing at −196° C. Cucumber oil bodies were isolated in a like manner from germinating cucumber seeds and were used immediately. Hevea rubber particle preparations were kindly supplied by K. Cornish (USDA, Albany, Calif.).

8.1.2 ISOLATION OF LIPIDS

Lipids were extracted from washed rubber particles and cucumber oil bodies using a modified procedure of Malshet et al., Lipids 9:328–332 (1974). A 0.5 ml suspension of washed rubber particles or oil bodies was extracted with 0.75 ml chloroform:methanol (2:1, v/v). After 2 min vortexing at maximum speed, the extract was centrifuged at 16,000×g at room temperature for 4 min. The upper aqueous layer was discarded and the lower chloroform layer was dried under nitrogen to afford a dried rubber and lipid coagulum. This was extracted with 0.4 ml of acetone, vortexed for 2 min, centrifuged 4 min at 16,000×g and the acetone containing the dissolved lipids was removed from the rubber coagulum and transferred to a fresh tube. The acetone extract was again dried under nitrogen and the lipids were redissolved in chloroform and stored at −20° C.

The quantity of rubber and lipid (neutral plus polar lipids) was determined on weighed samples of rubber particles and oil bodies. Rubber content was determined by adding 5 volumes of chloroform:methanol (2:1, v/v) to the suspension and vigorously shaking the mixture to form a coagulum that was trapped, dried and weighted on a preweighed filter (Whatman #1). Total lipids were determined in the remaining chloroform:methanol extract by adding a ⅕ volume of a 0.6% NaCl solution to the suspensions to separate the phases which were then clarified by a 5 min centrifugation at 173×g. The organic phase was transferred to a fresh tube, dried under nitrogen gas and weighed. The proportion of polar to neutral lipids was determined gravimetrically according to Kates, Techniques of Lipidology: Isolation, Analysis and Identification of Lipids, Laboratory techniques in biochemistry and molecular biology, Vol. 3 part 2, Elsevier Laboratory, New York p.464 (1986) by precipitating the chloroform extract with cold acetone.

8.1.3 LIPID ANALYSIS

Total lipids isolated from rubber particles and oil bodies were spotted onto silica gel 60 TLC plates (Sigma T-6270) and run according to Yao, et al., Proc. Natl Acad. Sci USA 88:2269–2273 (1991). Lipids were identified by comparison to known lipid standards and specific staining reactions on TLC according to Kates, Techniques of Lipidology: Isolation, Analysis and Identification of Lipids, Laboratory techniques in biochemistry and molecular biology, Vol. 3 part 2, Elsevier Laboratory, New York p.464 (1986). Routine staining on TLC was by iodine vapor. Neutral lipids from rubber particles were also analyzed according to previous methods (Hasma and Subramaniam, J. Nat. Rubb. Res. 1:30–40 (1986); Ho et al., Proc. Int. Rubb. Conf. Kuala Lumpur 4:441–456, (1975); Hasma, J. Rubb. Res. 6:105–114 (1991)). The absence of tocopherols in guayule particles was verified by $SbCl_5$ staining according to Stahl, Thin Layer Chromatography: A laboratory handbook, Springer-Verlag, New York, p. 1125 (1969). The presence of PE and PS was confirmed by ninhydrin staining and PI, PG/PS, PE and PA were positively identified using Rhodamine 6G (Kates, Techniques of Lipidology: Isolation, Analysis and Identification of Lipids, Laboratory techniques in biochemistry and molecular biology, Vol. 3 part 2, Elsevier Laboratory, New York p. 464 (1986)) and comparing to known standards.

The quantity of individual lipids was determined by charring and scanning densitometry (Blank et al., J Amer Oil Chem Soc 41: 371–377, 1964). TLC plates were developed by spraying with a saturated solution of potassium dichromate in 70% $H_2SO_4$ and heating 25 min at 100° C. The permanent char spots were analyzed by scanning densitometry of the plates using the GS365W software package (Hoefer Scientific).

8.1.4 GAS CHROMATOGRAPHIC ANALYSIS

Extracted lipids were methylated according to Christie, Lipid Analysis-Isolation separation, identification and structural analysis, Pergamon Press, Oxford p. 476 (1982). GC analysis was performed using Hewlett Packard HP5840A gas chromatograph with Omegawax 320 column, 30 m long, 0.32 mm diameter at 190° C. Fatty acid components were identified by comparison to fatty acid methyl ester standards (Sigma #189-1) containing equal amounts of methyl esters of palmitic acid (16:0); stearic acid (18:0); oleic acid (18:1); linoleic acid (18:2) and linolenic acid (18:3).

8.1.5 OXYGEN CONSUMPTION FOLLOWING LIPASE AND LIPOXYGENASE TREATMENT OF GUAYULE RUBBER PARTICLES

To assay rubber particles for lipids that could act as precursors for AOS, we examined oxygen uptake following lipase treatment of particles in the presence of lipoxygenase. A suspension of freshly prepared guayule rubber particles (16 mg rubber) in 200 μl of 50 mM Tris-HCL, pH 8.0 wash buffer was incubated with or without 20 μl of 1 mg ml$^{-1}$ pancreatic lipase (Sigma #L-3126) solution for 1 hr at room temperature. In an oxygen electrode (Yellow Springs Instuments, Yellow Springs, OH) 100 μl of this suspension was added to 2.0 mls 50 mM K phosphate buffer, ph 8.0, containing 60 μl of a 1 mg ml$^{-1}$ soybean lipoxygenase (Sigma #L-8383) solution. Under these conditions, oxygen consumption by lipoxygenase is dependent on the presence of fatty acids released by lipase treatment.

8.1.6 ISOLATION OF PROTEINS

Proteins were extracted by adding 6 ml saturated phenol and 6 ml of protein extraction buffer (0.1 M Tris pH 8.0, 10 mM EDTA, 0.1 M LiCl, 1% SDS) to a 5 ml suspension of washed rubber particles in wash buffer (50 mM potassium phosphate, pH 7.2, 2.5 mM MgCl$_2$, 5 mM DTT). This was shaken vigorously and centrifuged in a swinging bucket rotor for 10 min, 769×g. The aqueous layer and resulting rubber coagulum was discarded and 4 volumes of methanol containing 100 mM ammonium acetate were added to the phenol fraction. This was stored overnight at −20° C. to precipitate proteins which were pelleted by centrifuging 5 min at 11,900×g. Residual phenol was removed from the pelleted protein by 5 additional centrifugations in cold 100 mM ammonium acetate in methanol. Proteins were stored in this solution at −20° C. until needed. Total protein in rubber or oil body suspensions was determined by weighing a dried fraction of the protein suspension from a known quantity of rubber or oil body suspension.

8.1.7 PROTEIN ANALYSIS

Proteins isolated from guayule rubber particles and Brassica and soybean seed oil bodies were separated by SDS-PAGE and stained with Coomassie blue. A separate SDS-PAGE gel of guayule proteins was stained with oil red O according to Mackness and Durrington "Lipoprotein separation and analysis for clinical studies" In Converse C A, Skinner E R (eds) Lipoprotein Analysis: A Practice Approach, IRL Press New York p. 16 (1992) to detect the presence of lipid-containing proteins. Proteins were also electroblotted onto nitrocellulose membranes according to Ploug et al., Anal. Biochem. 181:33–39 (1989) then stained with 0.1% amido black in 25% propanol and 10% acetic acid or immuno-assayed using antibodies to either Brassica oleosins generously supplied by A. H. C. Huang (Tzen et al., Plant Physiol. 101: 267–276 (1990)) or to soybean oleosins graciously provided by E. Herman (Herman, Planta 172: 336–345 (1987)). Blocked membranes were incubated with a dilution of 1:500 Brassica anti-oleosin or 1:2000 soybean anti-oleosin and developed with an alkaline phosphatase-conjugated second antibody. Blots were stained according to manufacturers instructions using an alkaline phophatase immuno-blot assay system (Bio-Rad, Richmond, Calif.).

8.1.8 ISOLECTRIC FOCUSING AND FLUORESCENCE EXCITATION SPECTROSCOPY OF RUBBER PARTICLES

The isoelectric point of Hevea and guayule rubber particles was determined using the protocol for oil bodies of Tzen et al., Plant Physiol 101: 267–276 (1993); except that rubber particles were focused for an additional 15–20 min.

The fluorescent properties of rubber particles and extracted lipids of guayule and Hevea were analyzed according to Yao et al., J. Cell. Biochem. 51: 488–494 (1993), Eldred, Adv. Biosci 64: 23–36 (1987) and Malshet et al., Lipids 9:328–332 (1974) using a FluoroMax spectrofluorometer (JY/SPEX Instr SA, Inc). Chloroform:methanol extracted lipids and the aqueous phase generated during extraction were also separated via TLC and visualized using UV illumination at 366 nm (Eldred, Adv Biosci 64: 23–36, 1987; Eldred and Katz, Possible Mechanism for lipofusinogenesis in the retinal pigment epithelium and other tissues, In: Nagy I (ed) Lipofuscin-1987: State of the Art, Excerpta Medica, New York, pp. 185–211, 1988).

8.2 RESULTS

The major component of guayule and Hevea particles is rubber, (cis 1'-4, polyisoprene) which makes up 88–93% of the particle weight (Table 1). This polymer can be classed as a neutral lipid. In both species the remaining non-rubber, neutral lipids account for 5% and 3%, respectively, of the weight of guayule and Hevea rubber particles. Of this, TAG is the primary non-rubber, neutral lipid. Guayule rubber particles also contain SE that is nearly equal in quantity to TAG. Densitometric estimates from TLC indicate that the non-rubber, neutral lipids of guayule particles contain 34.6% TAG and 23.5% SE (Table 1, FIG. 13). In addition, guayule particles contain 19.9% FFA, 11.9% LCOH and 8.7% S along with smaller amounts of MAG and DAG (Table 1). The non-rubber neutral lipids of Hevea contain 47.4% TAG and 7.5% SE (FIG. 13). Other neutral lipids include 18.9% FFA, 20.6% LCOH, 3.9% S and small quantities of MAG and DAG. The presence of SE in both guayule and Hevea may be less than indicated by densiometric scan, as SE and wax esters (WE) often co-migrate. With the staining procedures employed, it was impossible to resolve SE from WE. In cucumber seed oil bodies, neutral lipids account for 87.8% of their weight. Densitometric estimates indicate that this neutral lipid fraction contains 73.7% TAG, 12.6% FFA, 7.5% LCOH and 6.15% DAG (Table 1, FIG. 13). The amount of SE in cucumber seeds could not be resolved as it was extremely faint and did not migrate away from TAG enough to be scanned as a distinct spot. Thus, on an overall weight basis, guayule and Hevea rubber particles contain 1.7 and 1.4% TAG, respectively, compared to cucumber seed oil bodies which contain 65% TAG. Gas chromatographic analysis revealed that linoleic (18:2) and linolenic (18:3) acid, were the two most abundant fatty acids in both total and neutral lipid fractions.

TABLE 1

Comparison of lipids and proteins found in lipophilic structures from seeds and other plant parts. An "X" indicates that the constituent is present the amount is not given in the reference or cannot be determined.

| Lipophilic Structure Species | NEUTRAL LIPIDS | | | | | POLAR LIPIDS | | | | | | PROTEIN | REFERENCES |
|---|---|---|---|---|---|---|---|---|---|---|---|---|---|
| | Total NL* | TAG | DAG | MAG | Other NL | Total PL† | PE | PC | PI | PS | Other PL | % (w/w)‡ | |
| Seed Oil Bodies | | | | | | | | | | | | | |
| Cucumber | 87.8 | X | 6.15 | | FFA(12.6%) LCOH(7.5%) S, SE | 0.90 | 5 | 95 | | | PA | X 9.0 | Simpson & Nakamura (1989); This study |
| Soybean | 88.1§ | 60–90 | X | X | FFA, S | 0.97 | 15–25 | 45–60 | 14 | | PA(5–12%) GL | 10–32 | Privell et al. (1973); Murphy (1990); This study |
| Safflower | 85.5 | 75.0 | | | | | 15.0 | 57.6 | 24.4 | | | 10.9 | Gurr et al. (1974); Slack et al (1980); Slack & Roughan (9180) |
| Linseed | 74.1 | 92.5 | | | | 1.5 | 2.0 | 77.6 | 17.7 | | | | Stack et al. (1980) |
| Arabidopsis | 90 | 89 | | | | X | 17.2 | 43.0 | 43.0 | | | 8.5 | Murphy (1990) |
| Crambe abyssinica | 75§ | | | | | X | X | X | X | | | 19 | Gurr et al. (1974) |
| Impatiens capensis | 28‖ | | | | | | | | | | GL | | Nozzolillo et al. (9186) |
| Rape | 94.21 | 83–88 | 9.2 | | FFA | 1.97 | 5.9 | 59.9 | 14.0 | 20.2 | | 3.46 | Tzen et al. (1993); Murphy (1990) |
| Mustard | 94.64 | Xφ | 2 | 1 | FFA | 1.60 | 15.5 | 53.1 | 13.1 | 18.3 | | 3.25 | Tzen et al. (1993) |
| Cotton | 96.99 | 81–97 | | | FFA (0.4%) | 1.18 | 4.6 | 58.6 | 18.1 | 18.7 | | 0.63–1.7 | Tzen et al. (1993); Yatsu et al. (1971); Murphy (1991); Chapman & Trelease (1991) |
| Flax | 97.65 | Xφ | | | FFA | 0.90 | 2.8 | 57.2 | 6.9 | 33.1 | | 1.34 | Tzen et al. (1993) |
| Maize | 97.58 | Xφ | 4.0 | | FFA | 0.91 | 8.1 | 64.1 | 7.6 | 20.2 | | 1.43 | Tzen et al. (1993) |
| Peanut | 98.17 | 97 | | | FFA | 0.80 | 5.0 | 61.6 | 8.4 | 25.0 | | 0.94–1.5 | Tzen et al. (1993); Gurr et al. (1974); Murphy (1990) |
| Sesame | 97.37 | Xφ | | | FFA | 0.57 | 15.8 | 41.2 | 20.9 | 22.1 | | 0.59 | Tzen et al. (1993) |
| Castor bean endosperm | | 90 | | | | | | | | | | | Hogge et al. (1991) |
| Daucus caroia | 57 | | | | | 2.5 | | | | | | 7.5 | Murphy (1990) |
| Phaseolus vulgaris | | 92 | | | | 2.3 | | | | | | 5.3 | Murphy (1990) |
| Jojoba** | | 0 | | | FFA (1.5%) | | | | | | | | Grunstone (1990); Wisniak (1977) |
| Fruit Oil Bodies | | | | | | | | | | | | | |
| Palm†† | | 95.3 | 1.9 | 0.5 | FFA | 0.6 | | | | | GL | | George & Arumughan (1995) |
| Olive | 95.0 | X | X | X | FFA, HC | | | | | | | 1.5 | Ferandez Diez (1971); Yang & Chen (1991) |
| Avocado | | 19.96 | 1.29 | 0.78 | FFA | 0.39 | X | X | X | | PG | | Mazlak (1970) |
| Vegetative Oil Bodies | | | | | | | | | | | | | |
| Cabbage | 81‡‡ | | | | | 0.16 | | | | | | 4.0 | Yatsu et al. (1971); Fernandez Diez (1971); Yang & Chen (1991) |
| Chromoplast Globules | | | | | | | | | | | | | |
| Viola | 57 | | | | S, A, Q, C | 4.7 | | | | | | 3.9 | Hansmann & Sittle (1982) |
| Caltha | 74 | | | | S, Q, C | 7.0 | | | | | | X | Sitte et al. (1980) |
| Deteriosomes | | | | | | | | | | | | | |

TABLE 1-continued

Comparison of lipids and proteins found in lipophilic structures from seeds and other plant parts. An "X" indicates that the constituent is present the amount is not given in the reference or cannot be determined.

| Lipophilic Structure Species | NEUTRAL LIPIDS | | | | | POLAR LIPIDS | | | | | PROTEIN | REFERENCES |
|---|---|---|---|---|---|---|---|---|---|---|---|---|
| | Total NL* | TAG | DAG | MAG | Other NL | Total PL† | PE | PC | PI | PS | Other PL | % (w/w)‡ | |
| Bean cotyledon | X | X | X | | S, FFA, HC, | X | X | X | | | PG | X | Yao et al. (1991 lb); MeKegnet et al. (1995) |
| Rat liver | X | 74 | | | FFA, HC | X | X | X | | | | X | Yao et al. (1993) |
| Rubber Particles | | | | | | | | | | | | | |
| Guayule§§ | 5.02 | 34.6 | 6.3 | 5.9 | FFA (19.9%) LCOG(11.5%) SE(23.5%) S(8.7%) | 0.73 | 32.1 | — | 14.8 | 40.6 | PA(12.5%) | 1.0 | This study |
| Hevea‖ | 1.09 | 63.6 | | | FFA, HC, SE S, LCOH, TC | 0.78 | 21.7 | 56.5 | 21.7 | — | GL, PA | 1.0 | Hasma & Subramaniam(1986); Ho et al.(1975); Hasma(1991); Dennis & Light(1989) |
| Hevea¶¶ | 3.0 | 47.4 | 2.2 | 4.0 | FFA(18.9%) LCOH(20.6%) SE(7/5%) S(3.9%) | 0.74 | 12.4 | trace | 11.8 | 71.5 | PA(4.6%) | 1.0 | This study |

*The values indicate the percentage (w/w) of total neutral lipids (NL) present in lipophilic structures. The percentage of total NL as triacylglycerol (TAG), diacylglycerol (DAG), or monoacylglycerol (MAG) is indicated. Other NL include free fatty acids (FFA), hydrocarbons (HC), wax ester (WE), sterols (S), sterol esters (SE), carotenoids (C), alkanes (A), quinones (Q), long chain alcohols (LCOH) and tocopherols (TC).
†The values indicate the percentage (w/w) of total polar lipids (PL) present in the lipophilic structures. The percentage of total PL as phosphatidylethanolamine (PE), phosphatidylcholine (PC), phosphatidylinositol (PI), phosphatidylserine (PS) or other PL are indicated as glycolipid (GL), phosphatidylglycerol (PG) or phosphotidic acid (PA).
‡The values indicate the percentage (w/w) of total proteins present in the lipophilic structures.
§Data represents the percentage (w/w) of total NL in seeds, oil bodies were not isolated and extracted before analysis.
‖Data represents the percent fresh weight (w/w) of total lipids in seeds, oil bodies were not isolated and extracted before analysis.
¶NL is primarily TAG
**Data derived from analysis of "wax" bodies isolated from jojoba seeds.
††Data taken from 24 week post anthesis fruit.
‡‡This value represents the percentage (w/w) of total NL found in cabbage leaf oil bodies.
§§The values represent the percent dry weight (w/w) of the rubber particles. Rubber accounted for 93% of this dry weight.
‖‖The values represent the percent dry weight (w/w) of the Hevea rubber particles and is an average of the values in the reference cited. Rubber accounted for 91% of this dry weight.
¶¶The values represent the percent dry weight (w/w) of the rubber particles. Rubber accounted for 88% of this dry weight.

TABLE 2

Relative abundance of specific fatty acids in guayule rubber particles as analyzed by gas chromatography.

| | Relative Percent | |
|---|---|---|
| Lipid | Total lipids | Neutral lipids |
| 14:0 | 10.5 | 12.7 |
| 16:0 | 8.4 | 17.1 |
| 18:0 | 1.3 | 4.4 |
| 18:1 | 3.4 | 5.0 |
| 18:2 | 22.7 | 32.5 |
| 18:3 | 11.0 | 15.1 |

Comparisons show that the total polar lipid content in rubber particles and cucumber seed oil bodies is similar, 0.73% in guayule and 0.78% in Hevea versus 0.90% in cucumber seed oil bodies (Table 1, FIG. 13). However, the polar lipid composition is different. In cucumber seed oil bodies, PC is the major polar lipid, accounting for 95% of the total polar lipids (FIG. 13). This holds true for all oil bodies examined where PC accounts for 43–95% of the polar lipids (Table 1). In contrast, the most abundant polar lipid in rubber particles is PS and accounts for 40.6% and 71.5% of the polar lipids in guayule and Hevea particles, respectively (FIG. 13). Rubber particles possess other phospholipids including PE, PI and PA which account for 32.1%, 14.8% and 12.5%, respectively, of the polar lipids in guayule and 12.4%, 11.8% and 4.6%, respectively, in Hevea particles. In previous studies it was reported that Hevea particles contain 56.5% PC (Hasma and Subramaniam, J. Nat. Rubb. Res. 1:30–40, (1986); Ho et al., Proc. Int. Rubb. Conf. Kuala. Lumpur 4: 441–456, 1975; Hasma, J. Nat. Rubb. Res. 6:105–114 (1991)). However, our analyses show that PC exists as a faint spot that is only observed when lipid samples are overloaded on TLC plates.

Unlike deteriosomes or lipofuscin (Tappel, Lipid Peroxidation and Fluorescent Molecular Damage to Membranes, Academic Press, New York pp. 145–170, 1975; Eldred, Adv. Biosci 64:23–36 (1987)), neither rubber particle suspensions nor lipids extracted from rubber particles exhibit fluorescence spectra with excitation maxima in the 270–430 nm range and emission maxima between 430 and 620 nm. Likewise, TLC of rubber particle lipids do not show the yellow, yellow/green and orange-red fluorescent bands characteristic of certain forms of lipofuscin (Eldred, Adv. Biosci 64:23–36, (1987)).

Rubber particles treated with lipoxygenase following a 1 hr lipase incubation caused a large increase in oxygen consumption (FIG. 14), in contrast to rubber particles not incubated with lipase which showed no oxygen uptake. This indicates that unsaturated lipids, having a cis,cis-1,4 pentadiene system, are present in rubber particles and are available as substrates of lipoxygenase and subsequently, AOS. Because oxygen consumption is observed only after lipase treatment, it indicates that in rubber particles unsaturated lipids exist as glycerol esters rather than as free fatty acids (FFA).

In view of the similar physical and chemical characteristics of rubber particles and seed oil bodies, proteins from each were examined. Guayule and Hevea particles subjected to isoelectric focusing show an isoelectric point between pH 7.70–7.82. This differs from seed oil bodies which focus between pH 5.7–6.6 (Tzen et al., Plant Physiol. 101:267–276 (1993)) and implies that the protein constituents of rubber particles are seed oil bodies are dissimilar.

Phenol extraction permits large quantities of protein to be isolated from rubber particles and allowed us to make direct comparisons of proteins from guayule rubber and Brassica and soybean oil bodies (FIG. 15A). In guayule particles the most abundant protein is the RPP form of AOS which accounts for 40% of all protein in guayule rubber (Pan et al., Biol. Chem. 270:8487–8494 (1995)). Immunological analyses of duplicate gels probed with antibodies to Brassica or soybean oleosins do not show a positive reaction with any rubber proteins. This is true for Brassica (FIG. 15B) and soybean (FIG. 15C) specific oleosins. The guayule gel was overloaded to help visualize if any scarce, low molecular weight proteins were present. In addition, by over loading the gel, one would expect possible contaminants to the rubber preparation, such as oil bodies, to be identified by detecting oleosins. A test for the presence of lipoproteins using oil red O (Kruth, Lab Invest. 50:87–93, 1984; Pearse, Histochemistry: Theoretical and Applied, London, Churchill pp. 398–446 (1968); Ramirez-Zacarias et al., Histochemistry 97:493–497 1992) did not give a positive reaction for any of the rubber particle proteins from guayule.

8.3 DISCUSSION

At least six different classes of lipophilic structures have been identified according to their in planta location (Table 1). They include seed oil bodies, fruit oil bodies, vegetative oil bodies, chromoplast globules, deteriosomes and rubber particles. All have a spherical shape that ranges up to 1.0 $\mu$m in diameter or larger, all are bouyant in aqueous solutions and all can be easily isolated by flotation and centrifugation. Seed oil bodies are the most widely studied. Found in cotyledon or endosperm tissues, they serve as the main food storage reserve in oil seeds. Fruit oil bodies, found in the fleshy pericarp of mature fruit, do not provide food reserves for the growing plant but act as attractants for animals which disperse seeds within the fruit. Vegetative oil bodies are structures that occur in the leaves of some plants. Chromoplast globules, localized in the plastids of fruit, flowers or leaves, are sites of carotenogenic pigment accumulation (Esau, Anatomy of Seed Plants, John Wiley and Sons, New York, pp. 500 (1977); Sitte et al., Chromoplasts In Czygan FC (ed) Pigments in Plants, Gustav Fischer Verlag, New York pp. 117–148 (1980)). Deteriosomes, a recently described class of lipophilic structures, accumulate in tissues undergoing senescence and have been detected in both plant (Yao et al., Plant Physiol. 97: 502–508, 1991) and animal tissues (Yao et al., J. Cell Biochem 51: 488–494, 1993). They are believed to be byproducts of membrane deterioration and may be similar to lipofuscin in animals. Rubber particles, found in laticifer cells of Hevea and in parenchyma cells of guayule stems and roots (Backhaus, Israel J. Bot. 34: 283–293 (1985)), are sites of polyisoprene synthesis and accumulation.

9. EXAMPLE: ANALYSIS OF NEUTRAL LIPIDS

Neutral lipids are the primary constituent of plant lipophilic structures (Table 1). Seed, fruit, and vegetative oil bodies possess a neutral lipid core that is composed primarily of TAG with significantly smaller but measurable amounts of DAG, MAG and, in most cases, FFA. The exception is jojoba seed which accumulates WE in place of TAG (Gunstone, Endeavor 14: 40–43 (1990); Wisniak, Prog. Chem. Fats. Other Lipids 15: 167–218 (1977). The most abundant neutral lipids in chromoplast globules are carotenoids. Chromoplasts also contain relatively high proportions of glycolipids and measurable quantities of tocopherols and polar lipids (Kirk, The Plastids: Their chemistry, structure, growth and inheritance, Elsevier/North-Holland Biomedical Press, New York, pp. 960 (1978); Deruère et al., Plant Cell 6:119–133 (1994) and references cited therein). In rubber particles the most abundant neutral lipid is polyisoprene, which accounts for over 90% of the particle weight. The major non-rubber, neutral lipids are TAG and other lipids similar to those found in other lipophilic structures (Table 1). Of the free fatty acids identified by GC in guayule particles, the bulk are linoleic and linolenic acids. In earlier studies Hevea particles (Hasma and Subramaniam, J. Nat. Rubb. Res. 1:30–40, 1986; Ho et al., Proc Int Rubb. Conf. Kuala Lumpur 4:441–456 (1975); Hasma, J. Nat. Rubb. Res. 6: 105–114 (1991)) where shown to have a non-rubber, neutral lipid content that ranged from 0.40 to 3.21%, of which 28.5 to 63.3% was TAG, depending on clonal variation. Our results agree with this and show that MAG and DAG are also present in small amounts. It is noteworthy that, unlike Hevea, guayule particles do not contain any tocopherol.

10. EXAMPLE: ANALYSIS OF POLAR LIPIDS

Rubber particles possess quantities of polar lipids that approach 1% of the total particle weight. The polar lipid content of seed oil bodies also averages about 1%. In comparison, fruit oil bodies contain only 0.39% (avocado) to 0.60% (palm) polar lipids. The smallest quantity of polar lipids is observed in vegetative oil bodies from cabbage which contain only 0.16% by weight polar lipids. Oil bodies from both fruit and vegetative organs do not possess a unit membrane and this is reflected in their reduced polar lipid levels. Chromoplast globules from Viola contain 4.7% polar lipids of which 21.5% is phospholipid, equivalent to 1.0% of the weight of the globule. It is noteworthy that these structures also are bound by a membrane monolayer (Hansmann and Sitte, Plant Cell Rep 1: 111–114 (1982).

Using the calculations of Tzen and Huang, J. Cell. Biol. 117: 327–335 (1992) we were able to determine that the quantity of phospholipids present in guayule rubber is sufficient to form a monolayer, but not a bilayer, around each particle. The average diameter of rubber particles in our preparations is 1.32 $\mu$m. This value is calculated from the weight and number of particles in our samples and the known density of rubber which is 0.913 g cm$^{-3}$ (Table 3; Wood, Physical constants of different rubbers, In: Brandrup J. Immergut E H (eds) Polymer Handbook, John Wiley and Sons, New York p. vl (1975). These calculations are consistent with previous light scattering determinations which measured particle diameter directly (Cornish et al., J. Nat. Rubb. Res 8: 275–285 (1994)). The average volume of our particles is calculated to be 1.204 $\mu$m$^3$. If a monolayer is assumed to be 2.5 nm thick (Jones and Chapman, Micelles, Monolayers, and Biomembranes, Wiley-Liss, New York, pp. 24–64 (1995)), then the volume of a shell surrounding each particle is [4/3 $\pi$ (660 nm)$^3$ −4/3$\pi$ (660−2.5 nm)$^3$]=1.36×10$^7$ nm$^3$. The amount of phospholipid in each rubber particle is 0.78×10$^{-14}$ g (Table 3). The average density of phospholipid is 1.03 g cm$^{-3}$ and the volume occupied by the phospholipid shell is 0.78×10$^{14}$ g÷1.03 g cm$^{-3}$=0.76×10$^7$ nm$^3$. This is equal to 56% of the shell volume [0.76×10$^7$ nm$^3$÷1.36×10$^7$ nm$^3$]. The surface area of the average rubber particle is 5.47×10$^6$ nm$^2$ (4 $\pi$r$^2$). To occupy 56% of this area with 6.18×10$^6$ molecules of phospholipids, each phospholipid needs to occupy an area of 0.49 nm$^2$ or a square with a width of 0.704 nm. This is the same as the value of 0.49 nm$^2$ calculated for a phospholipid molecule in a monolayer surrounding seed oil bodies (Tzen and Huang, J. Cell. Biol. 117: 327–335 (1992)). The existence of a lipid monolayer surrounding rubber particles has also been inferred from electron-paramagnetic studies (Siler et al., Anal Biochem 229:278–281 FASEB J. 6:A1374, (1995). Unlike oil bodies, we do not know how rubber particle proteins associate with this monolayer. It is not known if they reside in the interior or are embedded in the membrane monolayer of the particle.

TABLE 3

Physical data for guayule rubber particles. The volume of each rubber particle is 1.173 × 10$^{-12}$ cm$^3$.

| | Total | Rubber | PL | Protein | NL |
|---|---|---|---|---|---|
| Weight (%, wt/wt) | 100 | 94.26 | 0.72 | 1 | 5.02 |
| Density(g/cm$^3$) | 0.9315 | 0.913$^a$ | 1.03$^b$ | 1.3 | 0.92$^c$ |
| Weight(×10$^{-14}$ g) | 109 | 102.74 | 0.78 | 1.09 | 5.47 |
| # Molecules (×10$^5$)$^d$ | | 10.17 | 61.8 | 1.22 | 374 |
| Ratio of Molecules | | 9 | 51 | 1 | 306 |

$^a$Wood (1975)
$^b$Merck Index (1976).
$^c$Density taken from Merck Index for triolein or trilinolien.
$^d$Number of moles calculated by (weight ÷ molecular weight) × (Avogadro's number)
NL = 880
PL = 759
Protein = 53,438 (M$_r$ of AOS, Pan et al. 1995)
Rubber = 6.08 × 10$^5$(Backhaus and Nakayama 1988)

The polar lipid composition of rubber particles is unusual in that PS is the most abundant constituent compared to seed oil bodies where PC is the most abundant phospholipid. The reasons for this are unclear, however, it may correlate with the known physical properties of rubber particles. Seed oil bodies are designed to maintain a spherical shape during long periods of dessication.

To do this they must not coalesce. Synthetic lipid vesicles that contain only PC are unable to fuse with a living plasma membrane or to other PC vesicles (Papahadjopoulos et al., Biochim. Biophys. Acta 448:245–264 (1976)). It is believed that the presence of high PC in combination with oleosins on the surface monolayer of the oil body helps prevent fusion (Tzen and Huang, J. Cell. Biol. 117: 327–335 (1992)). In contrast, rubber particles readily undergo fusion and this is observed following centrifugation at high speeds where rubber suspensions will fuse into an inseparable rubber pad. According to Devaux, Biochemistry 30: 1163–1173 (1991) and references cited therein, PS and PE are believed to promote fusion of membrane vesicles. Guayule rubber particles observed in situ appear to coalesce with one another and also interact with tonoplast membranes (Backhaus & Walsh, Gray Bot. Gaz. 144: 391–400 (1983).

11. EXAMPLE

ANALYSIS OF PROTEINS

Previous studies indicated that guayule rubber particles contain relatively few proteins compared to Hevea (Cornish et al., J. Nat. Rubb. Res. 8: 275–285 (1994); Siler and Cornish, Anal Biochem 229:278–281 FASEB J. 6:A1374 (1995). Rubber particles were tested for the presence of oleosins. Oleosins are abundant, 15–26 kD hydrophobic proteins specific to seed oil bodies (Murphy et al., Biochim. Biophys Acta 1088: 86–94 (1991); Tzen and Huang, J. Cell. Biol. 117: 327–335 (1992)), that prevent oil bodies from coalescing in dedicated seeds (Murphy et al., Biochim. Biophys. Acta 1088: 86–94 (1991)). Previous work suggested that oleosins were not present in dilute guayule rubber particles (Lee et al., HortScience 30: 197–205

(1994)). In highly enriched protein extracts from guayule rubber (FIG. 15A), no evidence of cross-reactivity to antibodies for Brassica or soybean oleosins was observed. Our findings support the earlier findings of Lee et al., Planta 193: 461–469 (1994).

12. EXAMPLE

AOS AND OXIDATION IN RUBBER PARTICLES

12.1 MATERIALS AND METHODS

12.1.1 WASHED RUBBER PARTICLE ISOLATION

Rubber particles were isolated according to Cornish and Backhaus, Phytochemistry 29: 3809–3813 (1990) using a 50 mM potassium phosphate wash buffer, pH 8.0 in place of Tris-HCI.

12.1.2 FLUORESCENCE SPECTROSCOPY

Rubber particle suspensions containing approximately $5 \times 10^{10}$ particles $ml^{-1}$ or 100 $\mu g$ $\mu l^{-1}$ rubber were extracted for lipids and analyzed according to Yao et al., J Cell Biochem 51: 488–494 (1993); Eldred, Anal. Biochem. 64: 23–36 (1987), Malshet et al., Lipids 9: 328–332 (1974) and above (see sec. 8.1) using a FluoroMax spectrofluoromoeter (JY/SPEX Instruments SA, Inc.) with an excitation maxima of 300 nm and an emission maxima of 405 nm. Background fluorescence was automatically subtracted. To test the effectiveness of different inhibitors, particles were incubated in the absence or presence of salicylic acid (SA), acetylsalicylic acid (ASA, aspirin), salicin, n-propylgallate or 5-sulfosalicyclic acid at a final concentration of 1 mM before lipid extraction and fluorescence spectroscopy was performed. The effect of pH on relative fluorescence spectroscopy was performed. The effect of pH on relative fluorescence intensities was also determined on lipids extracted from rubber particle lipids according to Malshet et al., Lipids 9: 328–332 (1974).

12.1.3 TIME COURSE ANALYSIS

A 24-hour time course analysis of lipid peroxidation was made on rubber particles and extracted lipids according to Bidlack and Tappel, Lipids 8: 177–182 (1973). A suspension of rubber particles containing 12.15 mg rubber at a concentration of 100 $\mu g$ $\mu l^{-1}$ was mixed with 1 ml 50 mM phosphate buffer, pH 8.0 and incubated in the presence or absence of 1 mM ASA, 1% BHT or 1% α-tocopherol. Rubber particles and their extracted lipids were then analyzed via fluorescence spectroscopy. Extracted lipids were also analyzed by thin layer chromatography according to Braddock and Dugan, J. Am. Oil. Chem. Soc. 50: 343–347 (1973) following a 1 hour incubation of rubber particles in 1 mM SA. A thiobarbituaric acid assay (Buege and Aust, Microsomal lipid peroxidation, In: Fleischer S, Packer L (eds) Methods in Enzymology, Academic Press, New York, 52: 302–310 (1978)) was also used to monitor the presence of malondialdehyde (MDA) in lipids extracted from rubber particle suspensions (12.5 mg at a concentration of 100 $\mu g$ $\mu l^{-1}$) incubated for 30 min in 10 mM SA, ASA, salicin, n-propylgallate, or 5-sulfosalicylic acid.

12.1.4 SUPEROXIDE/COLORIMETRY ASSAY

The superoxide dismustase (SOD) acrylamide gel assay (Beauchamp and Fridovich, Anal. Biochem. 44: 276–287, 1971) was modified into a colorimetric assay to monitor lipid oxidation in rubber particles. A 1–5 $\mu l$ suspension of fatty acids or rubber particles (at 100 $\mu g$ $\mu l^{-1}$) was added directly to 200 $\mu l$ 50 mM potassium phosphate buffer, pH 8.0 containing 2.8 $\mu M$ riboflavin and 28 mM tetramethyllethylenediamine (TEMED). Alternatively, particles were preincubated in 1 mM SA, ASA, salicin, n-propylgallate or 5-sulfosalicyclic acid for 10 min or bubbled for 5 min with a mixture of CO and $O_2$ gas. Superoxide was generated by exposing the combined particles and riboflavin/TEMED solution to light, provided by a 100 W bulb, spaced 30 cm from the suspension, for 10 minutes. The degree of reduction was then determined by adding 200 $\mu l$ 50 mM potassium phosphate buffer, pH 8.0 containing 2.45 mM nitroblue tetrazolium (NBT) and monitoring for 10 min. Reduction of NBT caused a yellow to blue color change. The effect of CO on AOS inhibition and its reversal by exposure to high light was tested by placing the CO and $O_2$ treated suspension directly in front of a water-cooled, slide projector lamp and exposing the mixture to bright light for 1, 5 or 10 min before performing the NBT assay. To ensure that rubber particles did not contain any endogenous SOD they were analyzed for SOD using the acrylamide gel assay (Beauchamp and Fridovich. Anal. Biochem. 44: 276–287 (1971)).

12.1.5 UV SPECTROPHOTEMETRY TO MONITOR CONJUGATED DIENES

The formation of fatty acid hydroperoxides can also be measured by following the increase in UV absorption at $A_{234}$ due to the formation of conjugated dienes (Buege and Aust "Microsomal lipid peroxidation", Fleischer S. Packer L. (eds), Methods in Enzymology, Academic Press, New York 52: 302–310 (1978). Using this we were able to follow lipid peroxidation in free fatty acids, rubber particles or extracted particle lipids. Relative quantification of conjugated dienes was performed by incubating rubber particles for 20 min in the absence or presence of 1 mM ASA or salicin followed by a 30 min incubation with or without 0.05% $H_2O_2$. Lipids from these particles were extracted and analyzed spectrophotometrically at 234 nm according to Aust, Lipid peroxidation, In: Greenwald R (ed) CRC Handbook of Methods for Oxygen Radical Research, CRC Press, Boca Raton, pp. 203–207 (1985).

Likewise, the effect of superoxide, produced by the riboflavin/TEMED mixture and light, on lipid peroxidation was determined. Superoxide was introduced into a 5.0 $\mu l$ sample of 10 mM linoleic acid by adding 300 $\mu l$ 50 mM potassium phosphate buffer, pH 8.0 containing 2.8 $\mu M$ riboflavin and 28 mM TEMED. The mixture was exposed to light and scanned in a UV spectrophotometer at 200 to 300 nm at 10 sec intervals for 2 minutes and again at 5 and 10 min. The effect of AOS on superoxide-induced linoleic hydroperoxides was determined using partially pure AOS solubilized from fresh rubber particles using the CHAPS extraction and filtration procedure (Pan et al., J Biol Chem 270: 8487–8494, 1995), which removed all remaining rubber. One $\mu g$ partially pure AOS was added to oxidized linoleic acid and UV scanned at 2 minute intervals.

To test if AOS could block lipid peroxidation, 1 $\mu g$ partially pure AOS, preincubated in the presence or absence of 1 mM ASA or salicin, was added to linoleic acid. This mixture was scanned at $A_{234}$ followed by addition of riboflavin/TEMED and exposure to 10 min. of light, to produce superoxide. The mixture was rescanned at 10 min intervals.

12.2 RESULTS

Guayule rubber particles bear a structural and chemical similarity to lipofuscin particles found in mammalian tissues. Lipofuscin particles, commonly referred to as age pigments, are dark, spherical bodies, 1–20 μm diam that appear in the cytoplasm of aged cells. Like rubber particles they contain neutral lipids, polyisoprenes, dolichol and dolichol esters, phospholipids and proteins (Pullarkat and Reha, J. Biol. Chem. 257: 5991–5993 (1982); Hemming, Biosynthesis of dolichols and related compounds, In: Porter J W, Spurgeon S L (eds) Biosynthesis of isoprenoid compounds, vol. 2, John Wiley & Sons, New York, pp. 306–354 (1983); Kin et al., J. Neurochem. 40: 1465–1473 (1983). Lipofuscin exhibits a characteristic fluorescence due to the accumulation of lipid peroxidation byproducts (Eldred, Anal. Biochem 64: 23–36 1987; Tappel, Fed Proc Fed Amer Soc Exp Biol 24: 73–79, 1965). Initially, it was expected that rubber particles would exhibit a similar fluorescence pattern. However, this was not the case, as native rubber particles did not fluoresce (FIG. 16). This was surprising because polyisoprenes are very susceptible to autoxidation and lipid peroxide accumulation and guayule particles contain no known chemical antioxidants (ie tocopherols) which could suppress the formation of such compounds. We therefore proposed that this lack of fluorescence was due, in part, to the presence of AOS. As AOS is known to rapidly dehydrate lipid peroxides into epoxides and is also the most abundant protein in guayule rubber, it suggested that this enzyme may have a role in protecting the rubber particles from autoxidation by suppressing the propagation step initiated by lipid hydroperoxides. To test this we used a series of inhibitors, i.e., salicylates and CO which are known to block AOS activity.

Incubating native rubber particles in 1 mM ASA caused a striking increase in fluorescence (FIG. 16) with an excitation maxima ranging form 300–305 nm and emission maxima ranging from 400–411 nm. This fluorescense increased with increasing incubation time (FIG. 16a). Likewise, lipids extracted from these particles showed a nearly identical fluorescence pattern, having an emission and excitation range of 299–313 and 400–414 nm (FIG. 16b). Lipids from particles not treated with ASA showed only a fluorescence (FIG. 16b) due to oxidation which occurs during lipid extraction. Identical fluorescence patterns were obtained for particles treated with 1 mM SA. Particles incubated with 1 mM salicin, 5-sulfosalicylic acid or n-propylgallate, did not fluoresce, indicating that these inhibitors probably do not inhibit AOS. Again, lipids extracted from these same particles gave the similar fluorescent patterns as the intact particles.

The formation of fluorescent pigments in rubber particles and extracted lipids was followed over a 24 hr period. In the presence of ASA fluorescence increased up to 12 hours and then plateaued (FIG. 17), creating a sigmoidal curve. In the absence of ASA, where endogenous AOS activity is high, there was no increase in fluorescence. In particles where AOS was inhibited but antioxidants were present (i.e. BHT or α-tocopherol) there was a slight increase in fluorescence (FIG. 17). Extracted lipid from rubber particles analyzed by TLC according to Bidlack and Tappel Lipids 8: 177–182 (1973) did not show any visually apparent quantitative changes in their amino phospholipid profiles between control and inhibitor-treated particles.

To test whether MDA was responsible for the fluorescence pattern, sodium methoxide was used to create an alkaline environment (pH 11.5). No change in fluorescence intensity was observed with a change in pH, suggesting that MDA Schiff base adducts were not present.

The colormetric assay for SOD involves superoxide generation by photoactivation of riboflavin. In the absence of SOD, NBT is reduced to blue formazan by superoxide (Beauchamp and Fridovich, Anal. Biochem. 44: 276–287 (1971)). If SOD is present, NBT remains yellow. We utilized this system to determine if superoxide could be used as an oxidant on rubber particles. If AOS were active, rubber particles would be protected from peroxidation and NBT would be reduced by superoxide resulting in a blue color. However, if AOS were inactivated, then rubber particles would act as a sink for superoxide and NBT would not be reduced to blue tetrasodium, or would be reduced at a slower rate. For this assay to work, endogenous SOD must not be present in rubber particles. This was verified by the acrylamide gel assay of native proteins from rubber particles.

Incubating rubber particles in either ASA or SA led to particle lipid peroxidation by superoxide as indicated by the yellow color or NBT (Table 4). Incubation in 5-sulfosalicylic acid, n-propylgallate and salicin did not appear to inhibit AOS, as indicated by the blue color development of NBT (Table 4). This was consistent with results monitored by fluorescence spectrophotometry. When AOS was inhibited with CO, a known inhibitor or cytochrome P450s, NBT remained yellow as would be expected for an inhibitor. Moreover, when CO inhibition was reversed by strong light, there was a partial reduction of NBT as indicated by grayish yellow color development. Exposure of high light to CO-bound-AOS in rubber particles for 1 min resulted in partial restoration of AOS (Table 4). A 5 min high light exposure resulted in maximum restoration of AOS activity. More than 5 min high light resulted in a reduction in AOS activity, as NBT was not reduced.

TABLE 4

Colorimetric assay utilized to determine the effect of superoxide on rubber particles, with or without inhibition of AOS. Yellow color indicates that NBT was not reduced, while blue indicates full reduction by superoxide. Grey and yellow/grey indicate respectively lesser degrees of reduction.

| TREATMENT | | | | | COLOR CHANGE | | | |
|---|---|---|---|---|---|---|---|---|
| riboflavin/ TEMED | Linoleic Acid | Rubber Particles | Inhibitor[a,b] | NBT | Yellow | Blue | Grey | Yellow Grey |
| X | | X | | | X | | | |
| | | X | | X | X | | | |
| X | | | | X | | X | | |
| X | X | | | | X | | | |
| X | X | | | X | | | X | |
| X | X | X[c] | | X | X | | | |

TABLE 4-continued

Colorimetric assay utilized to determine the effect of superoxide on rubber particles, with or without inhibition of AOS. Yellow color indicates that NBT was not reduced, while blue indicates full reduction by superoxide. Grey and yellow/grey indicate respectively lesser degrees of reduction.

| TREATMENT | | | | | COLOR CHANGE | | | |
|---|---|---|---|---|---|---|---|---|
| riboflavin/ TEMED | Linoleic Acid | Rubber Particles | Inhibitor[a,b] | NBT | Yellow | Blue | Grey | Yellow Grey |
| X | X | X[c] | ASA | X | | | | X |
| X | | X | | X | | X | | |
| X | | | ASA | X | | X | | |
| X | | X | ASA | X | X | | | |
| X | | | SA | X | | X | | |
| X | | X | SA | X | X | | | |
| X | | | SAL | X | | X | | |
| X | | X | SAL | X | | X | | |
| X | | | 5SSA | X | | X | | |
| X | | X | 5SSA | X | X | | | |
| X | | | nPG | X | | X | | |
| X | | X | nPG | X | | X | | |
| X | | | CO[ddd] | X | | X | | |
| X | | X | CO[eee] | X | X | | | |
| X | | X | CO/LT[f] | X | | | X | |
| X | | X | CO/LT[g] | X | | | | X |
| X | | X | CO/LT[h] | X | X | | | |

[a]. Rubber particles were incubated with the inhibitor for 10 min prior to assay.
[b]. Abbreviations of inhibitions: ASA acetylsalicylic add; SA salicylic acid; SAL salicin; 5SSA S-sulfosalicylic acid; nPG n-propyl gallate; CO carbon monoxide
[c]. CHAPs extracted rubber particle protein was used rather than whole particles.
[d]. A mixture of CO and $O_2$ were bubbled into riboflavin/TEMED solution for 5 min before assay.
[e]. A mixture of CO and $O_2$ were bubbled into rubber particle suspension for 5 min prior to assay.
[f]. After bubbling the rubber particle suspension was placed in the path of a slide projector light (as described in Materials and Methods) for 1 min.
[g]. 5 min light exposure.
[h]. 10 min light exposure.

To confirm that AOS affected lipid peroxidation, we used superoxide to generate linoleic hydroperoxides which was measured directly by conjugated diene formation. Autoxidized linoleate yields color absorptivity at $A_{234}$ due to the diene conjugation. Linoleic acid incubated with riboflavin/ TEMED in light forms the expected conjugated dienes (FIG. 18a). When AOS was added, A234 decreased, indicating the conversion of the conjugated diene to the epoxide and ketols. Incubating linoleic acid and riboflavin/TEMED with AOS, and exposing the mixture to light, prevented the increase in $A_{234}$. However, if AOS was first incubated with ASA before adding it to linoleic acid and riboflavin/TEMED there was a notable increase in $A_{234}$ (FIG. 18b) indicating that active AOS protected linoleic acid form autoxidation by superoxide.

12.2.1 CURATIVE EFFECTS OF AOS ON CELL DAMAGE

The curative effects of AOS, acting as an antioxidant, on cell damage are shown in FIG. 18A and supported by FIGS. 11 and 12. AOS was added to oxidized linoleic acid to show a time-dependent disappearance of conjugated dienes.

The analysis of membrane lipid peroxidation showing the role of allene oxide synthase is illustrated in FIG. 11. Peroxidation is initiated by oxidizing radical (FIG. 11(a)), followed by oxidation to form peroxyl radical (FIG. 11(b)). The peroxyl radical partitions to the water-membrane interface (FIG. 11(c)) and lipid peroxide/lipid hydroperoxide is poised in the membrane-water interface for repair by allene oxide synthase (FIG. 11(d)). Conversion of lipid hydroperoxide to lipid epoxide is caused by allene oxide synthase (FIG. 11(e)). Thereafter, spontaneous decomposition of the epoxide to ketol results (FIG. 11(f)) allowing for the possible reorientation of ketol in the membrane-water interface (FIG. 11(g)). A similar analysis is provided in FIG. 12 of lipid peroxidation and repair of triglycerides.

The formation of conjugated dienes was also examined by incubating particles in $H_2O_2$, in the presence or absence of ASA or SA and examining extracted lipids at $A_{234}$ (FIG. 19). Conjugated dienes formed only when AOS was inhibited by ASA in the presence of $H_2O_2$ (FIG. 19).

12.3 DISCUSSION

Fluorescence is an excellent indicator of lipid oxidation (Gray, J. Am. Oil. Chem. Soc. 55: 539–542, 1978; Logani and Davis, Lipids 15: 485–490 (1980); Dillard and Tappel, Lipids 6: 715–721 (1971); Tsuchida et al., Chem Phys Lipids 44: 297–325 (1987) and gives a direct correlation in biological systems (Chio et al., Science 166: 1535–1536 (1969); Dillard and Tappel, Lipids 6: 715–721 (1971). Fluorescence is also a property of lipofuscin in animals (Hampere, Virchows Arch. Pathol. Anat. 242:1–24 (1934); Eldred, Anal Biochem 64: 23–36 (1987); Tappel, Lipid Peroxidation and fluorescent molecular damage to membranes, Academic Press, New York, pp. 145–170 (1975) and deteriosomes in plants (Yao et al. op. cit. 1991, 1993) which are viewed as holding chambers for phospholipid degradation products. Using fluorescence spectroscopy as an initial screen, we determined that native rubber particles were perturbed by the addition of AOS inhibitors, in which case lipid peroxidation products were rapidly formed. This is consistent with the role of AOS as an antioxidant.

Rubber particles and extracted lipids emit a fluorescence spectra with excitation maxima ranging from 299–313 nm and emission maxima between 400–414 nm if AOS is inactivated. This spectra differs slightly from lipofuscin, which has a generally accepted excitation range of 270–430 nm or 330–360 nm and an emission range of 560–620 or 420–480 nm, depending on the lipofuscin source, products involved and instrument calibration (Eldred, Anal Biochem 64: 23–36 (1987); Tappel, Lipid Peroxidation and fluorescent molecular damage to membranes, Academic Press, New York, pp. 145–170 (1975). The variation can be due to numerous natural secondary products of lipid peroxidation. MDA has been linked to fluorescence in lipofuscin (Chio and Tappel, Science 166: 1535–1536 (1969) because it reacts with polypeptides and exhibits an excitation range of 390–400 nm and an emission range of 460–470 nm (Kikugawa and Sawamura, J. Am. Oil. Chem. Soc. 64:1156–1162, 1987). However, different compounds have been linked to fluorophores in aging tissue (Kikugawa et al., Chem. Pharm. Bull. 37: 3061–3065, 1989; Yoden et al., The formation of fluorescent substances by lipid peroxides, Yakugaku Zassho 102: 768 (1982); Tsuchida et al., Chem Phys Lipids 44: 297–325 (1987); Tashiro et al., Agric. Biol. Chem. 49: 1739–1747 (1985)). Compounds which might have fluorescence patterns which coincide with rubber particle fluorescence include lipid peroxyl and alkoxyl radicals that interact with tyrosine residues on proteins and which have a 295–320 nm excitation range and a 388–410 nm emission range (Kikugawa et al., Lipids 26: 922–929 (1991)). Linoleic acid hydroperoxidces that interact with tyrosines have excitation and emission maximi at 330 and 420 nm, respectively (Shimasaki et al., Lipids 17: 878–883 (1982)). Lipid hydroperoxides and secondary products can also react with cellular DNA to produce excitation and emission monos of 315 and 420 nm, respectively (Fugimoto et al., Biochim Biophys Acta 795: 100–107, 1984). The aldehydes, 1-heptanal, 2,4-decadienal and glutaraldehyde also yield 320–370 nm excitation spectra and 410–450 nm emission spectra when they interact with membrane proteins from human erythrocyte ghosts. These proteins also give the identical spectra upon interacting with 13-hydroperoxylinoelic acid (Beppu et al., Chem. Pharm. Bull. 34: 781–788 (1986)). It is noteworthy that the fluorescence spectra produced by the above compounds are inhibited in the presence of antioxidants.

By comparing these spectra we speculate that MDA is not responsible for the similarity of observed fluorescence to those of rubber particles (FIG. 16). Moreover, the fluorescence intensity of rubber particles does not change with pH, as does the fluorescence intensity of MDA (Malshet, Lipids 9: 328–332 (1974)). Additionally, MDA is formed from fatty acids with three or more double bonds (Esterbauer and Zollner, Free Radic. Biol. Med. 7: 197–203 (1989); Pryor et al., Lipids 11: 370–379 (1976) and cannot be formed from linoleic acid, the predominant PUFA in rubber particles (see sec. 8.1).

Results from the time course studies of peroxidation in the presence of ASA are consistent with the results of Shimasaki et al., J. Am. Oil. Chem. Soc. 54: 119–123 (1977) and Bidlack and Tappel, Lipids 8: 177–182 (1973) where fluorescence production increased up to 9–12 hours, then remained level up to 24 hours. The sigmoid nature of the curve indicates that lipid hydroperoxides form slowly when acting as initiators of chain reactions (O'Brien and Rahimutula, J. Agric. Food Chem. 23: 154–158 (1975)). An initial curve formed after 0–20 min is characteristic of hydroperoxide formation with secondary product accumulation beginning after 10 min (Bidlack and Tappel, Lipids 8: 177–182 (1973)).

AOS functions by eliminating the hydroperoxide on lipids. Normally, the hydroperoxide serves as the main source of radicals, which then propagate the peroxidation of nearby lipids. These lipid alkoxyl radicals are cleaved into aldehydes via beta cleavage (Esterbauer and Zollner, Free Radic. Biol. Med. 7: 197–203 (1989)). Such aldehydes are highly reactive and are believed responsible for fluorescent production in oxidized lipids (Chio and Tappel, Science 166: 1535–1536 (1969); Kikugawa et al., Chem Pharm Bull 37: 3061–3065 (1989)). AOS halts the propagation step and thus limits damage by preventing the accumulation of secondary peroxidation products. When AOS is inhibited, the propagation of radicals continues unchecked causing a build-up of secondary products. These secondary products and their cellular reactants are believed to be the source of fluorescence.

Confirmation of the effects of AOS on lipid hydroperoxides of linoleate and guayule rubber lipids was provided by photosensitized oxidation and subsequent dehydration by AOS as monitored by UV spectroscopy at $A_{234}$ and the riboflavin/TEMED/NBT colorimetric assay. AOS functioned in two ways. It prevented the peroxidation of lipids in the presence of free radicals (FIGS. 18b and 19) and it converted conjugated dienes of linoleic hydroperoxide into epoxides (FIG. 18a). Chan, J. Am. Oil Chem. Soc. 54: 100–104 (1977) demonstrated that the photooxidation by riboflavin yields products identical to autoxidation. Anderson, Biochem. Biophys. Acta. 722: 158–162 (1983) established that formation of superoxides via oxidation of fully reduced flavins occurs at pH 7 and above. Taken together our data lend validity to the use of riboflavin/TEMED to generate lipid peroxides to elucidate the antioxidant properties of AOS in rubber.

One role of AOS might be linked to its potential role in regulating jasmonic acid (JA) synthesis. JA has been implicated in the induction of storage and defense proteins (Staswick, Plant Physiol 99: 804–807 (1992); Reymond et al., Proc. Natl. Acad. Sci., USA 92: 4145–4149 (1995), senescence and growth (Leshem, Free Radicals Biol. Med. 5: 39–49 (1988)) and ethylene stimulation (Gardner, HortScience 30: 197–205 (1995)). These effects translate to possible regulatory functions for AOS, as AOS is known to initiate the inaugural step in JA synthesis (Harms et al., Plant Cell 7: 1645–1654, 1995)). As such, AOS and rubber particles may be involved in lipid-mediated signal transduction. Salgo et al., Biochem. Biophys. Acta. 1127: 131–140 (1992) found that autoxidation can convert either free or esterified PUFAs into endoperoxides of prostaglandins. This suggests that autoxidation of PUFAs in vivo, particularly in membrane lipids, may be responsible for signal transduction-type responses. A correlation has also been established between mechanical stimulation, reduction in the amounts of lipids which serve as JA precursors and the induction of JA responses (Creelman and Mullet, Proc. Natl. Acad. Sci., USA 92: 4114–4119 (1995).

In natural rubber, a high molecular weight polyisoprene, a mere 1% $O_2$ causes chain scission resulting in a change of physical properties of rubber (Brydson, Rubber Chemistry, Applied Science Publishers Ltd, Essex, pp. 260–294 (1978). Highly reactive products formed during rubber oxidation include $CO_2$ formic acid, formaldehyde, acetic acid, laevulinic acid and laevulinaldehyde (Bevilacqua, J. Am. Chem. Soc. 77: 5396–5399, 1955, J. Am. Chem. Soc. 79: 2915–2918 (1957); Barnard et al., Rubber Chem. Tech. 45: 381–401 (1972)). The function of AOS as an antioxidant may be to prevent the formation of these toxic products, to permit long-chain rubber formation, and/or to preserve rubber's natural properties.

Calculations by Buettner, Arch. Biochem. Biophys. 300: 535–543 (1993) indicate that one tocopherol is able to protect ≈1000 lipid molecules. Physiologically this seems to correspond to the experimentally observed levels of tocopherol, ie 0.1% of total lipids, found in membranes. In Hevea rubber particles tocotrienols (α-, γ-δ-tocotrienols and α-tocopherol) account for 0.9% of latex lipids, (Dunphy et al., Nature 207: 521–522, 1965). Guayule rubber is devoid of tocopherols and does not have any other apparent natural antioxidant. However, AOS represents approximately 0.4% of the total rubber particle weight and can serve as an enzymatic antioxidant. While this is half the amount of antioxidant found in Hevea, AOS could be far more effective antioxidant as it is capable of repairing oxidation sites more rapidly than tocopherol. AOS has a $k_{cat}$ in excess of 1000 s$^{-1}$ and may act as a preventative antioxidant and as a chain-breaking antioxidant by blocking the propagation of radical chain reactions (Hamberg, Biochem Biophys Acta 920: 76–84, 1987).

13. EXAMPLE

LIPID PEROXIDATION AND RUBBER BIOSYNTHESIS

Rubber biosynthesis was monitored in particles treated with salicylic acid (SA) or acetylsalicylic acid (ASA, aspirin). These compounds are known to specifically inhibit AOS in other plants (Pena-Cortes, Planta 191: 123–128 (1993) and block the endogenous activity of AOS in rubber particles. Particles were also subjected to oxidative stress with superoxide to induce lipid peroxide formation, in which case rubber transferase (RuT) activity was suppressed.

13.1 MATERIALS AND METHODS

13.1.1 RUBBER PARTICLE ISOLATION

Rubber particles were isolated the morning of the experiment from guayule line 11591. All experiments were performed between December and February, when RuT activity is greatest. Particles were isolated according to Cornish and Backhaus, Phytochemistry 29: 3809–3813 (1990) with the following modifications. Bark tissue was homogenized in 50 mM potassium phosphate buffer, pH 8.0, containing 25 mM KF, 2.5 mM $MgCl_2$, and 5 mM dithiothreitol (DTT). Wash buffer contained 50 mM potassium phosphate buffer, pH 8.0, 2.5 mM $MgCl_2$ and 5 mM DTT.

13.1.2 RUBBER TRANSFERASE ASSAY IN WASHED RUBBER PARTICLES

RuT assays were performed according to Cornish and Backhaus, Phytochemistry 29: 3809–3813 (1990) using a final reaction volume of 500 μl containing, at final concentration, 3.5 mM $MgCl_2$, 2.5 mM $MnCl_2$ 26.7 μM FPP, 85 μM IPP and 1.48 μCi[$^{14}$C]-IPP (sp. act. 57 mCi mM$^{-1}$ NEN DuPont) in 50 mM potassium phosphate buffer, pH 8.0. The reaction was initiated by the addition of 200 μl of fresh, triple-washed rubber particle suspensions containing 10–20 mg rubber. Control reactions were made to test IPP incorporation into rubber by omitting FPP or adding 50 mM EDTA to the reaction (Cornish and Backhaus, Phytochem. 29: 3809–3813 (1990)). To control AOS activity, one or more of the following was added to the reaction mix (final concentration): 0.5 to 2 mM SA, 0.5 to 2 mM ASA, 11.2 μM riboflavin plus 11.2 mM TEMED, 0.003% $H_2O_2$, 2.0 U type II porcine pancreatic lipase (Sigma #L-3126) or 9450 U type V soybean lipoxygenase (Sigma #L-6632). These additions were made directly to the washed rubber particles and incubated for 20 min before adding to them to the reaction mix. In reactions that required dark conditions (to prevent the formation of superoxide), assay tubes were foil wrapped. Superoxide was generated by exposing suspensions containing riboflavin/TEMED to light provided by a 100 W bulb spaced 30 cm from the suspensions for 20 min according to Beauchamp and Fridovich, Anal. Biochem. 44: 276–287 (1971) as modified by in section 5.4 above. $H_2O_2$ was added directly to the particles and incubated for at least 20 min before adding SA or ASA. All RuT assays were run at 15° C. for 16 hours and activity was determined according to Cornish and Backhaus, Phytochemistry 29: 3809–3813 (1990) using liquid scintillation spectroscopy with toluene-based scintillant.

13.2 RESULTS

RuT activity was measured as the amount of [$^{14}$C]-IPP incorporated into washed rubber particles (source of RuT) in the presence of an allylic initiator (FPP) and $Mg^{2+}$ ion (Cornish and Backhaus, Phytochemistry 29: 3809–3813 (1990)). Passive incorporation, determined from controls containing EDTA which titrates divalent cations, is used to compare active incorporation by RuT in the rubber preparations. Active incorporation varies during the season, being greatest during the winter months of December to March. Omitting FPP tests for the efficiency of prenyltransferase activity initiated from new chains. To test the effect of salicylate mediated inhibition, it was crucial to use particles with high endogenous RuT activity. Experiments showed that RuT activity in the particles was high (Table 5). Passive incorporation (EDTA control) was less than 2% and control reactions without FPP were approximately 16% of reactions containing FPP. To test the effect of lipid peroxidation as regulated by AOS, salicylates were used to inhibit AOS and superoxide was added to the in vitro RuT assay. Addition of 1 mM SA alone led to a small drop (10–30%) in RuT activity (Table 5). Likewise, superoxide alone (riboflavin/TEMED plus light) led to a partial drop (5–35%) in RuT activity (Table 5), whereas non-photoreduced riboflavin/TEMED (no superoxide) did not reduce (5–15%) RuT activity appreciably (Table 5). When salicylates (SA or ASA) were added to rubber particles treated with superoxide (riboflavin/TEMED plus light), RuT activity was inhibited 88% (Table 6) compared to non-photoreduced riboflavin/TEDMED (no superoxide) with salicylates (SA or ASA) which was inhibited only 20% compared to controls. When $H_2O_2$ was used in place of superoxide (riboflavin/TEMED plus light) in combination with salicylates (SA or ASA) it caused an 89% inhibition of RuT activity.

TABLE 5

Activity of RuT in control reactions as measured by incorporation of [$^{14}$C]-IPP.

| Treatment | Experiment | nmol IPP mg$^{-1}$ dry rubber 16 hr$^{-1}$ |
| --- | --- | --- |
| + Control | 1 | 599.5 ± 43.5 |
|  | 2 | 361.3 ± 8.4 |
|  | 3 | 426.1 ± 55.3 |
| + EDTA; | 1 | 6.2 ± 2.3 |
| − control | 2 | 4.04 ± 0.01 |
|  | 3 | 7.25 ± 3.9 |
| − FDP; | 1 | 74.4 ± 2.15 |

TABLE 5-continued

Activity of RuT in control reactions as measured by incorporation of [$^{14}$C]-IPP.

| Treatment | Experiment | nmol IPP mg$^{-1}$ dry rubber 16 hr$^{-1}$ |
| --- | --- | --- |
| – control | 2 | 20.1 ± 0.75 |
|  | 3 | 16.2 ± 3.4 |
| Riboflavin/ | 2 | 336.0 ± 6.5 |
| TEMED and | 3 | 255.6 ± 12.8 |
| light |  |  |
| (superoxide) |  |  |
| Riboflavin/ | 2 | 314.9 ± 9.9 |
| TEMED and | 3 | 349.2 ± 16.0 |
| dark (no |  |  |
| superoxide) |  |  |
| 1 mM SA | 1 | 402.5 ± 18.2 |
|  | 2 | 320.4 ± 4.5 |
|  | 3 | 315.9 ± 10.6 |

TABLE 6

The effect of AOS and superoxide on RuT activity, as measured by [$^{14}$C]-IPP incorporation. All treatments were replicated within the experiment. All treatments were performed in the same experiment. Inset graphically demonstrates the percent [$^{14}$C]-IPP incorporation for the various treatments outlined in the table.

| Treatment | nmol IPP mg$^{-1}$ dry rubber 16 hr$^{-1}$ |
| --- | --- |
| + control | 599.5 ± 43.5 |
| + EDTA (– control) | 6.27 ± 2.3 |
| – FDP (– control) | 74.4 ± 2.15 |
| SA + light (superoxide) |  |
| 1 mM SA | 74.2 ± 1.29 |
| 0.5 mM SA | 50.2 ± 11.1 |
| SA + dark (no superoxide) |  |
| 1 mM SA | 513.0 ± 48.1 |
| 0.5 mM SA | 500.5 ± 29.9 |
| ASA + light (superoxide) |  |
| 1 mM SA | 98.3 ± 1.56 |
| 0.5 mM SA | 55.6 ± 2.25 |
| ASA + dark (superoxide) |  |
| 1 mM ASA | 421.6 ± 105.4 |
| 0.5 mM ASA | 599.3 ± 11.8 |

Lipase alone or in combination with lipoxygenase caused the rubber suspension to coagulate. Lipoxygenase alone did not have this effect. Because of the rubber coagulation it was impossible to determine the effect on RuT activity, although particles treated with lipoxygenase alone had activity similar to positive controls.

When SA levels exceeded 1.5 mM there appeared to be a negative effect on RuT activity, regardless of the presence of an superoxide (Table 7). The amount of [$^{14}$C]-IPP incorporation was not affected by superoxide (riboflavin/TEMED plus light) when SA was greater than 1.5 mM. A 2 mM SA RuT activity was severely inhibited in both photo reduced and non-photo reduced riboflavin/TEMED treatments.

TABLE 7

Effect of salicylic acid concentration on RuT activity in the presence or absence of superoxide.

| | nmol IPP mg$^{-1}$ dry rubber 16 hr$^{-1}$ | |
| --- | --- | --- |
| SA concentration (mM) | Superoxide (light) | No Superoxide (dark) |
| 0 |  | 599.5 ± 43.5 |
| 0.5 | 50.2 ± 11.1 | 500.5 ± 29.9 |
| 1 | 74.2 ± 1.3 | 513.0 ± 48.1 |
| 1.5 | 105.3 ± 3.2 | 236.7 ± 3.0 |
| 2 | 18.5 ± 9.24 | 25.1 ± 1.2 |

13.3 DISCUSSION

As with polyunsaturated fatty acids (PUFAs), rubber is extremely susceptible to autoxidation by radicals due to the presence of double bonds in each 5 carbon monomer of the polyisoprene chain. In rubber of $M_r$ 10$^6$ this equals approximately 13,000 monomers per molecule. Peroxidation in natural rubber alters the physical properties of elastomer with the net effect being chain scission and cross linking in addition to the formation of volatile oxidation products (Shelton, Rubber Chem. Tech. 45: 359–377 (1972)). For each peroxide molecule of polyisoprene, one crosslink is formed (Shelton, Rubber Chem. Tech. 45: 359–377 (1972)). In the interior of rubber particles, where oxygen is expected to be limited, cross linking comparable to peroxide vulcanization occurs (Shelton, Rubber Chem. Tech. 45: 359–377 (1972)). These physical changes are undesirable if one imagines that rubber particles have a metabolic function. To maintain rubber stability, one would expect that an antioxidant is necessary in the particles. Hevea rubber particles have such a natural antioxidant in the form of α-tocopherol (Dunphy et al., Nature 207: 521–522 (1965) which is noticeably absent in guayule particles. Despite this, guayule particles show no evidence of lipid peroxidation even though its rubber is rich in polyisoprenes and PUFAs.

Interestingly, guayule particles contain an abundant AOS which accounts for most of the protein in its particles. Moreover, this enzyme is effective at converting lipid hydroperoxides that form as a result of induced autoxidation or lipoxygenase-initiated oxidation. Thus, AOS makes a prime candidate as the antioxidant used in situ by guayule rubber. Being an enzyme rather than a chemical antioxidant could explain why guayule rubber degrades so quickly after harvest. Once harvested, the AOS within the cells is inactivated leaving no antioxidant protection for the rubber within. Hevea rubber, is protected from autoxidation following harvest due to the natural tocopherols present (Dunphy et al., Nature 207: 521–522 (1965)).

As guayule contains AOS as an enzyme antioxidant, the effect of lipid peroxidation on rubber biosynthesis was investigated. Neither AOS inhibition alone, nor superoxide alone significantly inhibit RuT activity. However, in combination these two have a pronounced inhibitory effect on RuT activity (Table 6). There are several possible explanations for this. First, alteration of allylic isoprene initiators by peroxides could induce cross-linking or chain scission that might impair RuT's ability to recognize this substrate or leave an unsuitable terminus for isoprene additions. Second, secondary products of lipid peroxidation, such as aldehydes, can react with sulfhhydryl groups on protein (Tsuchida et al., Chem. Phys. Lipids 44: 297–325 (1987); Beppu et al., Chem. Pharm. Bull. 34: 781–788 (1986) or cause cross-linking of proteins (Tsuchida et al., Chem. Phys. Lipids 44: 297–325 (1987), Beppu et al., Chem. Pharm. Bull. 34:

781–788 (1986) to inactivate them. This could affect any or all proteins associated with rubber particles, including RuT. Third, direct oxidation of proteins, including RuT, could lead to oxidative degradation, causing protein inactivation (Pacifici and Davies, Gerontology 37: 166–180 (1991)). However, high concentrations of oxidant would be necessary as lipid peroxidation is more kinetically favorable than protein oxidation (Murphy et al., Eur. J. Biochem. 210: 139–146 (1992)).

Other proteins may affect RuT activity in rubber particles. In Hevea RuT was linked to another protein known as rubber elongation factor (REF) ((Dennis and Light, J. Biol. Chem. 264: 18608–18617 (1989); Light et al., J. Biol. Chem. 264: 18598–18607 (1989)). It was proposed that REF was necessary to convert FPP synthase, a trans-prenyltransferase that condenses a total of three isoprenes, into RuT, a cis-prenyltransferase that condenses thousands of isoprenes (Light et al., J. Biol. Chem. 264: 18598–18607 (1989). REF has absolutely no sequence similarity to AOS and is an unrelated protein. Moreover, neither REF or REF-like proteins are present in guayule particles. Thus, a REF-like mechanism is not apparent in guayule.

Another treatment which affected rubber suspensions was the lipase plus lipoxygenase incubations. Rubber coagulation in the presence of lipase is most likely due to the destruction of the monolayer which surrounds guayule particles. It is believed that this monolayer, along with the proteins embedded in it, keep particles from coagulating, mimicking the function of the monolayer surrounding seed oil bodies (Tzen and Huang, J. Cell. Biol. 117: 327–335 (1992)). RuT is reported to be an intrinsic membrane protein. The physical proximity of RuT, via membrane anchor, to existing rubber chains might be necessary for further elongation. Lipoxygenase treatment alone did not appear to affect RuT activity. Lipoxygenase treatment and AOS inhibition had a slight affect, inhibiting rubber biosynthesis by 30%.

Cornish et al., Phytochemistry 35: 1425–1428 (1994) showed that immunoinhibition of guayule RPP (ie., AOS) leads to a 45% reduction in RuT activity in guayule. The same antibody resulted in a similar reduction of RuT activity in Ficus and Hevea rubber particles (Siler and Cornish, Phytochemistry 32: 1097–1102 (1993). Moreover, these same antibodies recognized the same $M_r$ protein in particles from all three species, although the protein was less abundant in Hevea (Siler and Cornish, Phytochemistry 32: 1097–1102 (1993)). The experiments described herein, using specific chemical inhibitors of AOS in place of antibodies, agree with the earlier immunoinhibition studies. In that work it was suggested that the LPR or RPP proteins in the particles formed a complex that resulted in RuT. We are proposing that this RPP, now recognized as AOS, acts instead as an antioxidant that is required for RuT activity to exist in the particle, especially under oxidative stress conditions. As in many systems, the balance of prooxidants and defense mechanisms are critical areas of study in lipid peroxidation of biomembranes. Rubber particles may play such a role in plant cellular activities.

14. EXAMPLE: CELL LEAKAGE ANALYZED EVIDENCING ANTIOXIDANT ACTIVITY BY ALLENE OXIDE SYNTHASE

An analysis of cell leakage of transgenic AOS and untransformed tobacco plants was performed to measure the effectiveness of allene oxide synthase as an antioxidant.

Transgenic cv. Samsun tobacco plants that overexposed AOS and untransformed cv. Samsun plants were gown in a growth chamber maintained at 28° C. and an irradiance of 500 μmole quanta per square meter per sec. at 16 hours per day. Leaf disks of transgenic plants (FIG. 20, disks 3, 6, 14 and 17) were compared with untransformed plants (FIG. 20, disk C) according to the general method set forth in Gupta et al., Proc. Natl. Acad. Sci. USA 90: 1629–1633 (1993).

Leaf disks (2 cm$^2$) were collected from tobacco plants and placed in petri dishes (15×60 mm) containing 4 ml of a 1.2 μM methyl viologen (MV) solution and vacuum infiltrated for 5 min. MV values are means ±SD (n=4). The samples were incubated at 22° C. for 16 hours in darkness followed by illumination at 500 μM quanta per square meter per sec. for 2 hours. The leaf disks then were incubated for an additional 16 hours in darkness.

The MV solution was collected for conductivity with leaf disks then was autoclaved for 10 min. at 121° C. The conductivity of the autoclaved solution was again measured. The present electrolyte leakage was determined by dividing the value of conductivity of MV solution by the value obtained after autoclaving.

The results are shown in FIG. 20, which shows substantially less percent electrolyte leakage in the transgenic AOS plants than in the control, untransformed plants, indicating that AOS has a protective effect on cells.

Various publications are cited herein, which are hereby incorporated by reference in their entireties.

We claim:

1. An antioxidant composition comprising an allene oxide synthase, wherein the allene oxide synthase is encoded by a nucleic acid molecule having the nucleic acid sequence of SEQ ID NO: 12.

2. An antioxidant composition comprising an allene oxide synthase, wherein the allene oxide synthase has the amino acid sequence of SEQ ID NO: 12.

* * * * *

UNITED STATES PATENT AND TRADEMARK OFFICE
CERTIFICATE OF CORRECTION

PATENT NO.   : 6,132,711
DATED        : October 17, 2000
INVENTOR(S)  : Backhaus et al.

It is certified that error appears in the above-identified patent and that said Letters Patent is hereby corrected as shown below:

Column 25,
Table 1, row Cucumber, col. TAG:
             X
"X" should read --        --
                 73.7

Column 25,
Table 1, row Jojoba**, col. Other NL:
                WE(97%)
"FFA (1.5%)" should read --        --
                FFA(1.5%)

Column 27,
Table 1, row Bean cotyledon, col. Other NL:
                S,FFA,HC
"S, FFA, HC," should read --        --;
                SE, WE
and "(1991lb)" should read -- (1991b) --;
and "MeKegnet" should read -- McKegney --

Column 27,
Table 1, row Guayule§§, col. Other NL: "LCOG" should read -- LCOH --

Column 43,
Table 6 (heading):
The sentence beginning with "Inset" should be deleted Signed and Sealed this Nineteenth Day of March, 2002

*Attest:*

JAMES E. ROGAN
*Attesting Officer*    Director of the United States Patent and Trademark Office